US009890187B2

(12) United States Patent
Odysseos et al.

(10) Patent No.: US 9,890,187 B2
(45) Date of Patent: Feb. 13, 2018

(54) PROTOTYPE SYSTEMS OF THERANOSTIC BIOMARKERS FOR IN VIVO MOLECULAR MANAGEMENT OF CANCER

(71) Applicants: Andreani Odysseos, Nicosia (CY); Costas Pitris, Nicosia (CY); Anastasios Keramidas, Nicosia (CY)

(72) Inventors: Andreani Odysseos, Nicosia (CY); Costas Pitris, Nicosia (CY); Anastasios Keramidas, Nicosia (CY)

(73) Assignee: EPOS-IASIS RESEARCH AND DEVELOPMENT, LTD. (CY)

( * ) Notice: Subject to any disclaimer, the term of this patent is extended or adjusted under 35 U.S.C. 154(b) by 0 days.

(21) Appl. No.: 14/751,795

(22) Filed: Jun. 26, 2015

(65) Prior Publication Data

US 2016/0376298 A1    Dec. 29, 2016

(51) Int. Cl.
  *C07F 15/00* (2006.01)
  *A61K 49/00* (2006.01)
(52) U.S. Cl.
  CPC ...... *C07F 15/0053* (2013.01); *A61K 49/0021* (2013.01); *A61K 49/0052* (2013.01)
(58) Field of Classification Search
  None
  See application file for complete search history.

(56) References Cited

U.S. PATENT DOCUMENTS

| | | | |
|---|---|---|---|
| 6,281,196 B1 | 8/2001 | Pettit et al. |
| 6,309,672 B1 | 10/2001 | Bae et al. |
| 6,589,567 B2 | 7/2003 | Bae et al. |
| 6,596,760 B1 | 7/2003 | Chen et al. |
| 6,770,742 B1 | 8/2004 | Ullrich et al. |
| 7,223,757 B2 | 5/2007 | Wittman et al. |
| 7,250,409 B2 | 7/2007 | Boger |
| 7,294,643 B2 | 11/2007 | Kerwin |
| 7,381,824 B2 | 6/2008 | Hong et al. |
| 7,384,940 B2 | 6/2008 | Agus |
| 7,541,054 B2 | 7/2009 | Damaj |
| 7,700,615 B2 | 4/2010 | Edwards et al. |
| 7,947,653 B1 | 5/2011 | Sordella et al. |
| 7,960,435 B2 | 6/2011 | Njar et al. |
| 8,143,226 B2 | 3/2012 | Goldfine et al. |
| 8,323,621 B2 | 12/2012 | Bornhop et al. |
| 8,337,813 B2 | 12/2012 | Schultz Sikma et al. |
| 8,367,040 B2 | 2/2013 | Yang et al. |
| 8,372,868 B2 | 2/2013 | Bomhop et al. |
| 8,565,892 B2 | 10/2013 | Nayfach-Battilana et al. |
| 8,568,690 B2 | 10/2013 | Lu et al. |
| 8,580,230 B2 | 11/2013 | Sukerkar et al. |
| 8,580,231 B2 | 11/2013 | Sukerkar et al. |
| 8,592,459 B2 | 11/2013 | Aikawa et al. |
| 8,604,044 B2 | 12/2013 | Qian et al. |
| 8,614,290 B2 | 12/2013 | Wester et al. |
| 8,628,750 B2 | 1/2014 | Wester et al. |
| 8,651,113 B2 | 2/2014 | Seeney et al. |
| 8,703,097 B2 | 4/2014 | Jaffray et al. |
| 8,722,017 B2 | 5/2014 | Fu et al. |
| 8,722,428 B2 | 5/2014 | Geddes |
| 8,734,761 B2 | 5/2014 | Willard et al. |
| 8,753,605 B2 | 6/2014 | Cheng et al. |
| 8,753,606 B2 | 6/2014 | Chung et al. |
| 2008/0226562 A1 | 9/2008 | Groves et al. |
| 2012/0107229 A1 | 5/2012 | Huang et al. |

FOREIGN PATENT DOCUMENTS

| WO | 2007-029251 A2 | 3/2007 |
| WO | 2007/029251 A2 | 3/2007 |

OTHER PUBLICATIONS

Garcia. Journal of Biological Inorganc Chemistry, 2009, 14, 261-71, online Nov. 13, 2008.*
Garcia. Metallomics, 2010, 2, 571-80.*
Chen, et al., Probing Real-Time Response to Multitargeted Tyrosine Kinase Inhibitor 4-N-(3'-Bromo-Phenyl) Amino-6, 7-Dimethoxyquinazoline in Single Living Cells Using Biofuntionalized Quantum Dots, Nanomedicine & Nanotechnology Journal, 2011, vol. 2, Issue 6, 1000117, pp. 1-5.
Sylvester, et al., Role of GTP-binding proteins in reversing the antiproliferative effects of tocotrienols in preneoplastic mammary epithelial cells, Asia Pacific J. Clin. Nutr., 2002, 11(Suppl.), pp. S452-S459.
Yadav, et al., Targeting Inflammatory Pathways by Triterpenoids for Prevention and Treatment of Cancer, Toxins, 2010, 2, pp. 2428-2466.
Vraka, et al., Synthesis and study of the cancer cell growth inhibitory properties of α-, γ-tocopheryl 2-phenylselenyl succinates, Bioorganic & Medicinal Chemistry, 14, 2006, pp. 2684-2696.
Extended European Search Report, Application No. EP 15 17 4121 dated Dec. 7, 2015.
Extended European Search Report for corresponding European Application No. EP 15 17 4121; dated Dec. 7, 2015.
Chen et al.; Probing Real-Time Response to Multitargeted Tyrosine Kinase Inhibitor 4-N-(3'-Bromo-Phenyl) Amino-6, 7-Dimethoxyquinazoline in Single Living Cells Using Biofuntionalized Quantum Dots; Nanomedicine & Nanotechnology Journal, 2011, vol. 2, Issue 6, pp. 1-5.
Sylvester et al.; Role of GTP-binding proteins in reversing the antiproliferative effects of tocotrienols in preneoplastic mammary epithelial cells; Asia Pacific J. Clin. Nutr., 2002, 11(Suppl.), pp. S452-S459.
Yadav et al.; Targeting Inflammatory Pathways by Triterpenoids for Prevention and Treatment of Cancer; Toxins, 2010, 2, pp. 2428-2466.
Vraka, et al.; Synthesis and study of the cancer cell growth inhibitory properties of α-, γ-tocopheryl and γ-tocotrienyl 2-phenylselenyl succinates; Bioorganic & Medicinal Chemistry, 14, 2006, pp. 2684-2696.

(Continued)

*Primary Examiner* — Noble E Jarrell
(74) *Attorney, Agent, or Firm* — Tarolli, Sundheim, Covell & Tummino, LLP

(57) ABSTRACT

The present invention relates to a theranostic system comprising a beacon and a compound selected from the group consisting of a quinazoline-based tyrosine kinase inhibitor and a natural product. The theranostic systems have use in the therapy and diagnosis of tyrosine kinase related malignancies.

16 Claims, 5 Drawing Sheets

(56) References Cited

OTHER PUBLICATIONS

Ward; Near-infrared electrochromic materials for optical attenuation based on transition-metal coordination complexes; J. Solid State Electrochem., 2005, pp. 778-787.

Yano et al.; Vitamin E inhibits cell proliferation and the activation of extracellular signal-regulated kinase during the promotion phase of lung tumorigenesis irrespective of antioxidative effect; Carcinogenesis, vol. 21 No. 11, 2000, pp. 2129-2133.

Kaim; Concepts for metal complex chromophores absorbing in the near infrared; Coordination Chemistry Reviews, 2011, pp. 2503-2513.

Zarogoulidis et al.; Tocopherols and tocotrienols as anticancer treatment for lung cancer: future nutrition; Journal of Thoracic Disease, vol. 5, No. 3, Jun. 2013, pp. 349-352.

* cited by examiner

PROTOTYPE SYSTEMS OF THERANOSTIC BIOMARKERS FOR IN VIVO MOLECULAR MANAGEMENT OF CANCER

FIELD OF THE INVENTION

The present invention relates to theranostic systems and their use in the therapy and diagnosis of tyrosine kinase related malignancies.

BACKGROUND OF THE INVENTION

Tyrosine Kinase Receptors (TKR) are known to be implicated in the initiation and progression of multiple multifunctional malignancies such as colorectal cancer (CRC), lung, head & neck, breast, prostate, gastrointestinal, brain tumors and melanoma.

Colorectal cancer is the second most common cause of cancer-related deaths in the developed world. In Europe, there has been an average annual estimate of 1.7 million cancer associated deaths (Ferlay J., Parkin D. M., Steliarova-Foucher E., *Eur. J. Cancer,* 2010 March:46(4):765-81).

The tyrosine kinase receptors (TKRs), largely epitomized by the ERB-B family of proto-oncogenes (ERB1-4), contain (i) an extracellular ligand-binding domain (domains I-IV), (ii) a single membrane spanning region, (iii) a juxtamembrane nuclear localization signal, and (iv) a cytoplasmic tyrosine kinase domain. ERBB1, the epidermal growth factor receptor-axis (EGFR-axis) has been the most comprehensively studied molecular target in oncology therapeutics over the past decade and is now a validated target for the treatment of cancer patients (Wheeler D. L., Dunn E. F., Harari P. M., *Nat. Rev. Clin. Oncol.,* 2010 September; 7(9):493-507).

FDA approval for monoclonal antibodies (mAbs) against CRC has been active since 2004. In parallel, the rational design of quinazoline-based anti-EGFR tyrosine kinase inhibitors (TKIs) came to the fore. Unfortunately, coincident with this interest in targeting EGFR, was the identification of intrinsic and acquired resistance to EGFR inhibiting agents. The first uniform clinical definition of acquired resistance to EGFR inhibitors was reported in January 2010 (Jackman D., *J. Clin. Oncol.,* 2010; 28:357-66).

The capacity of cancer cells to adapt to treatment suggests that additional mechanisms of resistance to EGFR inhibitors may have a key role in regulating tumor response, such as the induction of tumor/stromal interactions (angiogenesis), translocation of surface receptors to the nucleus, altered DNA damage response, and as yet undiscovered mutations. Intrinsic and acquired resistance to EGFR inhibitors is increasingly well-recognized, and epitomized by (i) genetic and epigenetic variations of genes in the EGFR oncogenic cascade (Yarden Y., Sliwkowski M. X., *Nat. Rev. Mol. Cell. Biol.,* 2001 February; 2(2):127-37), (ii) expression of the EGFRvIII variant, deprived of the extracellular ligand binding domain (Learn C. A., Hartzell T. L., Wikstrand C. J., Archer G. E., Rich J. N., Friedman A. H., Friedman H. S., Bigner D. D., Sampson J. H., *Clin. Cancer Res.* 2004 May 1; 10(9):3216-24), and (iii) mitochondrial and nuclear translocation of constitutively activated EGFR (Lo H. W., *Breast Cancer Res. Treat.* (2006)95:211-18). As data accrues implicating the functional impact of EGFRvIII as well as mitochondrial and nuclear EGFR, it becomes increasingly important to understand the extent to which these mechanisms may contribute to the therapeutic response to EGFR-targeted therapies and design strategies for selective targeting of these variants.

In the post-genetics personalized medicine era, major issues challenging the successful application of targeted and personalized therapies along the TKR axes include: (i) early detection and intervention at the molecular level with concurrent probing of biomarkers underlying compromised responsiveness or resistance to targeted anti-TKR therapies; and (ii) management of resistance and reconstitution of responsiveness with minimally toxic therapies and strategies that enhance localized delivery. While several theranostic agents against TKR have been reported, they are based on monoclonal antibodies or anti-EGFR peptides, which explicitly target the extracellular binding domains thus sparing the truncated EGFRvIII variant.

Targeted therapies combined with imaging and/or sensing probes, also denoted as "beacons" comprise targeted theranostics. Near-infra-red (NIR) emitting probes are mostly preferred for biological applications due to: (a) lack of native NIR fluorescence in biological systems leading to highly sensitive detection, delineating molecular structures in pM (picomolar) concentrations (Weisseleder, 2003); (b) low scattering of NIR photons allowing for better image resolution (Cheong 1990); and (c) deep-in tissue penetration permitting non-invasive imaging (Sokolov 2003).

Magnetic resonance imaging (MRI), on the other hand, has high resolution but significant limitations due to inherent low sensitivity of the MR probes which makes validation of in vivo imaging experiments by more than one approach essential. This problem cannot be solved by merely adding two different classes of probes, e.g. optical and MRI together, unless they have identical pharmacokinetic properties (Flurrano, 2007).

Optical imaging with anti-EGFR antibodies failed to introduce a therapeutic functionality (EI-Sayed IH, 2005). Radiolabelled TKI, exhibit non-specific binding and suboptimal pharmacokinetic properties due to low hydrophilicity (Abourbech G, 2007). MRI probes are very limited (Suwa T, 1998). Thus, multimodal probes are needed in order to solve this problem and provide scaffolds for the amplification of MRI contrast agents.

The majority of bimodal agents reported so far include gadolinium complexes or iron oxide nanoparticles conjugated to fluorescent organic dyes (Mulder, 2007). Lanthanides, however, exhibit complementary properties over organic fluorophores, including resistance to photobleaching, long luminescence lifetimes, minimal or no reabsorption and sharp emission bands (Petoud, 2003; Zhang, 2005). The first successful attempt to develop lanthanide chelators combining both MRI and NIR luminescent activities has achieved long fluorescence lifetimes in metal-organic frameworks (Koullourou, 2008). Despite limited efforts to achieve bimodal imaging with mixtures of these agents (Manning, 2008), combining optical with magnetic properties within the same stable molecular structure also possessing anti-EGFR therapeutic potential, with optimized in vivo stability, targeting efficacy and desirable pharmacokinetics for clinical translation through high synthetic versatility remains a major challenge. Despite their favourable properties in term of sensing properties and drug delivery efficacies, the plethora of nanosized systems reported so far have not enjoyed regulatory approval (with the exception of a few examples in the polymeric and liposomal sub-group). Therefore, organometallic complexes with favourable pharmacokinetics like the complexes disclosed herein are of high promise for clinical use.

The past decades have witnessed well-documented epidemiologic associations of numerous natural products with cancer incidence and/or progression. Genomic and proteomic studies have correlated certain natural products, mainly isoprenoids, with molecular-level processes and have attributed to them functional relevance with specific molecular targets.

Natural triterpenic diols, extracted from olive oil, have been shown to promote apoptosis in astrocytoma cells through Reactive Oxygen Species (ROS)-mediated mitochondrial depolarization and Jun-Terminal Kinases (JNK) activation (Martin R., Ibeas E., Carvalho-Tavares J., Hernandez M., Ruiz-Gutierrez V., Nieto M. L., *PLoS One.* 2009 June 22; 4(6):e5975).

Natural terpenoids have also been implicated in the targeting of apoptosis pathways. Treatment of breast and prostate cancer with triterpenoids has been shown to target inflammatory pathways which can be exploited for the prevention and treatment of cancer (Yadav V. R., Prasad S., Sung B., Kannappan R., Aggarwal B. B., *Toxins* (Basel), 2010 October; 2(10):2428-66). Particular targets downstream of TKRs have also been identified as therapeutic targets of isoprenoids. Ras pathway activation in gliomas has proven to be a critical target of the treatment with intranasal administration of perillyl alcohol (da Fonseca C. O., Linden R., Futuro D., Gattass C. R., Quirico-Santos T., *Arch. Immunol. Ther. Exp.* (Warsz), 2008 July-August; 56(4):267-76). Further studies are currently trying to unravel the activities and propose a unifying mechanism of the anticancer actions of triterpenoids and their synthetic analogs (Safe S. H., Prather P. L., Brents L. K., Chadalapaka G., Jutooru I., *Anticancer Agents Med. Chem.*, 2012 December; 12(10):1211-20).

Tocotrienols, a group of vitamin E derivatives, have been strongly associated with TKR pathways. Based on the inducible c-Rous sarcoma tyrosine kinase (c-SRC) inhibitory properties of tocotrienols, it may be postulated that tocotrienols have anti-cancer effects in SRC-mediated malignancies (e.g. gliomas, melanomas or malignancies associated with chronic inflammatory disorders). Antiproliferative effects of tocotrienols in pre-neoplastic mammary epithelial cells do not reflect a reduction in EGF-receptor mitogenic responsiveness. Rather, they result from the inhibition of early post-receptor events involved in cAMP production upstream from EGF-dependent MAPK and phosphoinositide 3-kinase/AKT mitogenic signalling (Sylvester P. W., Nachnani A., Shah S., Briski K. P., *Asia Pac. J. Clin. Nutr.*, 2002; 11 Suppl 7:S452-9).

Recently, cancer stem cells, a cell population with dominant expression of TKR and a rapidly progressing area of cancer initiation and progression, have been implicated in the theory for cancer chemoprevention by natural dietary compounds (Li Y., Wicha M. S., Schwartz S. J., Sun D., *J. Nutr. Biochem.*, 2011 September; 22(9):799-806). Retinoids, a nutrient category with strong epidemiologic association with cancer prevention, are shown to arrest breast cancer proliferation through selective reduction of the duration of receptor tyrosine kinase signalling (Tighe A. P., Talmage D. A., *Exp. Cell. Res.* 2004 December 10; 301(2):147-57). Despite these associations and multifaceted research, there has been no undertaking to exploit the signal modulating and anticancer attributes of selected phytochemicals within theranostic systems.

SUMMARY OF THE INVENTION

According to a first aspect, the present invention provides a theranostic system including:
a beacon; and at least one compound selected from the group consisting of
a quinazoline-based tyrosine kinase inhibitor; and
a natural product.

In an embodiment, the theranostic system includes the beacon and the quinazoline-based tyrosine kinase inhibitor. In other words, the theranostic system of this embodiment does not comprise the natural product. In this embodiment, the theranostic system may either be a combination of the beacon and the quinazoline-based tyrosine kinase inhibitor (i.e. B+quinazoline) or a complex of the beacon and the quinazoline-based tyrosine kinase inhibitor (i.e. [B-quinazoline]). The "-" indicates that there is a chemical bond (e.g. covalent) between the beacon and the quinazoline-based tyrosine kinase inhibitor.

In an embodiment, the theranostic system includes the beacon and the natural product. In other words, the theranostic system of this embodiment does not comprise the quinazoline-based tyrosine kinase inhibitor. In this embodiment, the theranostic system may either be a combination of the beacon and the natural product (Le. B+NatP) or a complex of the beacon and the natural product (i.e. [B-NatP]). The "-" indicates that there is a chemical bond (e.g. covalent) between the beacon and the natural product.

In an embodiment, the theranostic system includes the beacon, the quinazoline-based tyrosine kinase inhibitor and the natural product. In this embodiment, the theranostic system may be a combination of the beacon, the quinazoline-based tyrosine kinase inhibitor and the natural product (i.e. B+quinazoline+NatP). Alternatively, in this embodiment, the theranostic system may either be a combination of a complex of the beacon and the quinazoline-based tyrosine kinase inhibitor and the natural product (i.e. [B-quinazoline]+NatP), or a combination of a complex of the beacon and the natural product and the quinazoline-based tyrosine kinase inhibitor (i.e. [B-NatP]+quinazoline).

In the present invention, the beacon (B) is any imaging/sensing agent that can be detected by one or more of optical, magnetic, radiofrequency (RF) or positron emission tomography (PET) detection methods.

In an embodiment, the beacon is a rhodamine, cyanine or coumarin or derivatives thereof, a fluorescent quantum dot, a fluorescent lanthanide complex, a paramagnetic lanthanide complex, a radionucleotide (for PET), or a heterometallic multimodal compound. Preferably, the beacon is a rhodamine, cyanine or coumarin or derivatives thereof, a fluorescent lanthanide complex, a paramagnetic lanthanide complex or a heterometallic multimodal compound.

In an embodiment, the beacon is selected from the group consisting of carbocyanine, oxocarbocyanine, macrocyanine, indocarbocyanine, fluorescein, polymethine, rhodamine, xanthene, Cy®5, Cy5.5®, Cy, ViVoTag®-660, 680 and 750; AlexaFluor® 660, 680, 700, 750, 790; Dy-677, Dy-780; Dylight 680; HiLyte™Fluor 680, 750; IRDye 800CW, 700DX and ADS 780WS, 830WS, 832WS.

In an embodiment, the beacon is a heterometallic multimodal compound.

In an embodiment, the heterometallic multimodal compound includes: (1) a functionalised macrocyclic lanthanide complex; and (2) a poly-pyridyl near infra-red (NIR) emitter transition metal complex. In an embodiment, the heterometallic multimodal compound has the structure of general Formula A.

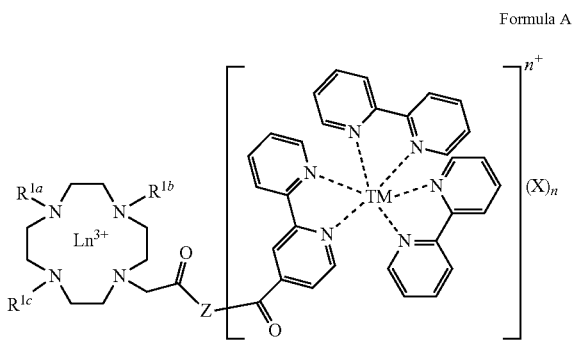

Formula A

In Formula A:
$R^{1a}$, $R^{1b}$ and $R^{1c}$ each independently represent a hydrogen atom or an optionally substituted alkyl, acyl, aryl or heteroaryl group (preferably an optionally substituted alkyl or acyl group);
$Ln^{3+}$ is a trivalent lanthanide metal;
TM is a transition metal capable of near infrared emission;
X is a negatively charged counterion;
Z is represented by O, NH, S, a poly(ethylene glycol) linker (e.g. TEG or HEG), a $C_1$-$C_{20}$ aliphatic chain (e.g. $C_1$-$C_{10}$, preferably $C_5$) or a conjugate of a poly(ethylene glycol) linker with a $C_1$-$C_{20}$ aliphatic chain, wherein the poly (ethylene glycol) linker and the $C_1$-$C_{20}$ aliphatic chain are conjugated via a peptidic or esteric bond; and
n is 2.

In an embodiment, $R^{1a}$, $R^{1b}$ and $R^{1c}$ each independently represent a hydrogen atom, $-(CH_2)_mP(=O)(OH)_2$, or $-(CH_2)_mC(=O)OH$, wherein m is 1, 2, 3, 4 or 5 (preferably, m is 1). In an embodiment, $R^{1a}$, $R^{1b}$ and $R^{1c}$ each independently represent $-CH_2P(=O)(OH)_2$, or $-CH_2C(=O)OH$.

In an embodiment, $Ln^{3+}$ is a trivalent lanthanide metal selected from the group consisting of La(III), Ce(III), Pr(III), Nd(III), Sm(III), Eu(III), Gd(III), Tb(III), Dy(III), Ho(III), Er(III), Tm(III), Yb(III) and Lu(III). The trivalent lanthanide metal is preferably $Gd^{3+}$.

In an embodiment, TM is a transition metal selected from the group consisting of: ruthenium, rhenium and iridium.

In an embodiment, X is a negatively charged counterion selected from the group consisting of: $PF_6$ and $ClO_4$.

In an embodiment, Z is O.

In an embodiment, the quinazoline-based tyrosine kinase inhibitor has the general structure defined by Formula I below.

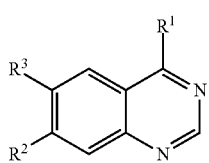

Formula I

In Formula I:
$R^1$ represents a hydrogen atom, a halogen atom, $N_3$, CN, $NO_2$, $OR^a$, $N(R^a)(R^b)$, $SR^a$ or an optionally substituted alkyl, alkenyl, alkynyl, acyl, cycloalkyl, cycloalkenyl, aryl, aralkyl, heterocyclyl or heterocyclylalkyl group;
$R^2$ represents a hydrogen atom, a halogen atom, $OR^a$, $SR^a$, $N(R^a)(R^b)$, or an optionally substituted alkyl, alkenyl, alkynyl, acyl, cycloalkyl, cycloalkenyl, aryl, aralkyl, heterocyclyl or heterocyclylalkyl group;
$R^3$ represents a hydrogen atom, a halogen atom, $N_3$, ON, $NO_2$, $OR^a$, $SR^a$ or $N(R^a)(R^b)$, or an optionally substituted alkyl, alkenyl, alkynyl, acyl, cycloalkyl, cycloalkenyl, aryl, aralkyl, heterocyclyl or heterocyclylalkyl group;
wherein $R^a$ and $R^b$ each independently represent a hydrogen atom or an optionally substituted alkyl, alkenyl, alkynyl, acyl, cycloalkyl, cycloalkenyl, aryl, aralkyl, heterocyclyl or heterocyclylalkyl group.

In an embodiment, $R^2$ represents a hydrogen atom, a halogen atom, $OR^c$, $N(R^c)(R^d)$, $SR^c$ or an optionally substituted alkyl group; wherein $R^c$ and $R^d$ each independently represent a hydrogen atom or an optionally substituted alkyl or acyl group.

In an embodiment, $R^2$ represents a hydrogen atom, $N(R^e)(R^f)$, $SR^e$, $OR^e$ or $CH_2(R^e)$; wherein $R^e$ and $R^f$ each independently represent a hydrogen atom, $-C(=O)CH_2Cl$, $-C(=O)CH_2Br$, $-C(=O)CH_2F$, $-C(=O)Me$, $-C(=O)^tBu$, $-C(=O)CF_3$ or $-C(=O)CH_2OMe$.

In an embodiment, $R^e$ and $R^f$ each independently represent a hydrogen atom or $-C(=O)CH_2Cl$.

In an embodiment, $R^2$ represents a hydrogen atom, $-NHC(=O)CH_2Cl$, $-SC(=O)CH_2Cl$, $-OC(=O)CH_2Cl$, $-NHC(=O)CH_2Br$, $-SC(=O)CH_2Br$, $-OC(=O)CH_2Br$, $-NHC(=O)CH_2F$, $-SC(=O)CH_2F$, $-OC(=O)CH_2F$, $-NHC(=O)Me$, $-NHC(=O)^tBu$, $-NHC(=O)CF_3$, $-NHC(=O)CH_2OMe$, $-SC(=O)Me$, $-SC(=O)^tBu$, $-SC(=O)CF_3$, $-SC(=O)CH_2OMe$, $-OC(=O)Me$, $-OC(=O)^tBu$, $-OC(=O)CF_3$ or $-OC(=O)CH_2OMe$. In an embodiment, $R^2$ is $-NHC(=O)CH_2Cl$.

In an embodiment, $R^3$ represents a hydrogen atom, a halogen atom, $NO_2$, CN, $N_3$, $OR^g$, $N(R^g)(R^h)$, $SR^g$ or an optionally substituted alkyl, alkenyl or alkynyl group; wherein $R^g$ and $R^h$ each independently represent a hydrogen atom or an optionally substituted alkyl, acyl, alkenyl or alkynyl group.

In an embodiment, $R^3$ represents a hydrogen atom, a halogen atom, $NO_2$, CN, $N_3$, $OR^i$ or $NH(R^i)$, wherein $R^i$ is $-C(=O)CR^jCR^kR^l$, $-C(=O)Me$, $-C(=O)^tBu$ or $-C(=O)CF_3$, $-C(=O)CH_2OMe$; and wherein $R^j$, $R^k$ and $R^l$ each independently represent a hydrogen atom or an optionally substituted alkyl, alkenyl or alkynyl group.

In an embodiment $R^i$ is an acroyl, crotonoyl, pentenoyl or pentadienoyl group.

In an embodiment, the quinazoline-based tyrosine kinase inhibitor is an anilinoquinazoline-based tyrosine kinase inhibitor of general Formula II.

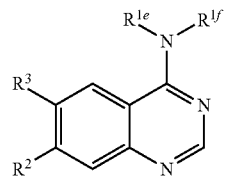

Formula II

In the anilinoquinazoline of Formula II:
$R^{1e}$ and $R^{1f}$ each independently represent a hydrogen atom or an optionally substituted alkyl, alkenyl, alkynyl, acyl, cycloalkyl, cycloalkenyl, aryl, aralkyl, heterocyclyl or heterocyclylalkyl group; and
$R^2$ and $R^3$ are as already defined herein.

In an embodiment, $R^{1e}$ represents a hydrogen atom and $R^{1f}$ represents an optionally substituted alkyl, alkenyl, alkynyl, acyl, cycloalkyl, cycloalkenyl, aryl, aralkyl, heterocyclyl or heterocyclylalkyl group.

In an embodiment, $R^{1e}$ represents a hydrogen atom and $R^{1f}$ represents an optionally substituted aryl, aralkyl, heterocyclyl or heterocyclylalkyl group.

In an embodiment, $R^{1e}$ represents a hydrogen atom and $R^{1f}$ represents

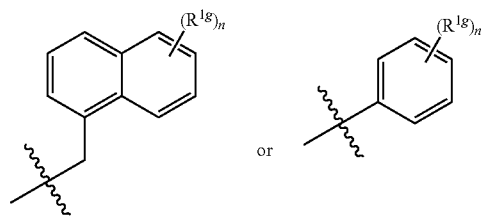

wherein n is 0 to 4, and each $R^{1g}$ independently represents a hydrogen atom, a halogen, $NO_2$, CN, $N_3$, or an optionally substituted alkyl, alkenyl, alkynyl, alkoxy, acyl, cycloalkyl, cycloalkenyl, aryl, aralkyl, heterocyclyl or heterocyclylalkyl group.

In an embodiment, the natural product is a phytochemical (i.e. plant-derived) natural product. In an embodiment, the natural product is a marine-derived natural product.

In an embodiment, the natural product, marine-derived natural product or phytochemical natural product contains one or more aromatic rings and one or more hydroxyl groups.

In an embodiment, the natural product is selected from: (i) chromanols of the vitamin E superfamily (e.g. α, β, γ, δ tocopherols and α, β, γ, δ tocotrienols), and precursors, analogues and derivatives thereof; (ii) poly(oxo)phenolic compounds (such as tannins, gallic acid, catechols and epicatechin), and analogues and derivatives thereof; (iii) retinoids, and analogues and derivatives thereof; (iv) resveratrol, and precursors, analogues and derivatives thereof; (v) flavonoids; and (vi) terpenes and terpenoids.

In an embodiment, the natural product is linked (conjugated) to the beacon (B) with an enzymatically cleavable esteric or peptidic bond. In an embodiment, the natural product is linked to the beacon (B) with a poly(ethylene glycol) linker (e.g. TEG or HEG), (ii) a $C_1$-$C_{20}$ aliphatic chain (e.g. $C_1$-$C_{10}$, preferably $C_5$); or (iii) a conjugate of a poly(ethylene glycol) linker with a $C_1$-$C_{20}$ aliphatic chain, wherein the poly(ethylene glycol) linker and the $C_1$-$C_{20}$ aliphatic chain are conjugated via a peptidic or esteric bond.

In an embodiment, the quinazoline-based tyrosine kinase inhibitor of Formula I or the anilinoquinazoline-based tyrosine kinase inhibitor of Formula II is linked to the beacon (B) with an enzymatically cleavable esteric or peptidic bond. In an embodiment, the anilinoquinazoline-based tyrosine kinase inhibitor is linked to the beacon (B) with a poly(ethylene glycol) linker (e.g. TEG or HEG), (ii) a $C_1$-$C_{20}$ aliphatic chain (e.g. $C_1$-$C_{10}$, preferably $C_5$); or (iii) a conjugate of a poly(ethylene glycol) linker with a $C_1$-$C_{20}$ aliphatic chain, wherein the poly(ethylene glycol) linker and the $C_1$-$C_{20}$ aliphatic chain are conjugated via a peptidic or esteric bond.

In an embodiment, the theranostic system includes a compound of Formula B

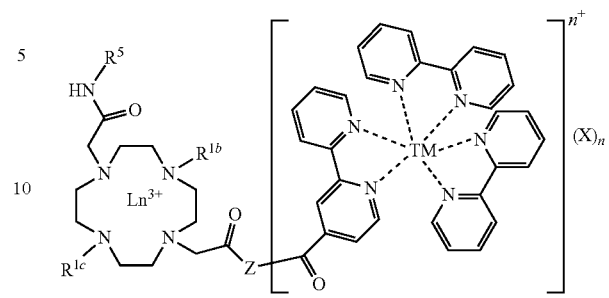

Formula B wherein:
$R^{1b}$, $R^{1c}$, $Ln^{3+}$, TM, X, Z and n are as already defined herein; and
$R^5$ is represented by the structure

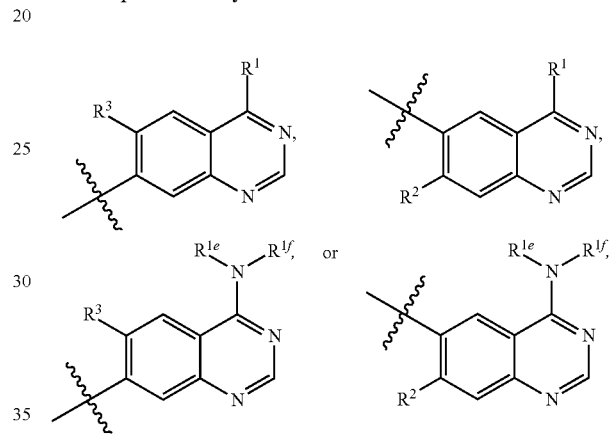

wherein $R^1$, $R^{1e}$, $R^{1f}$, $R^2$ and $R^3$ are as already defined herein.

In an embodiment, $R^{1b}$ and $R^{1c}$ each independently represent a hydrogen atom, $-(CH_2)_m P(=O)(OH)_2$, or $-(CH_2)_m C(=O)OH$, wherein m is 1, 2, 3, 4 or 5 (preferably, m is 1).

In an embodiment, $Ln^{3+}$ is a trivalent lanthanide metal selected from the group consisting of La(III), Ce(III), Pr(III), Nd(III), Sm(III), Eu(III), Gd(III), Tb(III), Dy(III), Ho(III), Er(III), Tm(III), Yb(III) and Lu(III). The trivalent lanthanide metal is preferably $Gd^{3+}$.

In an embodiment, TM is a transition metal selected from the group consisting of ruthenium, rhenium and iridium.

In an embodiment, X is a negatively charged counterion selected from the group consisting of $PF_6$ and $ClO_4$.

In an embodiment, $R^1$ is selected from the group consisting of a 2-methoxyaniline, 2-bromoaniline, 2-fluoroaniline, 2-chloroaniline, 3-methoxyaniline, 3-bromoaniline, 3-fluoroaniline, 3-chloroaniline, 3,5-difluoroaniline, 3,5-dichloroaniline, 3,5-dibromoaniline, 3-(trifluoromethyl)aniline, 4-chloro-3-(trifluoromethyl)aniline, 3-chloro-4-fluoroaniline, 4-fluoro-3-(trifluoromethyl)aniline, 4-fluoroaniline, 4-methoxyaniline, 4-bromoaniline, 4-chloroaniline, 4-isopropylaniline 3-bromo-5-(trifluoromethyl)aniline, bis(trifluoromethyl)aniline, 4-(tert-butyl)aniline and 1-napthylmethylamine moiety.

In an embodiment, $R^{1a}$ is a hydrogen atom and $R^{1b}$ is selected from a group consisting of a 2-methoxyphenyl, 2-bromophenyl, 2-fluorophenyl, 2-chlorophenyl, 3-methoxyphenyl, 3-bromophenyl, 3-fluorophenyl, 3-chlorophenyl, 3,5,difluorophenyl, 3, 5,dichlorophenyl, 3, 5,dibromophenyl, 3-(trifluoromethyl)phenyl, 4-chloro-3-(trifluoromethyl)phenyl, 3-chloro-4-fluorophenyl, 4-fluoro-3-(trifluoromethyl)phenyl, 4-fluorophenyl, 4-methoxyphenyl, 4-bromophenyl, 4-chlorophenyl, 4-isopropylphenyl 3-bromo-5-(trifluoromethyl)phenyl, bis(trifluoromethyl)phenyl, 4-(tert-butyl)phenyl and 1-napthylmethyl moiety.

In an embodiment, the theranostic system is a compound of Formula C

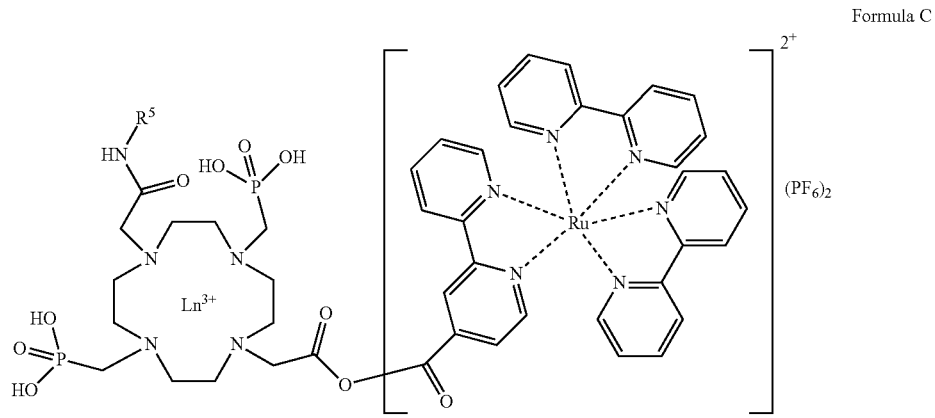

Formula C wherein $R^5$ and $Ln^{3+}$ are as already defined herein.

According to another aspect of the present invention, there is provided a method for treating and/or diagnosing cancer using the theranostic systems of the present invention.

According to another aspect of the present invention, there is provided a method of treating and/or diagnosing cancer in a patient in need thereof comprising administering to the patient the theranostic systems of the present invention.

In an embodiment, the theranostic systems of the present invention can be used in methods of treating and/or diagnosing multiple multifunctional malignancies such as colorectal cancer, lung cancer, head & neck cancer, breast cancer, prostate cancer, gastrointestinal cancer, brain tumors and melanoma.

According to another aspect of the present invention, there is provided the use of the theranostic systems of the present invention for the treatment and/or diagnosis of cancer.

In another aspect of the present invention, there is provided a kit including a container having the theranostic system according to the present invention, as herein described.

At least some of the above and other features of the invention are set out in the claims.

DETAILED DESCRIPTION

Figure 1:
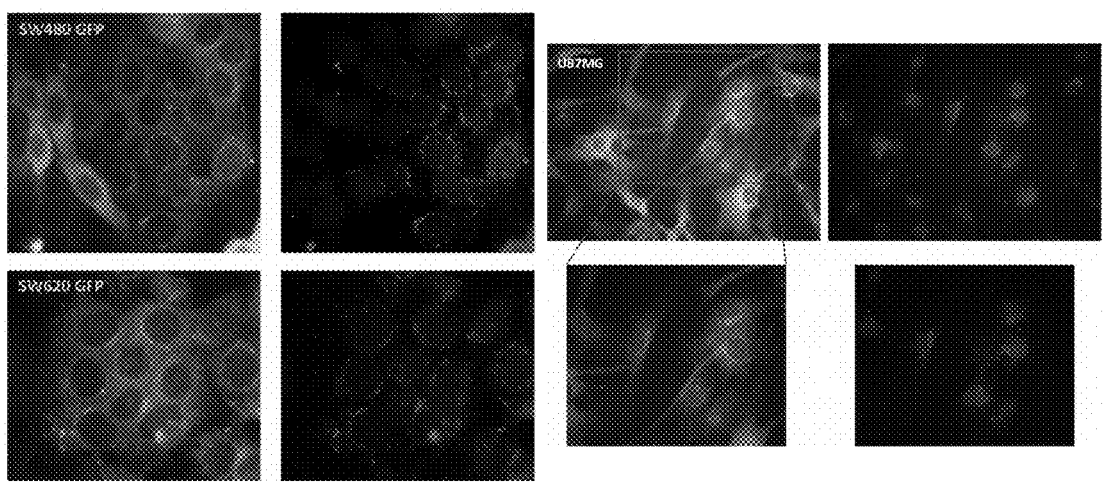
FIG. 1 shows the uptake of a ruthenium complex in green fluorescent protein(GFP)/luciferase (Luc) fluorescently transfected colon cancer (SW480, SW460) and malignant glioma (U87) cells.

The present invention will now be described more fully hereinafter with reference to the accompanying drawings, in which preferred embodiments of the invention are shown. Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. Any publications, patent applications, patents, or other references mentioned herein are incorporated by reference in their entirety. In case of conflict, the present specification, including any definitions, will control.

The materials, methods and examples given are merely illustrative in nature and are not intended to be limiting. Accordingly, this invention may be embodied in different forms and should not be construed as limited to the embodiments set forth herein. Rather, these embodiments are provided so that this disclosure will be thorough and complete, and will fully convey the scope of the invention to those skilled in the art. Other features and advantages of the invention will be apparent from the following detailed description, and from the claims.

The present invention relates to theranostic systems. In the context of the present invention, the theranostic systems allow for therapeutic targeting, modulation of activity and in vivo molecular diagnostics of tyrosine kinases in common malignancies.

The theranostic systems of the present invention serve to interfere with disease progression at the molecular level (treatment), deliver the therapeutic moiety at the desired target site (drug delivery) as well as provide a means of detection for screening, diagnosis, and monitoring of the disease.

More particularly, the disclosures pertaining to interference with disease progression relate to (i) the direct and specific targeting and imaging/sensing of cancer-mediating forms of tyrosine kinases in prevalent and intractable malignancies, (ii) modulation of the tyrosine kinase activity and associated progression of the malignancy by marine-derived natural products or phytochemicals (phytochemical natural products) and their derivatives conjugated in theranostic complexes or (iii) the combinations of the above.

Theranostic systems of the present invention are capable of: (i) specifically targeting a population of malignant cells which express a well-defined and constitutively activated tyrosine kinase contributing to the malignant growth (e.g. the intracellular kinase domain); (ii) reporting the existence and quantifying the abundance of this kinase by means of their sensing and imaging components, with the reporting properties amplified within a fluorescent, magnetic or bimodal (e.g. optical and magnetic) organic or heterometallic compound; (iii) delivering their therapeutic attributes by inhibiting the phosphorylating (and thus cancer potentiating) activity of this kinase; and (iv) modulating the molecular functionalities within the tyrosine kinase pathways and axes towards an augmented specific anticancer effect.

Whilst the theranostic systems of the present invention have a broad application in the field of tyrosine kinase mediated malignancies, they are particularly suitable for variants of the tyrosine kinase trans-membrane receptors (TKR) which: (i) are deprived of their ligand-binding extracellular domain (e.g. variant EGFRvIII in gliomas) or (ii) translocate to the nucleus and mitochondria (e.g. phosphorylated EGFR in lung, colon, breast cancer and gliomas).

Examples of biomarkers which are targets of the theranostic systems of the present invention are members of the tyrosine kinase receptor superfamily, which are epitomized by the epidermal growth factor receptor (EGFR/ERB-I) and include HER2, ERB3, ERB4, VEGFR, PDGFR, IGFR and other trans-membrane receptors thereof and (b) Cluster Domains—CD—(e.g. CD3, CD4, CD8) associated with LCK, FYN, SRC and other kinase-associated receptor thereof) or their downstream effectors whose functions are dependent on those of TKR. Other kinase targets include the members of the molecular pathway(s) downstream of the TKRs axis, such as the members of the MAPK and ERK cascades.

The present invention also relates to the management of malignant diseases by deciphering theranostic biomarkers in the tyrosine kinase axes, i.e. downstream effectors, parallel and converging pathways mediated by any of the tyrosine kinase superfamily members. A major aspect in the overall management of malignant diseases is the management of intrinsic and acquired resistance to current therapies. Well-recognized mechanisms of resistance include (i) mechanisms against chemotherapy, and (ii) molecular mechanisms against targeted therapies within these axes. Chemotherapy-related resistance involves (a) overexpression of efflux transporters, represented by P-glycoprotein and the ATP-binding cassette superfamily, leading to reduced drug accumulation, (b) sequestration of the drug in acidic organelles, (c) resistance to transport of macromolecules and their carriers and (d) acidic and hypoxic microenvironments. Possible approaches for management include (i) inhibition and evasion of drug efflux, (ii) formulations inhibiting transporter activity, (iii) co-delivery of the anticancer drug with a specific inhibitor of the transporter function or its expression, (iv) triggering of drug release, (v) altering rate of drug release and (vi) simultaneous delivery of drug and efflux. Intrinsic and acquired resistance to anti-EGFR therapies is increasingly well-recognized and epitomised by (i) genetic and epigenetic variations of genes in the EGFR oncogenic cascade, (ii) critical downstream effectors RAS/RAF/MEK/ERK and PI3K/AKT/mTOR, (iii) parallel pathways, including VEGFR, (iv) aberrant expression of the EGFRvIII variant, underlining the significance of kinase-domain targeting theranostic systems, and (v) nuclear and mitochondrial translocation and constitutive activation of phosphorylated EGFR (pEGFR). Nucleus and mitochondria-translocated pEGFR define a key role for lipid rafts and endocytosis pathways. Nuclear EGFR modulates transcription factors and the expression of cyclin D1 and defines an emerging target in triple negative breast cancer and lung cancer. Nuclear and mitochondrial translocation is mostly prominent in malignant gliomas and colon cancers intractable to current anti-EGFR therapies.

Herein, any alkyl, alkenyl or alkynyl group, unless otherwise specified, may be linear or branched and may preferably contain up to 6, and especially up to 4 carbon atoms. Preferred alkyl groups are methyl, ethyl, propyl and butyl. Preferred alkenyl and alkynyl groups include propenyl, butenyl, propynyl and butynyl groups. When an alkyl moiety forms part of another group, for example the alkyl moiety of an aralkyl group, it is preferred that it contains up to 6, especially up to 4, carbon atoms. Preferred alkyl moieties are methyl and ethyl.

An aryl group may be any aromatic hydrocarbon group and may preferably contain from 6 to 18, more preferably 6 to 16, particularly 6 to 14, and especially 6 to 10 carbon atoms. Preferred aryl groups include phenyl, naphthyl, anthryl, phenanthryl and pyryl groups, especially a phenyl or naphthyl, and particularly a phenyl group. When an aryl moiety forms part of another group, for example the aryl moiety of an aralkyl group, it is preferred that it is a phenyl, naphthyl, anthryl, phenanthryl or pyryl, especially phenyl or naphthyl, and particularly a naphthyl moiety.

An aralkyl group may be any alkyl group substituted by an aryl group. A preferred aralkyl group contains from 7 to 30, particularly 7 to 24 and especially 7 to 18, carbon atoms, particularly preferred aralkyl groups being benzyl, naphthylmethyl, anthrylmethyl, phenanthrylmethyl and pyrylmethyl groups. A particularly preferred aralkyl group is a naphthylmethyl group.

A cycloalkyl group may be any saturated cyclic hydrocarbon group and may contain from 3 to 12, preferably 3 to 8, and especially 3 to 6, carbon atoms. Preferred cycloalkyl groups are cyclopropyl, cyclopentyl and cyclohexyl groups.

A cycloalkenyl group may be any cyclic hydrocarbon group which contains at least one carbon-carbon double bond. Thus, a cycloalkenyl group is effectively a cycloalkyl group in which at least one carbon-carbon single bond has been replaced by a carbon-carbon double bond. A cycloalkenyl group may therefore contain from 3 to 12, preferably 3 to 8, and especially 3 to 6, carbon atoms. Preferred cycloalkenyl groups are cyclopentenyl and cyclohexenyl groups.

An acyl group may be any group of the general formula R—CO— where R represents an optionally substituted alkyl, alkenyl, alkynyl, cycloalkyl, cycloalkenyl, aryl, aralkyl, heterocyclyl or heterocyclylalkyl group. Preferred acyl groups are acryloyl, crotonoyl, pentenoyl and pentadienoyl groups.

An alkoxy group may be any group of the general formula RO— where R represents an optionally substituted alkyl, alkenyl, alkynyl, cycloalkyl, cycloalkenyl, aryl, aralkyl, heterocyclyl or heterocyclylalkyl group. Preferred alkoxy groups are methoxy, ethoxy, propoxy and butoxy groups. Methoxy is an especially preferred alkoxy group.

A heteroaryl group may be any aromatic monocyclic or polycyclic ring system which contains at least one heteroatom. Preferably, a heteroaryl group is a 5- to 18-membered, particularly a 5- to 14-membered, and especially a 5- to 10-membered, aromatic ring system containing at least one heteroatom selected from oxygen, sulphur and nitrogen atoms. Preferred heteroaryl groups include pyridyl, pyrylium, thiopyrylium, pyrrolyl, furyl, thienyl, indolinyl, isoindolinyl, indolizinyl, imidazolyl, pyridonyl, pyronyl, pyrimidinyl, pyrazinyl, oxazolyl, thiazolyl, purinyl, quinolinyl, isoquinolinyl, quinoxalinyl, pyridazinyl, benzofuranyl, benzoxazolyl and acridinyl groups.

A heterocyclic group may be any monocyclic or polycyclic ring system which contains at least one heteroatom and may be unsaturated or partially or fully saturated. The term "heterocyclic" thus includes heteroaryl groups as defined above as well as non-aromatic heterocyclic groups. Preferably, a heterocyclic group is a 3- to 18-membered, particularly a 3- to 14-membered, especially a 5- to 10-membered, ring system containing at least one heteroatom selected from oxygen, sulphur and nitrogen atoms. Preferred heterocyclic groups include the specific heteroaryl groups named above as well as pyranyl, piperidinyl, pyrrolidinyl, dioxanyl, piperazinyl, morpholinyl, thiomorpholinyl, morpholinosulphonyl, tetrahydroisoquinolinyl and tetrahydrofuranyl groups.

A heterocyclylalkyl group may be any alkyl group substituted by a heterocyclic group. Preferably, the heterocyclic moiety is a 3- to 18-membered, particularly a 3- to 14-membered, and especially a 5- to 10-membered, heterocyclic group as defined above and the alkyl moiety is a $C_{1-6}$ alkyl, preferably $C_{1-4}$ alkyl, and especially methyl, group.

When any of the foregoing substituents are designated as being optionally substituted, the substituent groups which are optionally present may be any one or more of those customarily employed in the development of pharmaceutical compounds and/or the modification of such compounds to influence their structure/activity, stability, bioavailability or other property. Specific examples of such substituents include, for example, halogen atoms, nitro, cyano, hydroxyl, phosphonyl, cycloalkyl, alkyl, alkenyl, haloalkyl, alkoxy, haloalkoxy, amino, alkylamino, dialkylamino, formyl, alkoxycarbonyl, carboxyl, alkanoyl, alkylthio, alkylsulphinyl, alkylsulphonyl, alkylsulphonato, arylsulphinyl, arylsulphonyl, arylsulphonato, carbamoyl, alkylamido, aryl and aralkyl groups.

When any of the foregoing optional substituents represents or contains an alkyl or alkenyl substituent group, this may be linear or branched and may contain up to 12, preferably up to 6, and especially up to 4, carbon atoms. A cycloalkyl group may contain from 3 to 8, preferably from 3 to 6, carbon atoms. An aryl group or moiety may contain from 6 to 10 carbon atoms, phenyl groups being especially preferred. A halogen atom may be a fluorine, chlorine, bromine or iodine atom and any group which contains a halo moiety, such as a haloalkyl group, may thus contain any one or more of these halogen atoms. Phosphonate is an especially preferred phosphonyl group.

Preferred optional substituents include halogen atoms, nitro, cyano, hydroxyl, $C_{1-6}$ alkyl, $C_{1-6}$ haloalkyl, $C_{1-6}$ alkoxy, $C_{1-6}$ haloalkoxy, amino, $C_{1-6}$ alkylamino, di-($C_{1-6}$ alkyl)amino, formyl, $C_{1-6}$ alkoxycarbonyl, carboxyl, $C_{1-6}$ alkanoyl, $C_{1-6}$ alkylthio, $C_{1-6}$ alkylsulphinyl, $C_{1-6}$ alkylsulphonyl, carbamoyl and $C_{1-6}$ alkylamido groups. Particularly preferred optional substituents include halogen atoms, nitro, cyano, hydroxyl, $C_{1-4}$ alkyl, $C_{1-4}$ haloalkyl, $C_{1-4}$ alkoxy and $C_{1-4}$ haloalkoxy groups with halogen atoms being especially preferred.

According to a first aspect, the present invention relates to a theranostic system comprising:
 a beacon; and at least one compound selected from the group consisting of
 a quinazoline-based tyrosine kinase inhibitor; and
 a natural product.

Beacon

The beacon (B) is a sensing or imaging agent that can be detected by optical means (e.g. spectroscopy), by magnetic means (e.g. MRI), by radiofrequency, or by positron emission tomography (PET). For example, the beacon may be any organic or inorganic bioluminescent, fluorescent, magnetic, magnetofluorescent compound, or any magnetic or magnetofluorescent nanoparticle.

The beacon may be unimodal. In other words, the beacon can be detected by a single means of detection only. The beacon may be bimodal or multimodal. In other words, the beacon can be detected by more than one means of detection. For example, a bimodal or multimodal beacon can be detected by optical and magnetic means of detection.

The beacon may be a rhodamine, cyanine, coumarin or derivatives thereof, a fluorescent quantum dot, a fluorescent lanthanide complex, a paramagnetic lanthanide complex, a radionucleotide (for PET), or a heterometallic multimodal compound. Preferably, the beacon is a rhodamine, cyanine or coumarin or derivatives thereof, a fluorescent lanthanide complex, a paramagnetic lanthanide complex or a heterometallic multimodal compound.

The beacon may be a coumarin, rhodamine, xanthene or cyanine dye or derivatives thereof.

The beacon may be a fluorophore emitting in the NIR wavelength region or in the visible region close to NIR region. Known fluorophores of these categories include, but are not limited to carbocyanine, oxocarbocyanine, macrocyanine, indocarbocyanine, fluorescein, polymethine, rhodamine, xanthene, Cy®5, Cy5.5®, Cy, ViVoTag®-660, 680 and 750; AlexaFluor® 660, 680, 700, 750, 790; Dy-677, 780; Dylight 680; HiLyte™Fluor 680, 750; IRDye 800CW, 700DX and ADS 780WS, 830WS, 832WS.

The beacon may be a heterometallic multimodal (e.g. bimodal) compound or mixture (e.g. suitable for optical and/or magnetic and/or radiofrequency imaging). For example, the beacon may be a heterometallic multimodal compound or mixture comprising: (1) a functionalised macrocyclic lanthanide complex; and (2) a poly-pyridyl near infra-red emitter transition metal complex. In a preferred embodiment, the beacon is a heterometallic multimodal compound comprising the functionalised macrocyclic lanthanide complex and the poly-pyridyl near infra-red emitter transition metal complex.

The functionalised macrocyclic lanthanide complex comprises a functionalised macrocyclic ligand and a trivalent (preferably paramagnetic) lanthanide metal.

The trivalent lanthanide metal may be Lanthanum (La (III)), Cerium (Ce(III)), Praseodymium (Pr(III)), Neodymium (Nd(III)), Samarium (Sm(III)), Europium (Eu(III)), gadolinium (Gd(III)), Terbium (Tb(III)), Dysprosium (Dy (III)), Holmium (Ho(III)), Erbium (Er(III)), Thulium (Tm (III)), Ytterbium (Yb(III)), and Lutetium (Lu(III)). Gd(III) and Dy(III) provide MRI and radiofrequency imaging properties. Eu(III) and Tb(III) are emitters of visible light and provide optical imaging attributes. Nd(III) and Yb(III) are NIR emitters and provide optical imaging attributes. Pr(III), Sm(III), Dy(III) and Tm(III) are capable of emitting in both the visible and NIR spectrum. In preferred embodiments of the invention, the trivalent lanthanide metal is Gd(III).

The functionalised macrocyclic lanthanide complex may be a complex defined by Formula D

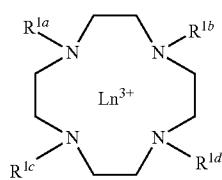

Formula D wherein:
$R^{1a}$, $R^{1b}$, $R^{1c}$ and $R^{1d}$ each independently represent a hydrogen atom or an optionally substituted alkyl or acyl group; and
$Ln^{3+}$ is a trivalent lanthanide metal as already defined herein.

$R^{1a}$, $R^{1b}$, $R^{1c}$ and $R^{1d}$ may each independently represent a hydrogen atom, $-(CH_2)_mP(=O)(OH)_2$, or $-(CH_2)_mC(=O)OH$, wherein m is 1, 2, 3, 4 or 5 (preferably, m is 1). In an embodiment, $R^{1a}$, $R^{1b}$, $R^{1c}$ and $R^{1d}$ are $-CH_2P(=O)(OH)_2$. In an embodiment, $R^{1a}$, $R^{1b}$, $R^{1c}$ and $R^{1d}$ are $-CH_2C(=O)OH$. In an embodiment $R^{1b}$ and $R^{1c}$ are both $-CH_2P(=O)(OH)_2$ and $R^{1a}$ and $R^{1d}$ are both H. In an embodiment, $R^{1b}$ and $R^{1c}$ are both $-CH_2P(=O)(OH)_2$ and $R^{1a}$ and $R^{1d}$ are both $-CH_2C(=O)OH$.

The poly-pyridyl near infra-red emitter transition metal complex may be a complex defined by Formula E.

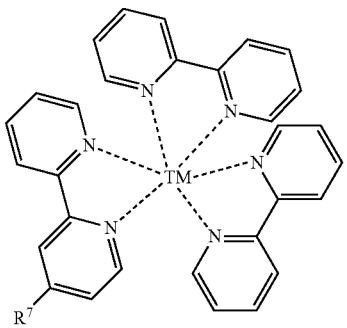

Formula E

In Formula E, TM is a transition metal capable of near infrared emission (e.g. ruthenium, rhenium or iridium) and $R^7$ is represented by a hydrogen atom, or $-CH_2C(=O)OH$. Particularly preferred transition metals are ruthenium and iridium. Ruthenium is most preferred.

In embodiments of the present invention in which the beacon is a heterometallic multimodal compound comprising: (1) a functionalised macrocyclic trivalent lanthanide complex; and (2) a poly-pyridyl near infra-red emitter transition metal complex, the beacon can be defined by Formula A.

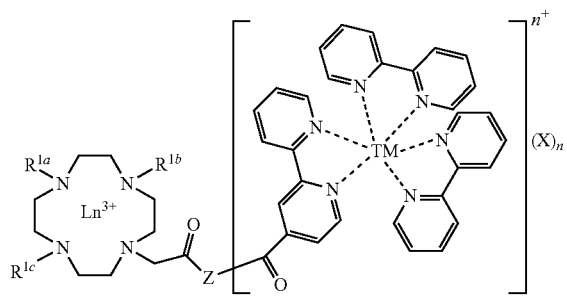

Formula A

In Formula A, $R^{1a}$, $R^{1b}$, $R^{1c}$, $Ln^{3+}$, TM, X, Z and n are as already defined herein. In a preferred embodiment, $Ln^{3+}$ is $Gd^{3+}$, $R^{1a}$, $R^{1b}$ and $R^{1c}$ are $-CH_2P(=O)(OH)_2$; TM is Ru, Re or Ir (preferably Ru); n is 2; Z is O and X is $PF_6$.

The beacon may also be selected from the group consisting of:

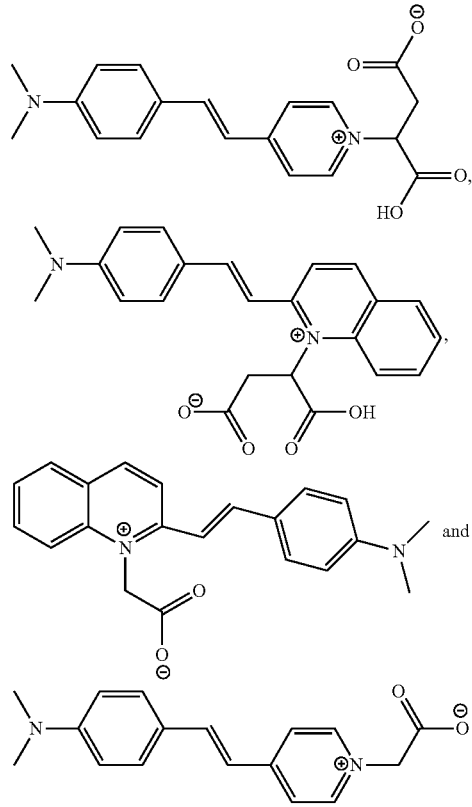

Quinazoline-Based Tyrosine Kinase Inhibitor

The theranostic systems of the present invention may comprise one or more quinazoline-based tyrosine kinase inhibitors. These small molecule kinase inhibitors are preferred over peptides due to lower cost and the reduced likelihood for immunogenicity. To date, the US FDA has approved 28 small-molecule kinase inhibitors, half of which were approved in the past 3 years. These include inhibitors against lipid kinases, protein kinases, serine/threonine kinases and tyrosine kinases.

The quinazoline-based tyrosine kinase inhibitors that can be used in the theranostic systems of the present invention have the general structure defined by Formula I below.

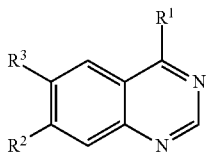

Formula I

In Formula I:
$R^1$ represents a hydrogen atom, a halogen atom, $N_3$, CN, $NO_2$, $OR^a$, $N(R^a)(R^b)$, $SR^a$ or an optionally substituted alkyl, alkenyl, alkynyl, acyl, cycloalkyl, cycloalkenyl, aryl, aralkyl, heterocyclyl or heterocyclylalkyl group;

$R^2$ represents a hydrogen atom, a halogen atom, $OR^a$, $SR^a$, $N(R^a)(R^b)$, or an optionally substituted alkyl, alkenyl, alkynyl, acyl, cycloalkyl, cycloalkenyl, aryl, aralkyl, heterocyclyl or heterocyclylalkyl group;

$R^3$ represents a hydrogen atom, a halogen atom, $N_3$, CN, $NO_2$, $OR^a$, $SR^a$ or $N(R^a)(R^b)$, or an optionally substituted alkyl, alkenyl, alkynyl, acyl, cycloalkyl, cycloalkenyl, aryl, aralkyl, heterocyclyl or heterocyclylalkyl group;

wherein $R^a$ and $R^b$ each independently represent a hydrogen atom or an optionally substituted alkyl, alkenyl, alkynyl, acyl, cycloalkyl, cycloalkenyl, aryl, aralkyl, heterocyclyl or heterocyclylalkyl group.

$R^1$ may be selected from the group consisting of a 2-methoxyaniline, 2-bromoaniline, 2-fluoroaniline, 2-chloroaniline, 3-methoxyaniline, 3-bromoaniline, 3-fluoroaniline, 3-chloroaniline, 3,5,difluoroaniline, 3,5,dichloroaniline, 3,5,dibromoaniline, 3-(trifluoromethyl)aniline, 4-chloro-3-(trifluoromethyl)aniline, 3-chloro-4-fluoroaniline, 4-fluoro-3-(trifluoromethyl)aniline, 4-fluoroaniline, 4-methoxyaniline, 4-bromoaniline, 4-chloroaniline, 4-isopropylaniline 3-bromo-5-(trifluoromethyl)aniline, bis(trifluoromethyl)aniline, 4-(tert-butyl) aniline and 1-napthylmethylamine moiety.

$R^2$ may be selected from the group consisting of —NHC(=O)CH$_2$Cl, —SC(=O)CH$_2$Cl, —OC(=O)CH$_2$Cl, —NHC(=O)CH$_2$Br, —SC(=O)CH$_2$Br, —OC(=O)CH$_2$Br, —NHC(=O)CH$_2$F, —SC(=O)CH$_2$F, and —OC(=O)CH$_2$F. Preferably, $R^2$ is —NHC(=O)CH$_2$Cl, —SC(=O)CH$_2$Cl or —OC(=O)CH$_2$Cl. More preferably $R^2$ is —NHC(=O)CH$_2$Cl.

$R^3$ may be a hydrogen atom or a Michael acceptor group. For example, $R^3$ may be a hydrogen atom or $OR^m$ or $NH(R^m)$, wherein $R^m$ is an acroyl, crotonoyl, pentenoyl or pentadienoyl group. For example, $R^m$ may be selected from the group consisting of:

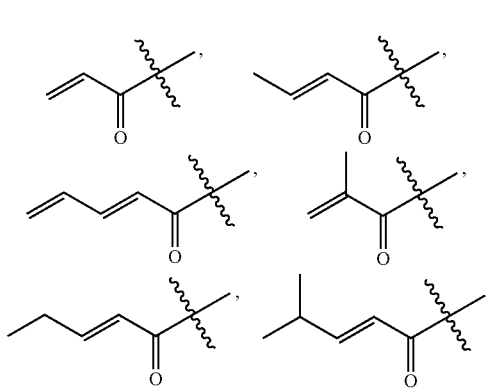

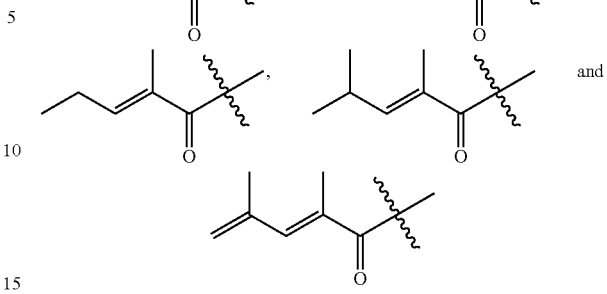

Preferably, $R^1$ is selected from a 2-methoxyaniline, 2-bromoaniline, 2-fluoroaniline, 2-chloroaniline, 3-methoxyaniline, 3-bromoaniline, 3-fluoroaniline, 3-chloroaniline, 3,5,difluoroaniline, 3,5,dichloroaniline, 3,5,dibromoaniline, 3-(trifluoromethyl)aniline, 4-chloro-3-(trifluoromethyl)aniline, 3-chloro-4-fluoroaniline, 4-fluoro-3-(trifluoromethyl)aniline, 4-fluoroaniline, 4-methoxyaniline, 4-bromoaniline, 4-chloroaniline, 4-isopropylaniline 3-bromo-5-(trifluoromethyl)aniline, bis(trifluoromethyl)aniline, 4-(tert-butyl) aniline or 1-napthylmethylamine moiety; and $R^3$ is represented by $OR^m$ or $NH(R^m)$ wherein $R^m$ is selected from the group consisting of:

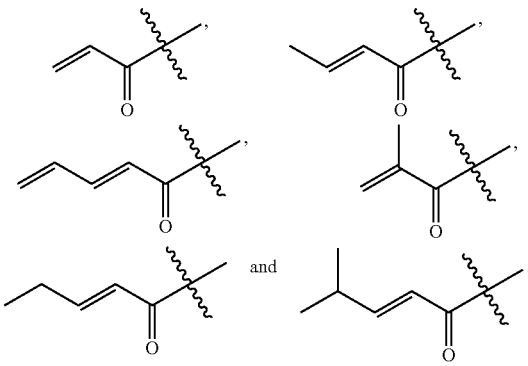

When $R^3$ is a Michael acceptor group, this group enables a covalent bond to be formed between a carbon atom of the Michael acceptor on the quinazoline based tyrosine-kinase inhibitor and a sulfur atom of a cysteine residue of a tyrosine kinase. This bonding can irreversibly attach the quinazoline based tyrosine-kinase inhibitor to the tyrosine kinase. This can result in the inactivation of the tyrosine kinase.

The quinazoline-based tyrosine kinase inhibitor may be conjugated (e.g. via a covalent bond or a linker) to the beacon through the substituents at $R^1$, $R^2$ or $R^3$.

Natural Products

The theranostic systems of the present invention may comprise one or more natural products. The natural product may be a phytochemical natural product (i.e. plant-derived) or a marine-derived natural product. In an embodiment, the natural product is a marine-derived natural product or phytochemical natural product containing at least one aromatic ring and at least one hydroxyl group.

The natural product may be selected from the group including: (i) chromanols of the vitamin E superfamily (e.g. α, β, γ, δ tocopherols and α, β, γ, δ tocotrienols), and precursors, analogues and derivatives thereof; (ii) poly(oxo)phenolic compounds (such as tannins, gallic acid, catechols and epicatechin), and analogues and derivatives thereof; (iii) retinoids, and analogues and derivatives thereof; (iv) resveratrol, and precursors, analogues and derivatives thereof; (v) flavonoids; and (vi) terpenes and terpenoids.

The natural product or phytochemical natural product may contain one or more aromatic rings and one or more hydroxyl groups. For example, the natural product may be a chromanol of the vitamin E superfamily, which includes, but is not limited to, α, β, γ, δ-tocopherols and α, β, γ, δ-tocotrienols and precursors, analogues and derivatives thereof. The structures of α, β, γ, δ-tocopherol and α, β, γ, δ-tocotrienol are presented below.

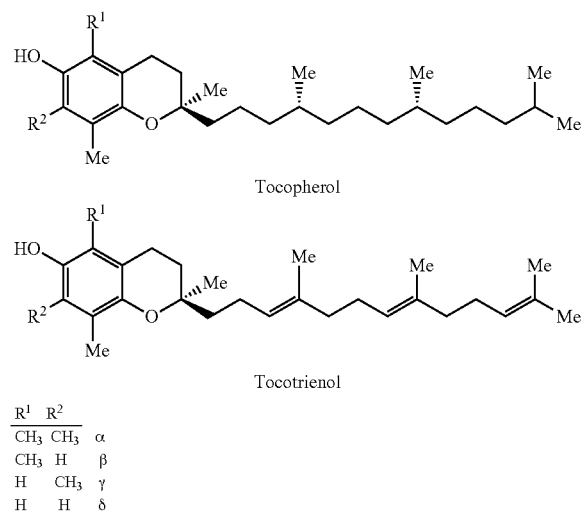

In an embodiment, the phytochemical natural product is a poly(oxo)phenolic compound.

In an embodiment, the phytochemical natural product is a retinoid. Examples include, first generation retinoids such as retinol, tretinoin, isotretinoin and alitretinoin, second generation retinoids such as acitretin, and third generation retinoids such as adapalene and bexatorene.

In an embodiment, the phytochemical natural product is selected from resveratrol and analogues and derivatives thereof.

The response to the targeted inhibition of cancers just using a combination or complex of the quinazoline-based tyrosine kinase inhibitors and the beacon may be insufficient due to intrinsic or acquired molecular mechanisms leading to the resistance to kinase inhibition. In these instances, it may be useful to incorporate a natural product into the theranostic system as an additional therapeutic agent. The natural product may have (tyrosine kinase) signal modulating properties which potentiate or sensitise the cancer cells to the combination or complex of the quinazoline-based tyrosine kinase inhibitors and the beacon. The inclusion of a natural product with signal-modulating properties in the therapeutic systems of the present invention may increase the anti-cancer properties of the systems by (i) amplifying their signal modulating potential, (ii) facilitating delivery to the required sub-cellular target organelle (e.g. mitochondria with phosphoEGFR) or (iii) enabling monitoring of the interference with the receptor binding and signal transduction attributes.

Various preferred embodiments of the first aspect of the present invention will now be described in detail.

Embodiment 1

In this embodiment of the present invention, the theranostic system comprises an anilinoquinazoline of Formula II in combination with a beacon as defined herein (i.e. B+anilinoquinazoline).

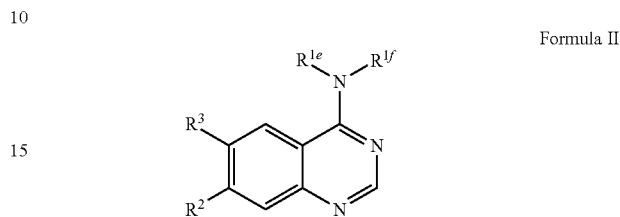

Formula II

In aspects of this embodiment, the theranostic systems may further comprise a natural product as already defined herein. The natural product may be complexed to the beacon (i.e. [B-NatP]), or the natural product may be free (i.e. it is not complexed to any of the other components in the theranostic system).

In the anilinoquinazoline of Formula II each $R^{1e}$, $R^{1f}$, $R^2$ and $R^3$ are as already defined herein.

Preferably, $R^{1e}$ is represented by a hydrogen atom and $R^{1f}$ is represented by an optionally substituted aryl or aralkyl group. Preferably, $R^{1f}$ is

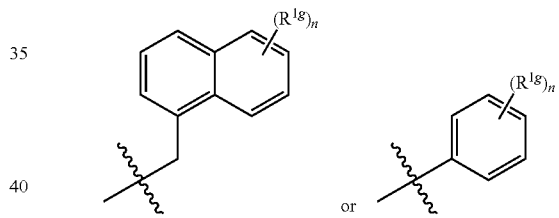

wherein n is 0 to 4, and each $R^{1g}$ independently represents a hydrogen atom, a halogen, $NO_2$, $CN$, $N_3$, or an optionally substituted alkyl, alkenyl, alkynyl, alkoxy, acyl, cycloalkyl, cycloalkenyl, aryl, aralkyl, heterocyclyl or heterocyclylalkyl group.

More preferably, $R^{1f}$ is represented by a aromatic group selected from

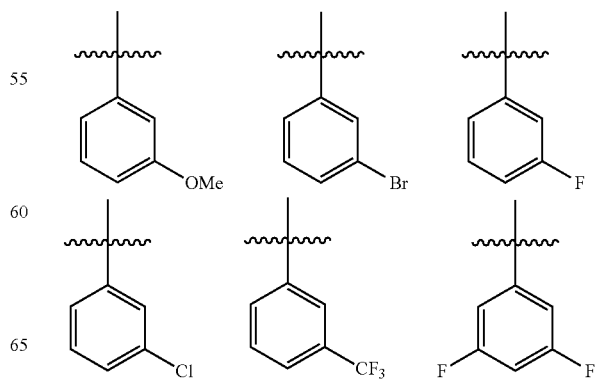

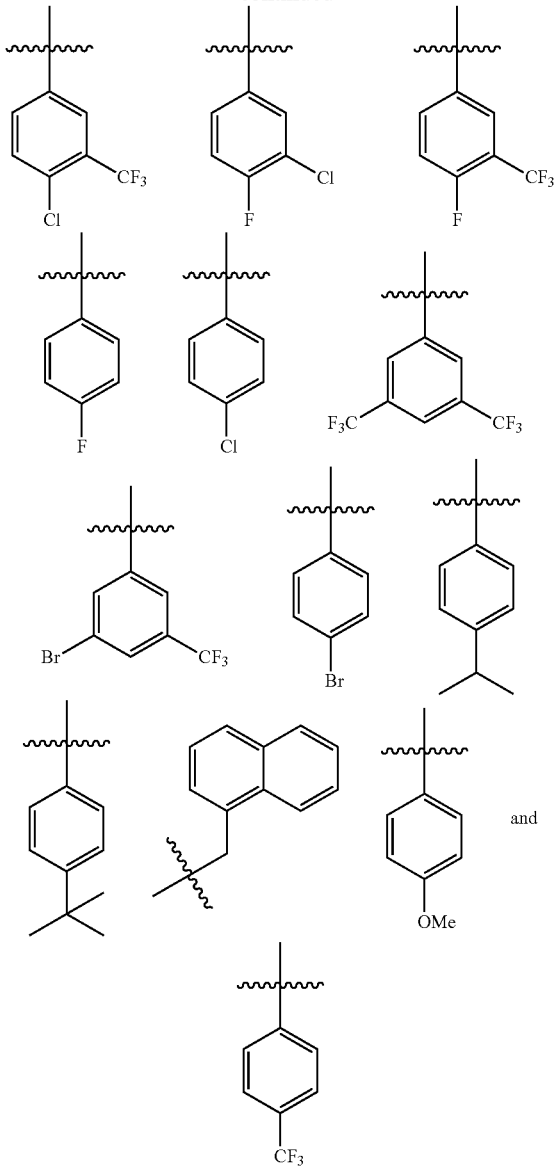

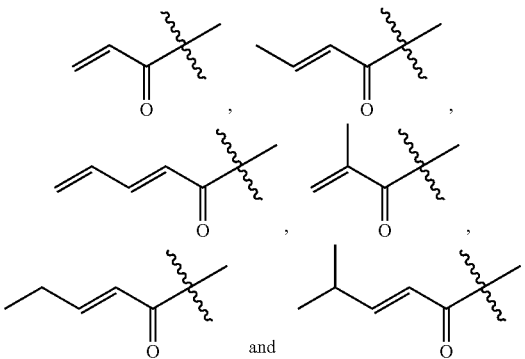

The anilinoquinazoline of Formula II may have the structure of Formula IIa.

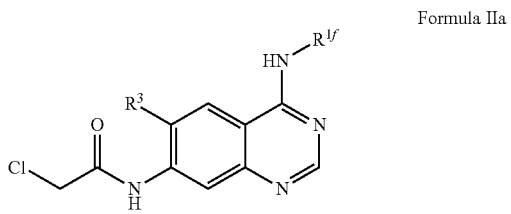

Formula IIa

In Formula IIa, $R^{1f}$ and $R^3$ are as already defined herein. In a preferred aspect of this embodiment, the anilinoquinazoline may be selected from the group consisting of:

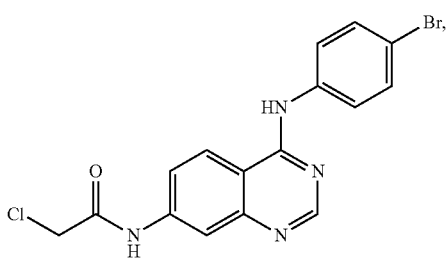

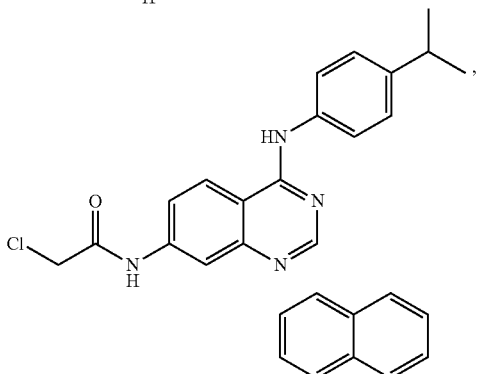

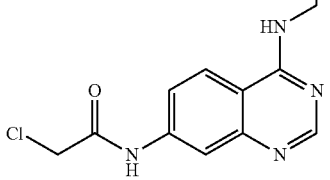

and

The aniline moiety at the C-4 position of the quinazoline ring can be recognized by the gatekeeper residue of a tyrosine kinase and improves the kinase-inhibiting therapeutic) activity of the quinazoline.

Preferably, $R^2$ is represented by a hydrogen atom, OMe, $NO_2$, $NH_2$, CN, —NHC(=O)$CH_2$Cl, —SC(=O)$CH_2$Cl, —OC(=O)$CH_2$Cl, —NHC(=O)$CH_2$Br, —SC(=O)$CH_2$Br, —OC(=O)$CH_2$Br, —NHC(=O)$CH_2$F, —SC(=O)$CH_2$F, or —OC(=O)$CH_2$F. Preferably, $R^2$ is —NHC(=O)$CH_2$Cl, —SC(=O)$CH_2$Cl or —OC(=O)$CH_2$Cl. More preferably $R^2$ is H, —NHC(=O)$CH_2$Cl, —SC(=O)$CH_2$Cl or —OC(=O)$CH_2$Cl. Even more preferably $R^2$ is —NHC(=O)$CH_2$Cl.

Preferably, $R^3$ is represented by a hydrogen atom, $NO_2$, CN, $N_3$, OR''' or NHR''', wherein R''' is an acroyl, crotonoyl, pentenoyl, pentadienoyl, —C(=O)Me, —C(=O)$^t$Bu or —C(=O)$CF_3$ group.

More preferably, $R^3$ is NHR''', wherein R''' is selected from the group consisting of:

-continued

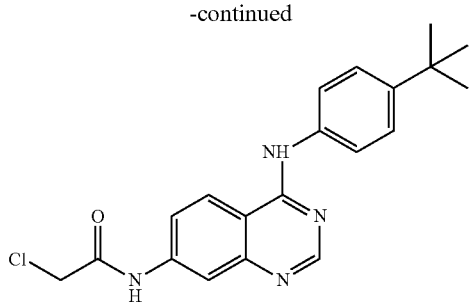

The anilinoquinazolines of Formula IIa (when $R^3$ is represented by a hydrogen atom) may be synthesised via the following reaction scheme.

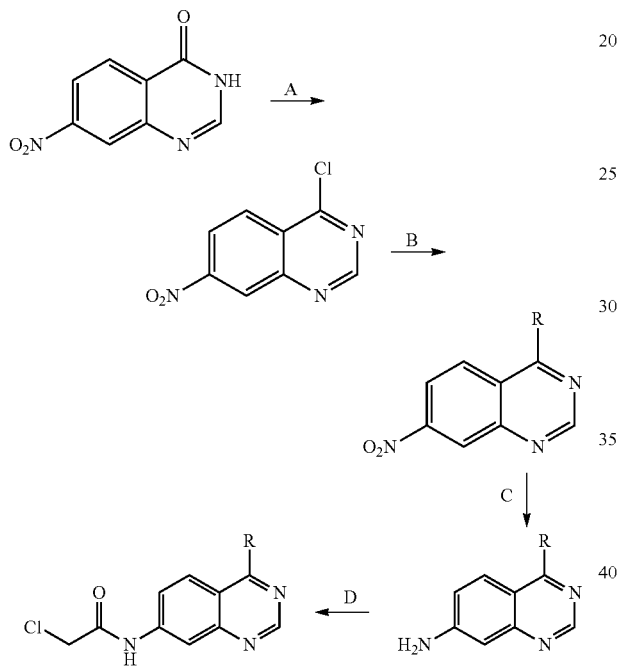

A) Thionyl chloride, DMF, 3 h at 110° C. B) aniline or naphthalen-1-ylmethanamine, isopropanol. C) EtOH, Acetic Acid, water, Fe granules 7 h at 80° C. D) Et$_3$N, chloroacetylchloride In the above reaction scheme, the aniline may be selected from the group consisting of 2-methoxyaniline, 2-bromoaniline, 2-fluoroaniline, 2-chloroaniline, 3-methoxyaniline, 3-bromoaniline, 3-fluoroaniline, 3-chloroaniline, 3,5,difluoroaniline, 3,5,dichloroaniline, 3,5,dibromoaniline, 3-(trifluoromethyl)aniline, 4-chloro-3-(trifluoromethyl)aniline, 3-chloro-4-fluoroaniline, 4-fluoro-3-(trifluoromethyl)aniline, 4-fluoroaniline, 4-methoxyaniline, 4-bromoaniline, 4-chloroaniline, 4-isopropylaniline 3-bromo-5-(trifluoromethyl)aniline, bis(trifluoromethyl)aniline and 4-(tert-butyl)aniline.

Anilinoquinazoline molecules with functionality (such as a Michael acceptor group) at the C6 position of the anilinoquinazoline ring can be accessed using synthetic procedures familiar to one skilled in the art (see e.g. J. Med. Chem., 43 (2000) 1380-1397).

As well as serving as a component of the theranostic systems of this embodiment, the free anilinoquinazolines have shown significant antiproliferative properties in EGFR+ve cell systems and tumors. Accordingly, it is considered that these compounds can serve as future candidates for preclinical and clinical application.

Embodiment 2

In this embodiment of the present invention, the theranostic system comprises a complex of an anilinoquinazoline-based tyrosine kinase inhibitor, (also referred to herein as Tyrosine Kinase Inhibiting Factor (TKIF)) and the beacon as already defined herein. This complex can be depicted in shorthand as [anilinoquinazoline-B]. Preferably, the anilinoquinazoline is complexed to the beacon through a flexible linker or bridge.

In aspects of this embodiment, the theranostic system may further comprise a natural product as already defined herein in combination with the [anilinoquinazoline-B] complex. These theranostic systems can be depicted in short hand as NatP+[anilinoquinazoline-B]. In other words, the theranostic system may be a combination of a [anilinoquinazoline-B] complex and a free natural product. Combining the complex with a free natural product with signal-modulating properties may either sensitize resistant tumors to the kinase inhibiting action of the anilinoquinazoline or offer synergistic and/or additive effects, thus optimizing the therapeutic attributes and minimizing the required dose of the therapeutic agents.

Aspect A of Embodiment 2

One aspect of Embodiment 2 is defined by Formula III below:

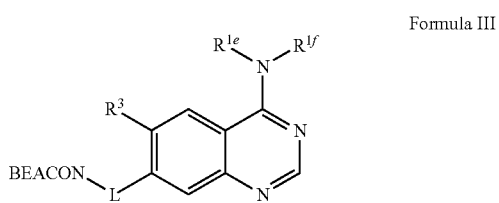

Formula III wherein:

$R^{1e}$, $R^{1f}$ and $R^3$ are as already defined herein;

L is a linker selected from the group consisting of (i) a poly(ethylene glycol) linker, (ii) a $C_1$-$C_{20}$ (e.g. $C_1$-$C_{10}$) aliphatic chain; and (iii) a conjugate of a poly(ethylene glycol) linker with a $C_1$-$C_{20}$ (e.g. $C_1$-$C_{10}$) aliphatic chain, wherein the poly(ethylene glycol) linker and the $C_1$-$C_{20}$ aliphatic chain are conjugated via a peptidic or esteric bond; and Beacon is as already defined herein.

In the aspect of Embodiment 2 defined by Formula III, the beacon is conjugated to the anilinoquinazoline away from the tyrosine kinase-binding site.

Preferably, in this aspect of Embodiment 2, $R^{1e}$ is a hydrogen atom and $R^{1f}$ is selected from a 2-methoxyphenyl, 2-bromophenyl, 2-fluorophenyl, 2-chlorophenyl, 3-methoxyphenyl, 3-bromophenyl, 3-fluorophenyl, 3-chlorophenyl, 3, 5,difluorophenyl, 3,5-dichlorophenyl, 3,5,dibromophenyl, 3-(trifluoromethyl) phenyl, 4-chloro-3-(trifluoromethyl) phenyl, 3-chloro-4-fluorophenyl, 4-fluoro-3-(trifluoromethyl) phenyl, 4-fluorophenyl, 4-methoxyphenyl, 4-bromoaniline, 4-chlorophenyl, 4-isopropylphenyl 3-bromo-5-(trifluoromethyl)phenyl, bis(trifluoromethyl) phenyl, 4-(tert-butyl) phenyl or 1-napthylmethyl moiety.

The beacon may be a fluorophore emitting in the NIR wavelength region. For example, the beacon may be a fluorophore emitting in the NIR wavelength region selected from the group consisting of carbocyanine, oxocarbocyanine, macrocyanine, indocarbocyanine, fluorescein, polymethine, rhodamine, xanthene, Cy®5, Cy5.5®, Cy, ViVoTag®-660, 680 and 750; AlexaFluor® 660, 680, 700, 750, 790; Dy-677, 780; Dylight 680; HiLyte™Fluor 680, 750; IRDye 800CW, 700DX and ADS 780WS, 830WS, 832WS. When the beacon is a fluorophore emitting in the NIR wavelength region, the beacon is preferably a cyanine derivative. Cyanine derivatives are preferred due to their high extinction coefficients, high fluorescent yield in hydrophobic environments and high Signal to Noise Ratio (SNR), enabling deep penetration in tissues. More preferably, the beacon is a heptacyanine dye. Even more preferably, the heptacyanine dye is

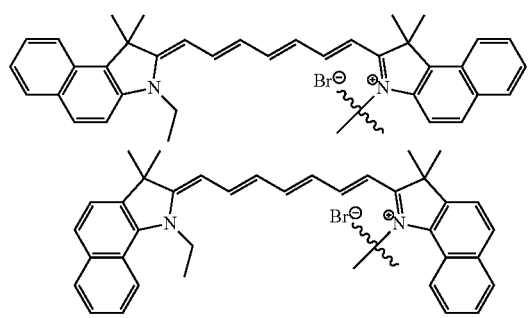

or

The linker, L, may preferably be selected from the group consisting of tetra(ethylene glycol) (TEG), hexa(ethylene glycol) (HEG), a $C_5$ aliphatic chain, and a conjugate of a TEG with the $C_5$ aliphatic chain, wherein the TEG linker and the $C_5$ aliphatic chain are conjugated via a peptidic or esteric bond.

In an embodiment, L may be a bond. In other words, the beacon is directly bonded to the anilinoquinazoline.

Examples of compounds according to Formula III are provided below:

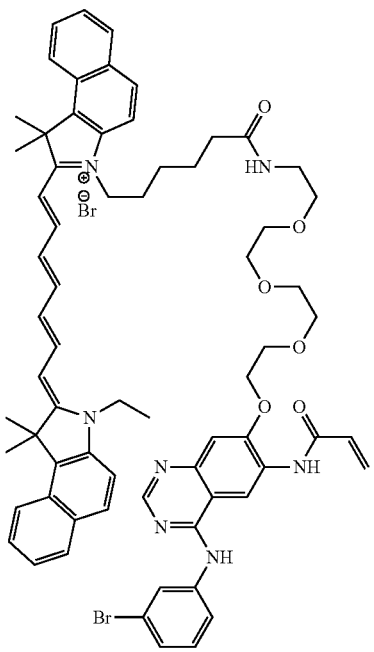

-continued

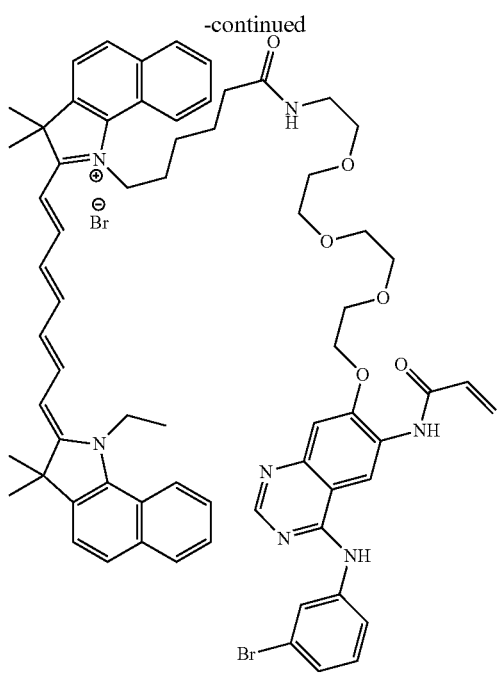

The structures above are comprised of five moieties: a) a cyanine dye which has been selected for its biological compatibility and NIR emission; b) a Michael Acceptor (enabling formation of a new bond between the β-carbon atom of the acrylamide Michael acceptor on the anilinoquinazoline tyrosine-kinase inhibitor and the γ-sulfur atom of a Cysteine of the tyrosine kinase upon their interaction), thus assuring a target recognizing attribute; c) a C4 aniline which has the suitable size and orientation in order to be recognized by the gatekeeper and achieve maximum kinase-inhibiting (i.e. therapeutic) activity, d) a quinazoline moiety which is combined with cyanine and gives an optical (i.e. imaging) attribute, and e) a tetra(ethylene glycol) (TEG) bridge which keeps the backbone dye core further away from the hinge region. The 6-acrylamido-4-anilinoquinazoline portion of the molecule is tethered to a cyanine fluorophore at C-7 via a TEG (tetraethylene glycol) linker.

Aspect B of Embodiment 2

Another aspect of Embodiment 2 is defined by Formula IV below

Formula IV

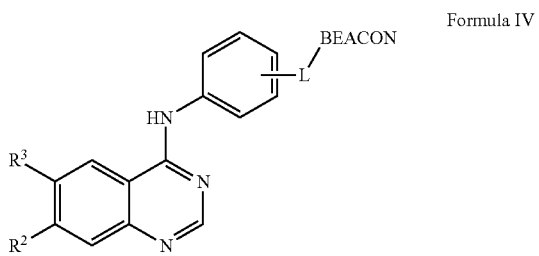

wherein:

$R^2$ and $R^3$ are as already defined herein;

L is a linker selected from the group consisting of (i) a poly(ethylene glycol) linker, (ii) a $C_1$-$C_{20}$ (e.g. $C_1$-$C_{10}$) aliphatic chain; and (iii) a conjugate of a poly(ethylene glycol) linker with a $C_1$-$C_{20}$ (e.g. $C_1$-$C_{10}$) aliphatic chain, wherein the poly(ethylene glycol) linker and the $C_1$-$C_{20}$ aliphatic chain are conjugated via a peptidic or esteric bond; and Beacon is as defined herein.

In this aspect of Embodiment 2 defined by Formula IV, the beacon is conjugated to the anilinoquinazoline in proximity to the tyrosine kinase-binding site.

The beacon may be a fluorophore emitting in the NIR wavelength region. For example, the beacon may be a fluorophore emitting in the NIR wavelength region selected from the group consisting of carbocyanine, oxocarbocyanine, macrocyanine, indocarbocyanine, fluorescein, polymethine, rhodamine, xanthene, Cy®5, Cy5.5®, Cy, ViVoTag®-660, 680 and 750; AlexaFluor® 660, 680, 700, 750, 790; Dy-677, 780; Dylight 680; HiLyte™Fluor 680, 750; IRDye 800CW, 700DX and ADS 780WS, 830WS, 832WS. When the beacon is a fluorophore emitting in the NIR wavelength region, the beacon is preferably a cyanine derivative. Cyanine derivatives are preferred due to their high extinction coefficients, high fluorescent yield in hydrophobic environments and high Signal to Noise Ratio (SNR), enabling deep penetration in tissues. More preferably, the beacon is a heptacyanine dye. Even more preferably, the heptacyanine dye is

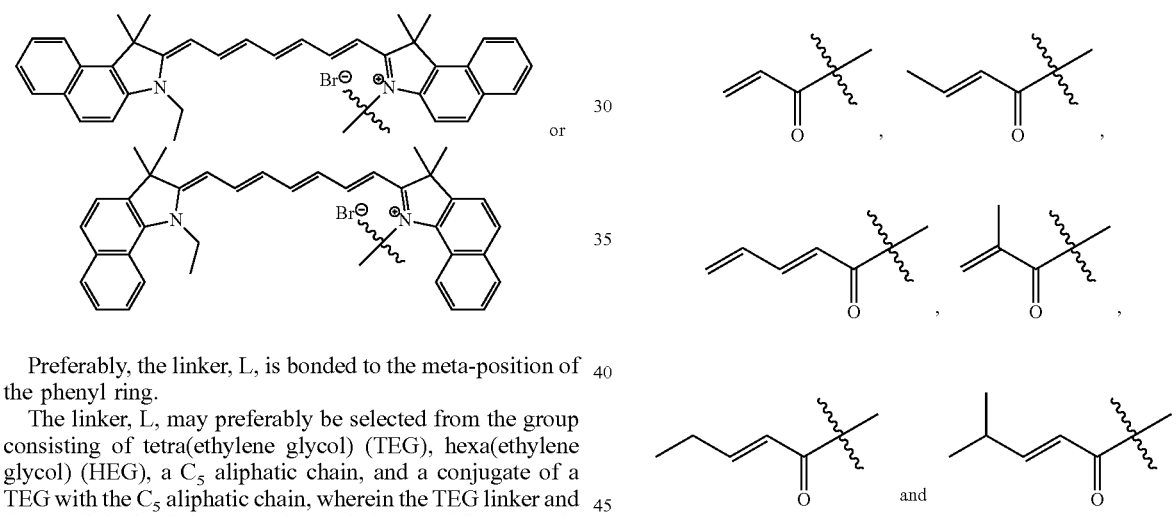

or

Preferably, the linker, L, is bonded to the meta-position of the phenyl ring.

The linker, L, may preferably be selected from the group consisting of tetra(ethylene glycol) (TEG), hexa(ethylene glycol) (HEG), a $C_5$ aliphatic chain, and a conjugate of a TEG with the $C_5$ aliphatic chain, wherein the TEG linker and the $C_5$ aliphatic chain are conjugated via a peptidic or esteric bond.

In an embodiment, L may be a bond. In other words, the beacon is directly bonded to the anilinoquinazoline.

Examples of compounds according to Formula IV are provided below:

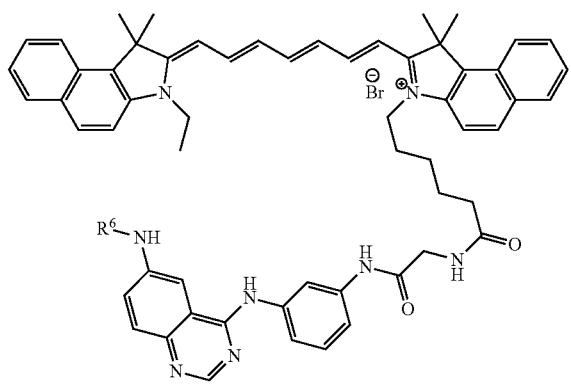

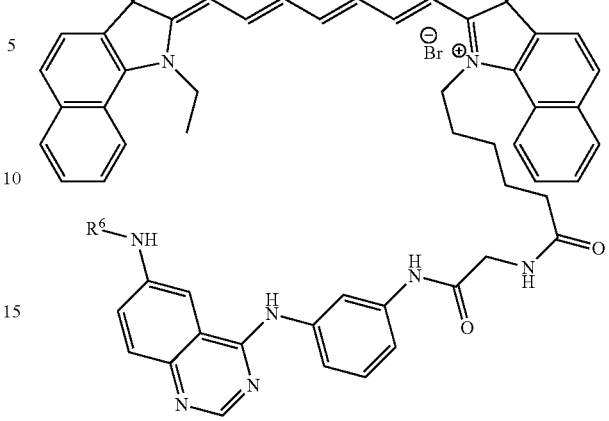

Preferably, $R^6$ is represented by a hydrogen atom, or an acroyl, crotonoyl, pentenoyl, pentadienoyl, —C(=O)Me, —C(=O)$^t$Bu or —C(=O)CF$_3$ group. More preferably, $R^6$ is selected from the group consisting of:

Aspect C of Embodiment 2

Despite their favourable properties in term of sensing properties and drug delivery efficacies, the plethora of nanosized systems reported so far have not received regulatory approval (with the exception of a few examples in the polymeric and liposomal sub-group). This is mostly because of unfavourable toxicities attributed to their metallic cores. Further, metal-based nanoparticles exhibit difficulties and lack of robustness in their grafting with organic therapeutic and targeting tags. The organometallic complexes described below have favourable pharmacokinetics and are of high promise for clinical use.

In this aspect of Embodiment 2, the anilinoquinazoline-based tyrosine kinase inhibitor is complexed to a heterometallic multimodal compound/scaffold including: (1) a functionalised macrocyclic trivalent lanthanide complex; and (2) a poly-pyridyl near infra-red emitter transition metal complex. The complex may be represented by the Formula B:

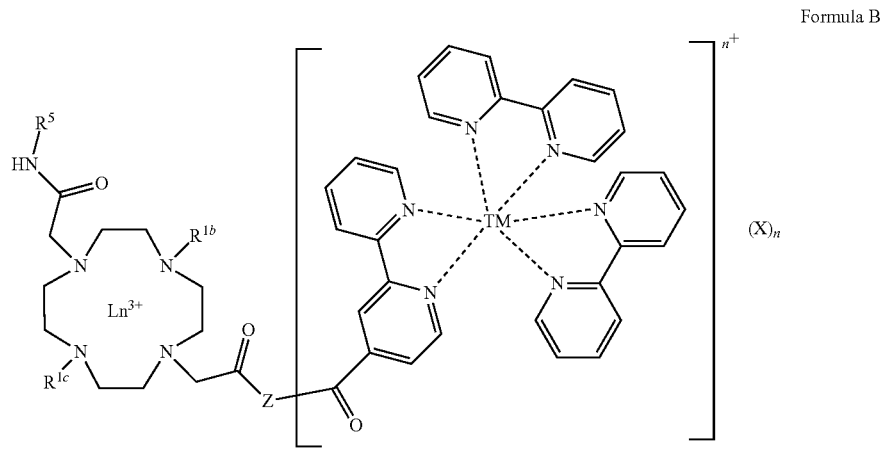

Formula B wherein
$R^{1b}$ and $R^{1c}$ are each independently, a hydrogen atom, —$(CH_2)_mP(=O)(OH)_2$, or —$(CH_2)_mC(=O)OH$, wherein m is 1, 2, 3, 4 or 5 (preferably, m is 1);

$Ln^{3+}$ is a trivalent lanthanide metal selected from the group consisting of La(III), Ce(III), Pr(III), Nd(III), Sm(III), Eu(III), Gd(III), Tb(III), Dy(III), Ho(III), Er(III), Tm(III), Yb(III) and Lu(III)) (preferably, $Ln^{3+}$ is Gd(III));

TM is a transition metal selected from the group consisting of: ruthenium, rhenium and iridium;

n is 2;

X is a counterion (optionally selected from the groups consisting of $PF_6$ and $ClO_4$);

Z is represented by O, NH, S, a poly(ethylene glycol) linker (e.g. TEG or HEG), a $C_1$-$C_{20}$ aliphatic chain (e.g. $C_1$-$C_{10}$, preferably $C_5$) or a conjugate of a poly(ethylene glycol) linker with a $C_1$-$C_{20}$ aliphatic chain, wherein the poly(ethylene glycol) linker and the $C_1$-$C_{20}$ aliphatic chain are conjugated via a peptidic or esteric bond; and $R^5$ is

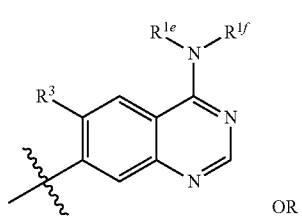

OR

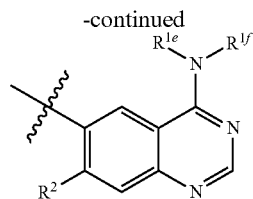

wherein, $R^{1e}$ $R^{1f}$, $R^2$ and $R^3$ are as already defined herein.

In this aspect of Embodiment 2, the beacon (B) is "multimodal" and can be detected by optical and/or magnetic and/or radiofrequency imaging. The organometallic structures of this aspect of Embodiment 2 are promising solutions for combined optical and magnetic or optical and radiofrequency imaging clinical applications. Favorable magnetic properties are disclosed by vibrating sample magnetometry and suitability for MRI imaging is documented with relaxometry. Gadolinium, already well-documented for its MRI imaging suitability replacing iron-containing contrast agents, also has favourable radiofrequency imaging properties. Radiofrequency imaging with microwave radiation is an emerging technology comprising an extremely favourable method for screening of cancer because it carries lower energy compared to X-rays, thus being safe, non-ionizing and without side effects for the human body (Nikolova N. K., IEEE Microwave Magazine, December 2011). These features allow frequent patient screening which is especially important when monitoring younger individuals. Furthermore, the ability to combine radiofrequency imaging with anti-EGFR targeting is expected to be of high clinical value for lung cancer screening and monitoring, where current screening solutions have considerable shortcomings.

A typical synthetic strategy to the complexes of this aspect of Embodiment 2 (when Z is O) is depicted below.

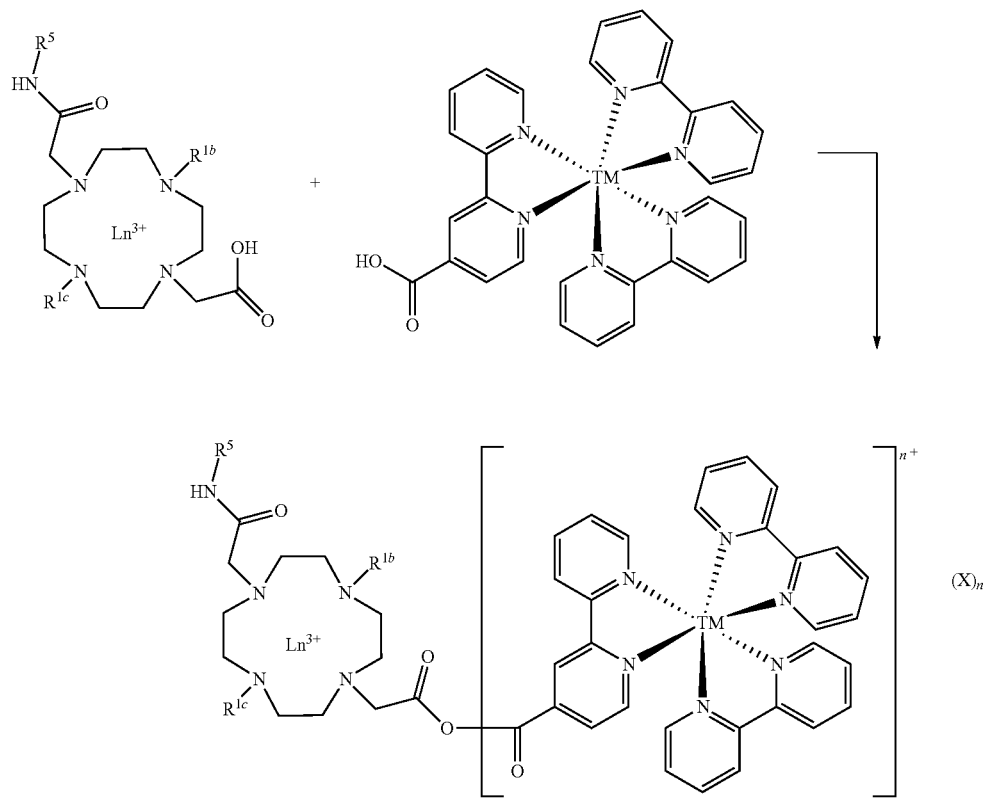

The functionalised macrocyclic lanthanide complex and the poly-pyridyl near infra-red emitter transition metal complex can be coupled by refluxing in an alcoholic solvent (e.g. methanol or ethanol) in the presence of a base (e.g. NaHCO$_3$).

The complex of the anilinoquinazoline-based tyrosine kinase inhibitor and the hetero-metallic multimodal compound/scaffold may be represented by Formula C.

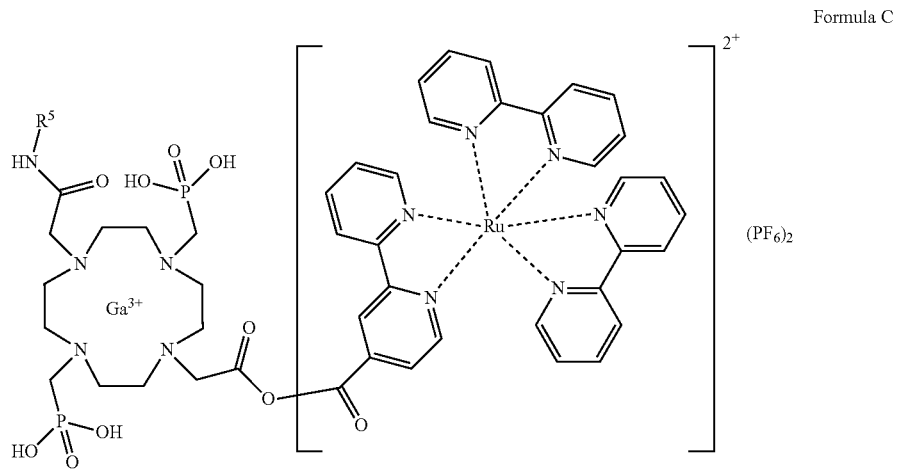

Formula C

Wherein R$^5$ is defined as above.

Examples of compounds according to Formula C are provided below:
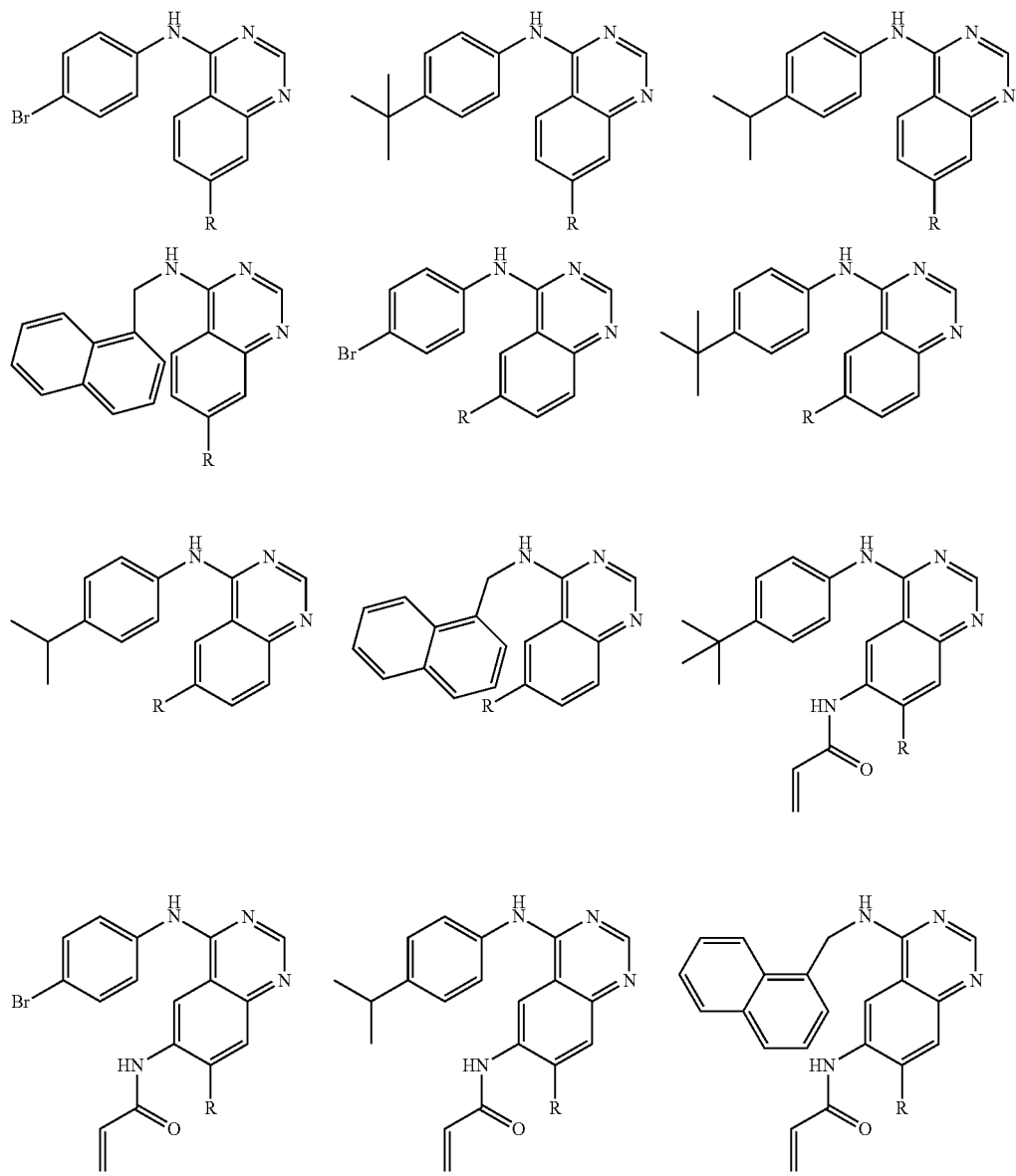
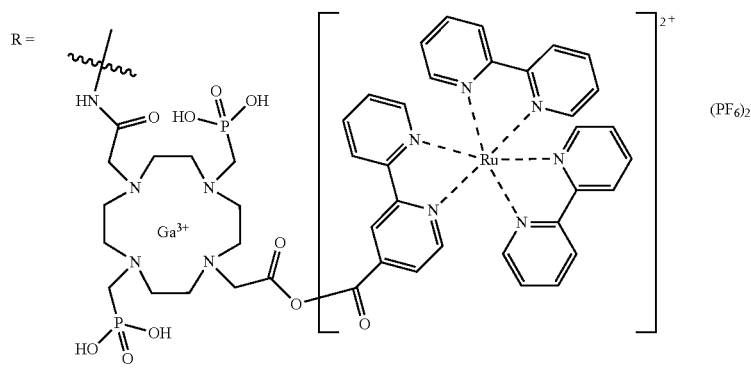

Aspect D of Embodiment 2

Another aspect of Embodiment 2 is defined by Formulae Fa and Fb.

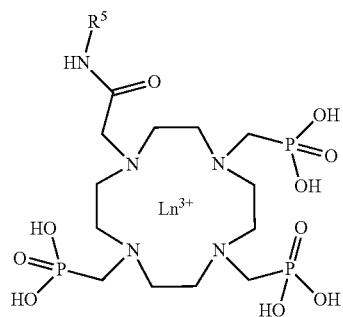

Formula Fa

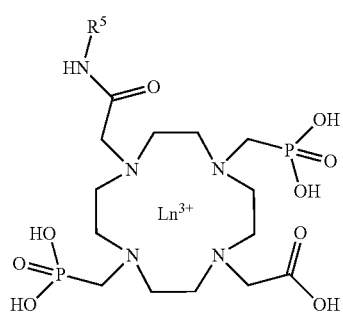

Formula Fb

In formulae Fa and Fb, $R^5$ and $Ln^{3+}$ are as already defined herein. Preferably, $Ln^{3+}$ is $Gd^{3+}$.

Aspect E of Embodiment 2

Another aspect of Embodiment 2 can be represented by the formula [Anilinoquinazoline]$_3$Ln$^{3+}$·2H$_2$O, wherein the anilinoquinazoline is as defined herein by Formula II and $Ln^{3+}$ is as defined herein. An example of this aspect is depicted below.

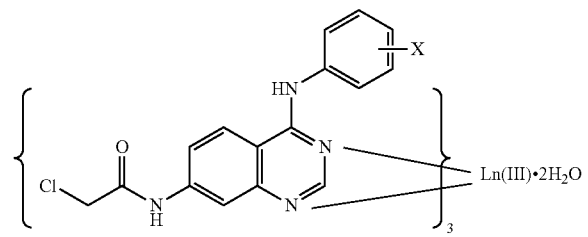

Embodiment 3

In this embodiment of the present invention, the theranostic system comprises a natural product as already defined herein in combination with a beacon as already defined herein (i.e. B+NatP).

In aspects of this embodiment, the theranostic systems may further comprise a quinazoline or anilinoquinazoline-based tyrosine kinase inhibitor as already defined herein. The quinazoline or anilinoquinazoline-based tyrosine kinase inhibitor may be complexed to the beacon (i.e. [B-quinazoline] or [B-anilinoquinazoline), or the quinazoline or anilinoquinazoline-based tyrosine kinase inhibitor may be free (i.e. it is not complexed to any of the other components in the theranostic system).

Embodiment 4

In this embodiment of the present invention, the theranostic system comprises a complex of the natural product (also referred to herein as NatP) and the beacon as defined herein. This complex can be depicted in shorthand as [NatP-B]. The natural product may be may be selected from the group including: (i) chromanols of the vitamin E superfamily (e.g. α, β, γ, δ Tocopherols and α, β, γ, δ Tocotrienols), and precursors, analogues and derivatives thereof; (ii) poly(oxo)phenolic compounds (such as tannins, gallic acid, catechols and epicatechin), and analogues and derivatives thereof; (iii) retinoids, and analogues and derivatives thereof; (iv) resveratrol, and precursors, analogues and derivatives thereof; (v) flavonoids; and (vi) terpenes and terpenoids.

The natural product may be complexed with the beacon via an ester bond, with an —OH group from the natural product forming this linkage. The ester bond may cleavable under physiological conditions. When the beacon is a fluorescent beacon, covalent binding through the OH-group in such a cleavable bond gives the natural product-based theranostic system functionalities of tunable fluorescence. This tunable fluorescence can allow for deciphering of the role of phytochemical natural products in the overall in vivo management of tyrosine-kinase mediated malignancies when complexed in theranostic systems.

Aspect A of Embodiment 4

An aspect of Embodiment 4 is defined by Formula G.

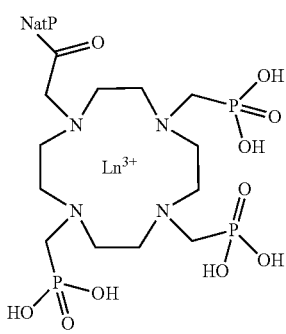

Formula G

In Formula G, $Ln^{3+}$ is as already defined herein and NatP is any natural product as already defined herein. Preferably, the natural product is linked to the beacon via an ester bond. Preferably, $Ln^{3+}$ is Gd.

NatP may be represented by a natural product selected from the group consisting of: (i) chromanols of the vitamin E superfamily (e.g. α, β, γ, δ tocopherols and α, β, γ, δ tocotrienols), and precursors, analogues and derivatives thereof; (ii) poly(oxo)phenolic compounds (such as tannins, gallic acid, catechols and epicatechin), and analogues and derivatives thereof; (iii) retinoids, their analogues and their derivatives; (iv) resveratrol, its precursors, analogues and derivatives; (v) flavonoids; and (vi) terpenes and terpenoids.

Preferably, NatP is α, β, γ or δ tocopherol or α, β, γ or δ tocotrienol, and precursors, analogues and derivatives thereof.

Examples of compounds according to Formula G are provided below:

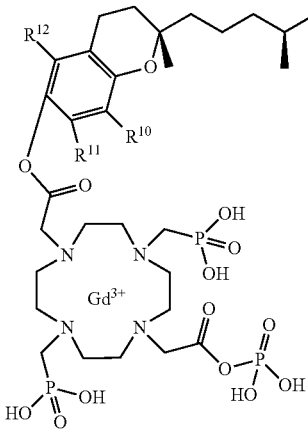

| R10 | R11 | R12 |
|-----|-----|-----|
| H   | H   | H   |
| Me  | H   | H   |
| H   | H   | Me  |
| H   | Me  | H   |
| Me  | OH  | Me  |
| Me  | OH  | H   |
| Me  | Me  | H   |
| Me  | Me  | Me  |
| Me  | H   | Me  |

Aspect B of Embodiment 4

Another aspect of Embodiment 4 is defined by Formula H.

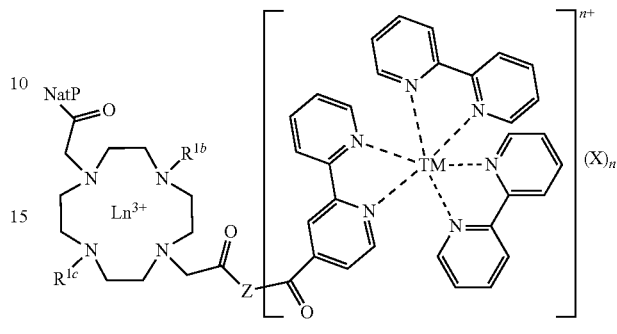

Formula H

In Formula H, NatP is a natural product as already defined herein and $R^{1b}$, $R^{1c}$, TM, X, Z and n are as already defined herein.

Preferably, the natural product is linked to the beacon via an ester bond. Preferably, $Ln^{3+}$ is Gd. Preferably, TM is Ru. Preferably X is $PF_6$. Preferably n is 2. Preferably, Z is O. Preferably, $R^{1b}$ and $R^{1c}$ are $-CH_2P(=O)(OH)_2$.

NatP may be represented by a natural product selected from the group consisting of: (i) chromanols of the vitamin E superfamily (e.g. α, β, γ, δ tocopherols and α, β, γ, δ tocotrienols), and precursors, analogues and derivatives thereof; (ii) poly(oxo)phenolic compounds (such as tannins, gallic acid, catechols and epicatechin), and analogues and derivatives thereof; (iii) retinoids, their analogues and their derivatives; (iv) resveratrol, its precursors, analogues and derivatives; (v) flavonoids; and (vi) terpenes and terpenoids. Preferably, NatP is α, β, γ or δ tocopherol or α, β, γ or δ tocotrienol, and precursors, analogues and derivatives thereof.

Examples of compounds according to Formula H are provided below.

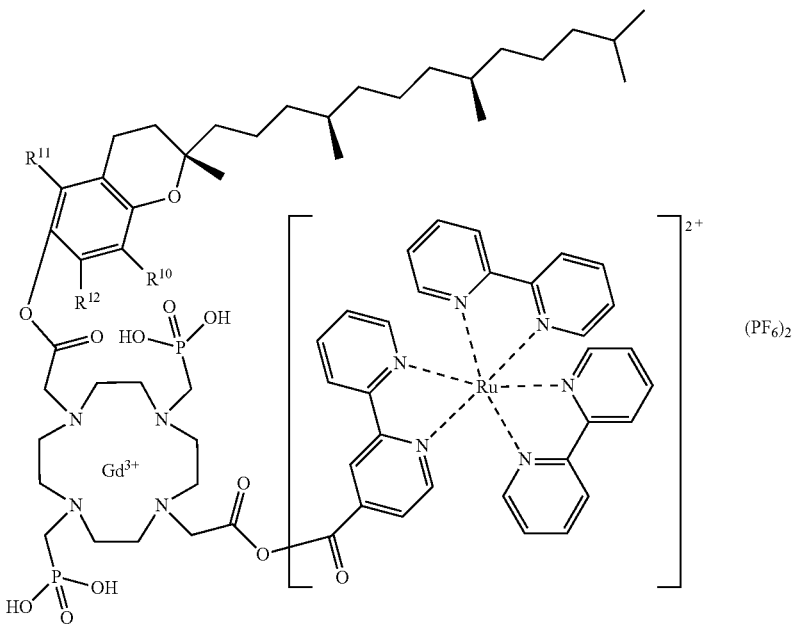

| $R^{10}$ | $R^{11}$ | $R^{12}$ |
|---|---|---|
| H | H | H |
| Me | H | H |
| H | Me | H |
| H | H | Me |
| Me | H | Me |
| H | Me | Me |
| Me | OH | H |
| Me | Me | H |
| OH | Me | H |
| OH | OH | H |
| Me | Me | Me |
| OH | Me | OH |
| OH | OH | OH |

Aspect C of Embodiment 4

In another aspect of embodiment 4, the complex of the natural product and the beacon has one of the following structures:

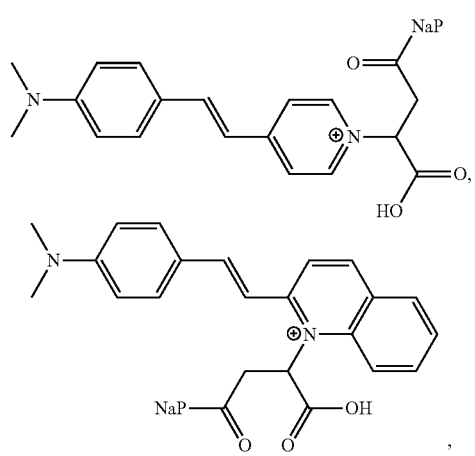

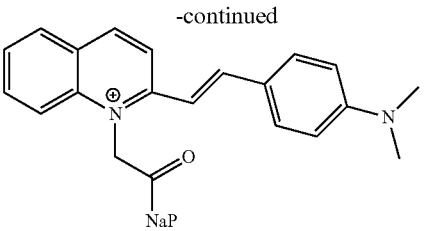

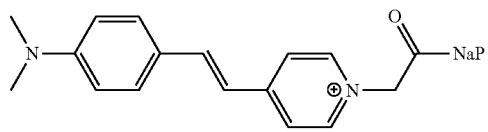

wherein NatP is a natural product as already defined herein. Preferably, the natural product is bonded to the beacon via a hydroxyl group. Examples of [B-NatP] complexes of this aspect of Embodiment 4 are as follows:

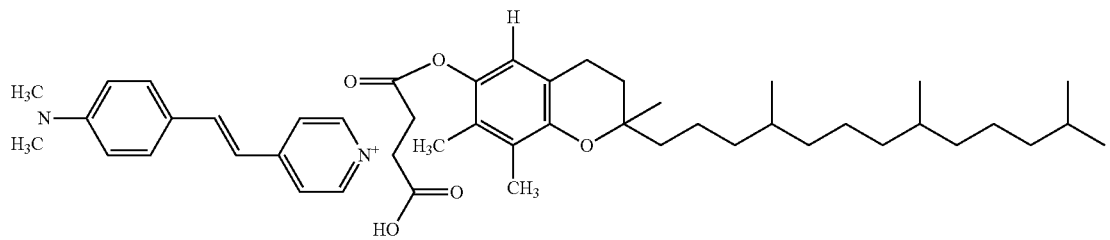

gamma-toc

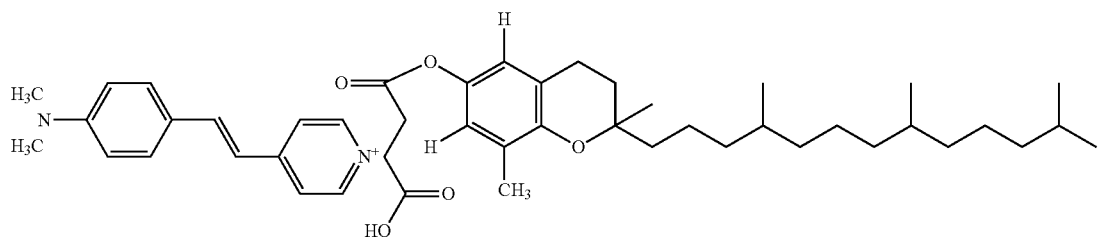

delta-toc

-continued
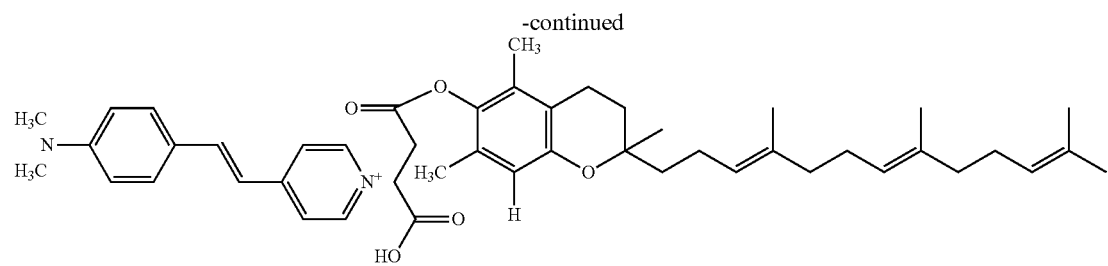
gamma-tocotrienol
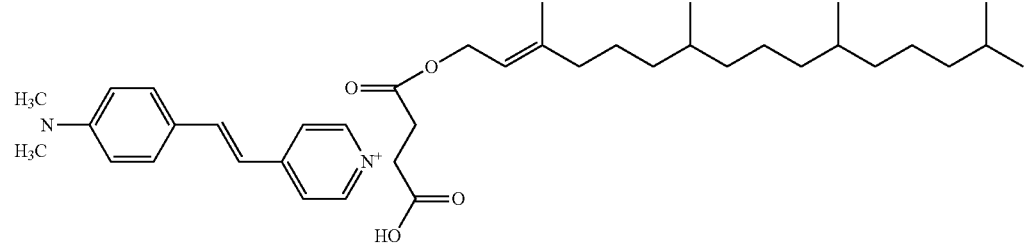
phytol
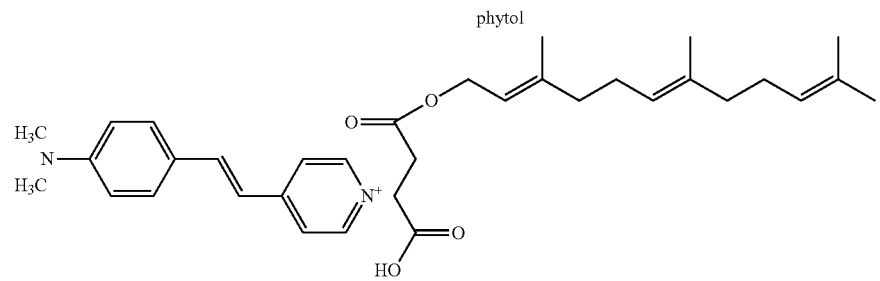
farnescol
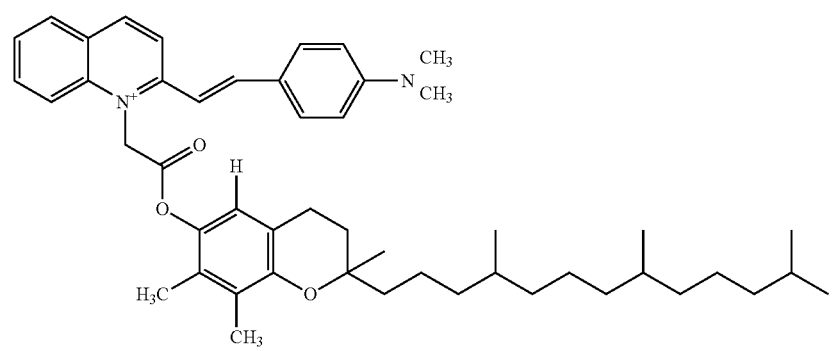
gamma-toc
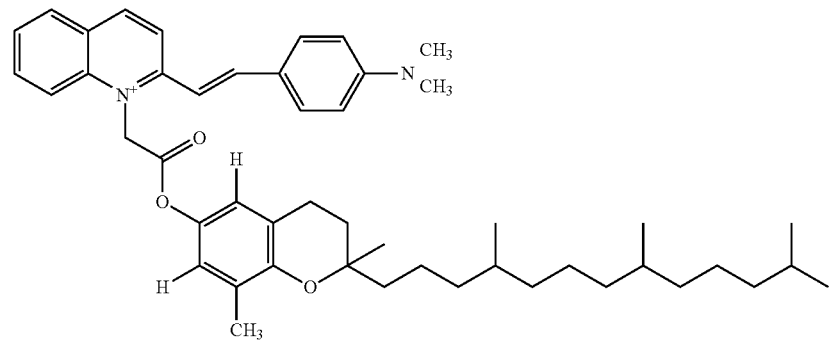
delta-toc

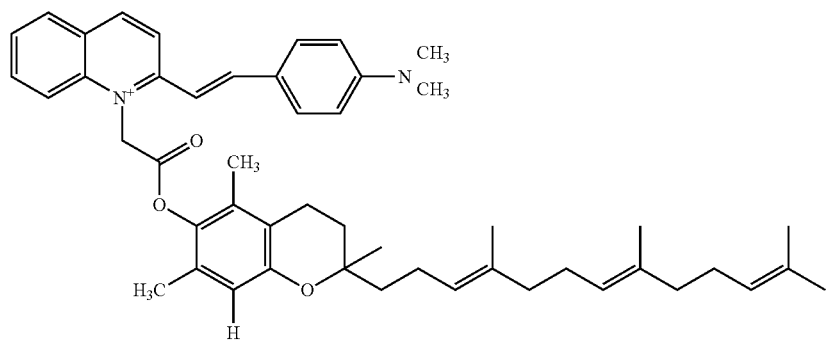
gamma-tocotrienol
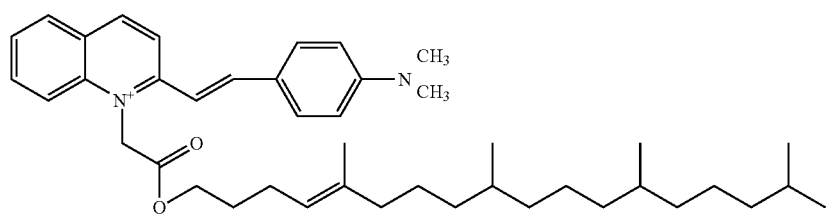
phytol
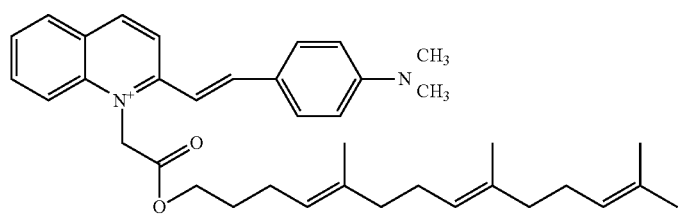
farnesol
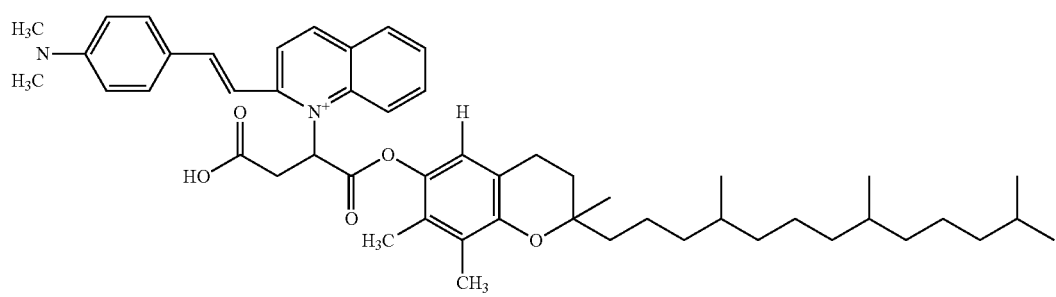
gamma-toc
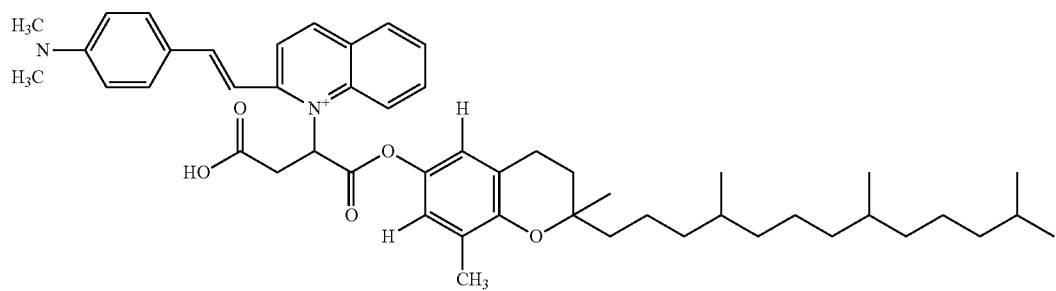
delta-toc

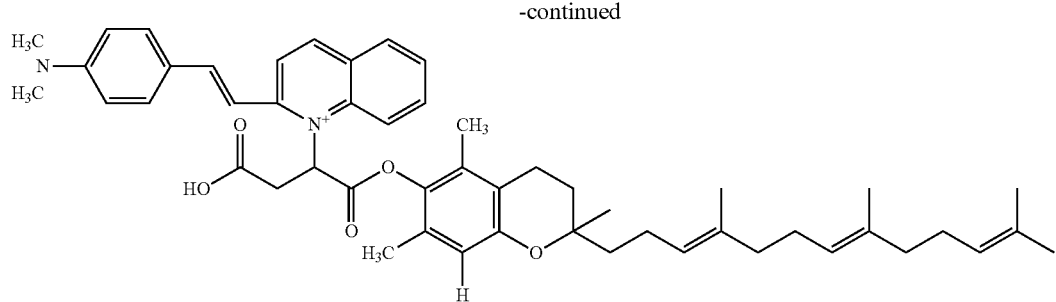
gamma-tocotrienol
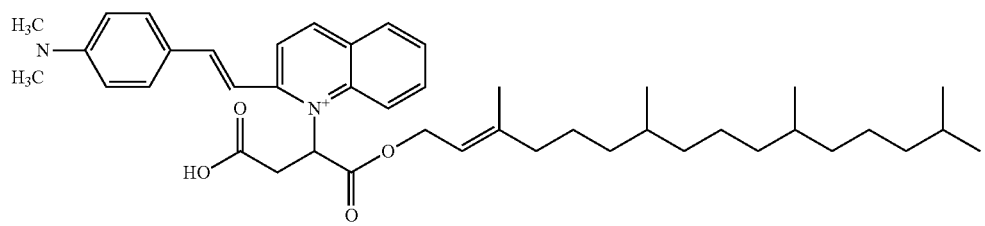
phytol
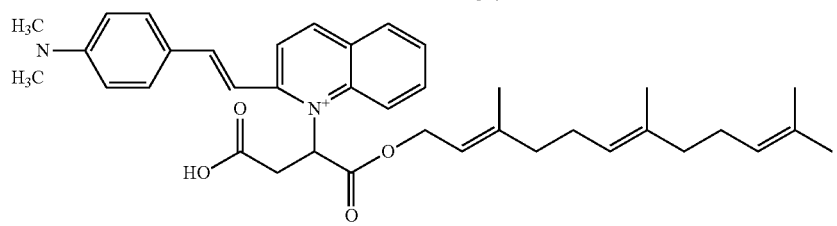
farnesol
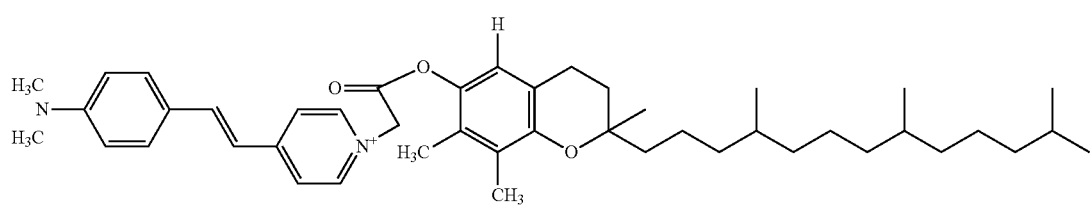
gamma-toc
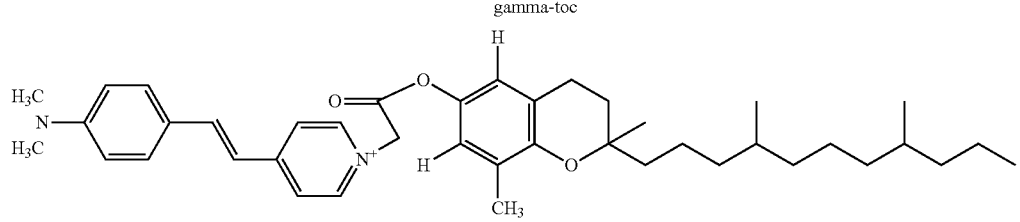
delta-toc
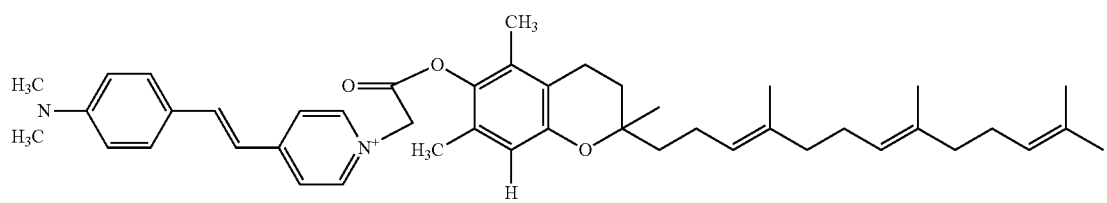
gamma-tocotrienol

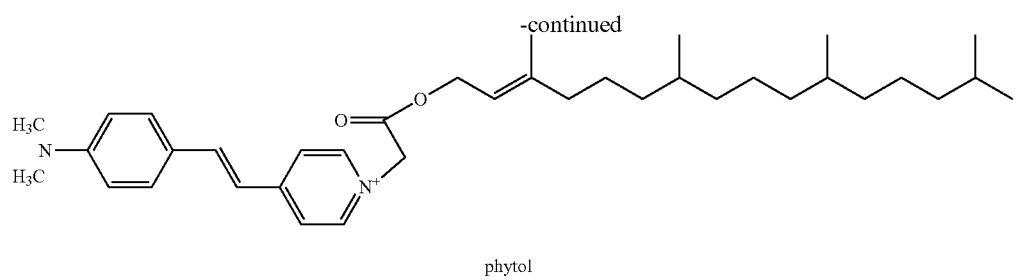
phytol
In the above figure, stereochemistry has been omitted for clarity. The beacons used in this aspect of Embodiment 4 can be synthesized according to the following reaction schemes.
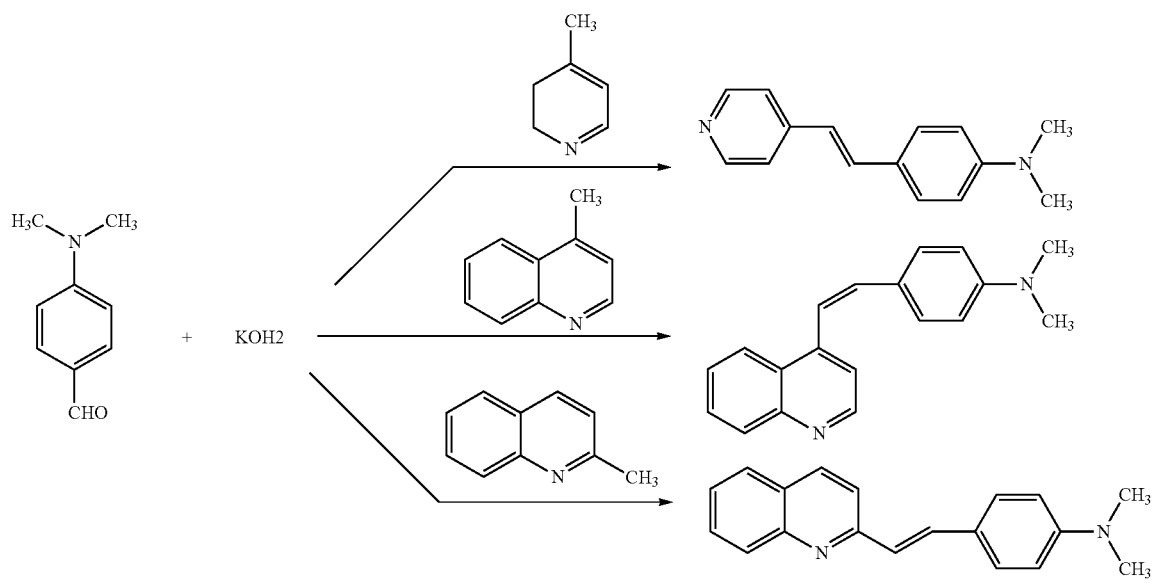
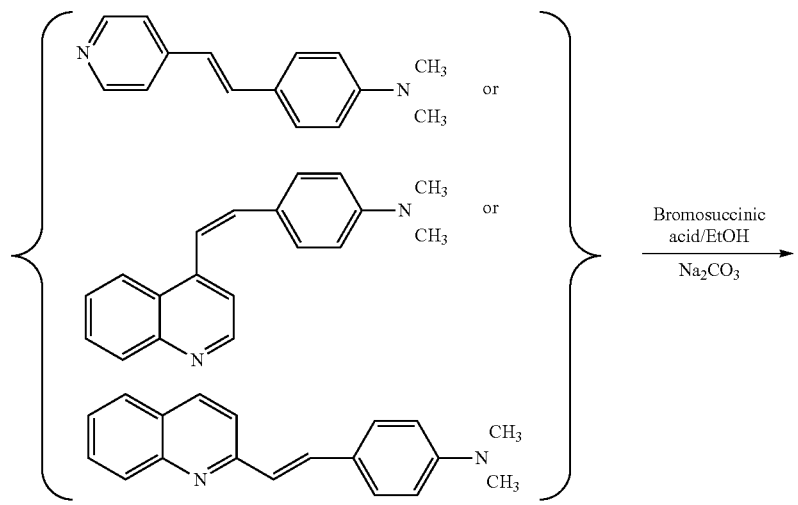

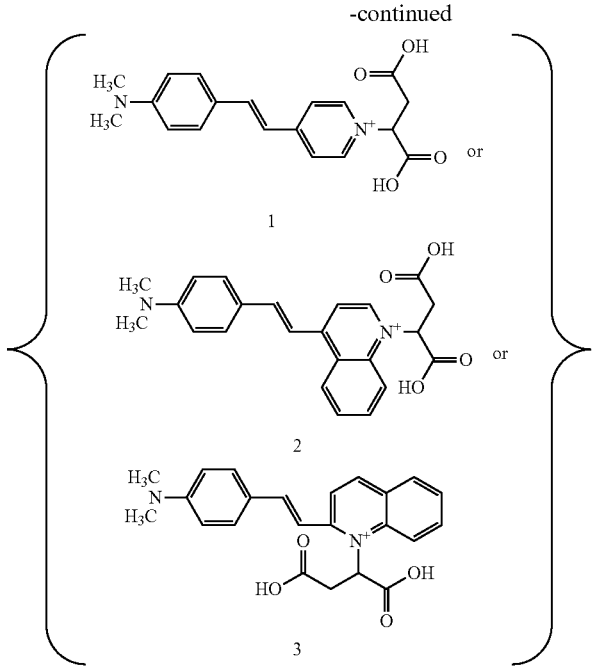
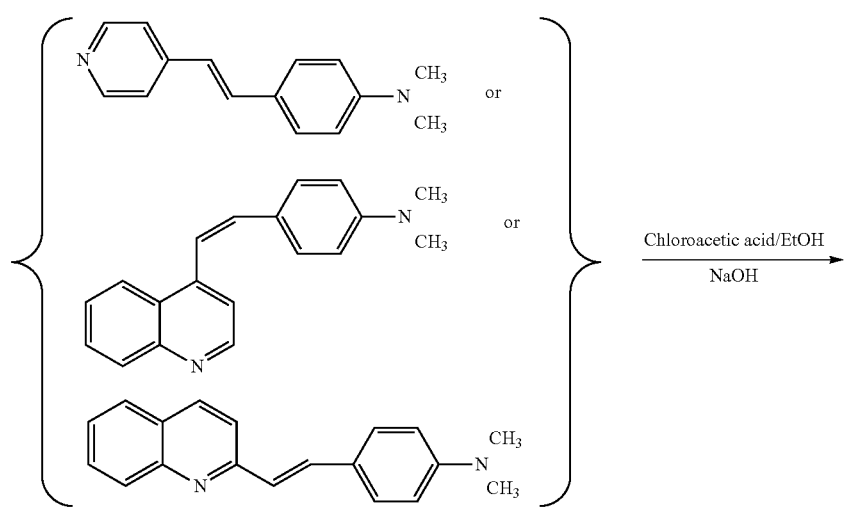

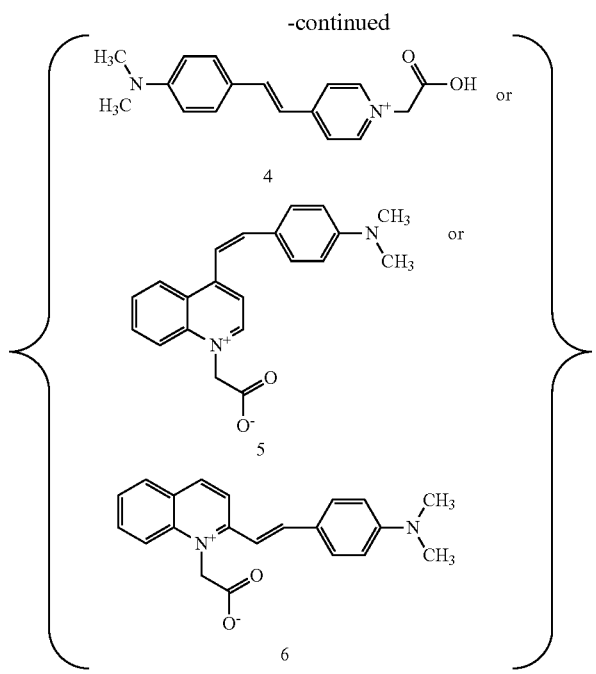
The complex of the natural product and the beacon may be synthesized according to the following reaction schemes (alpha-tocopherol is the natural product in these schemes).
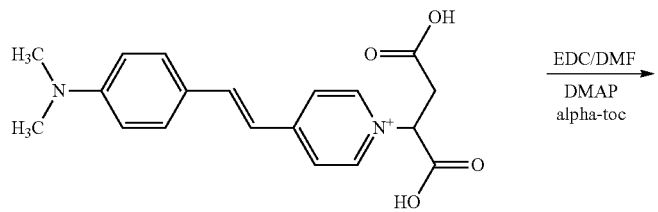
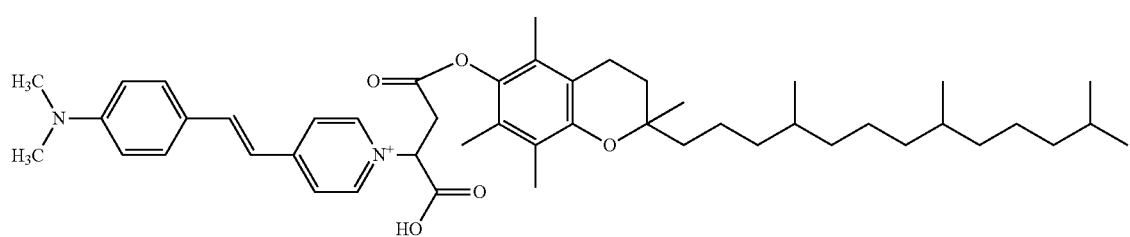
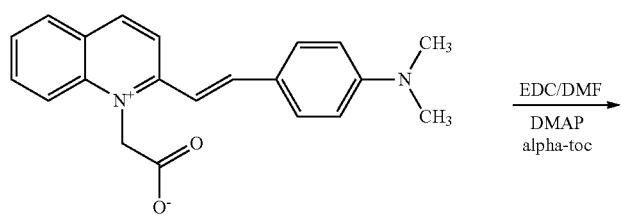

-continued

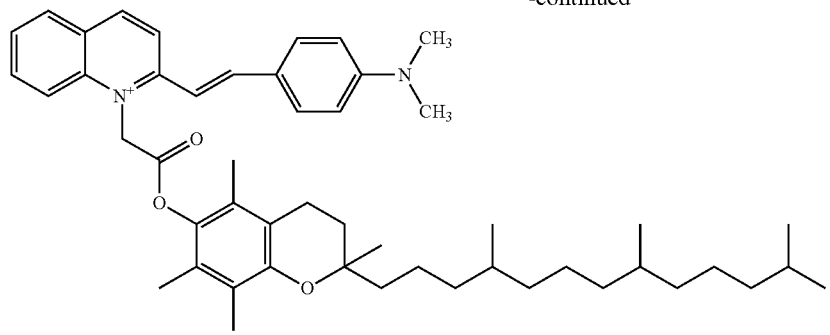

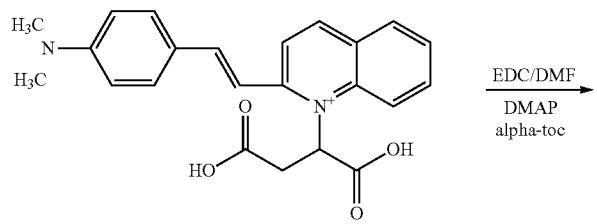

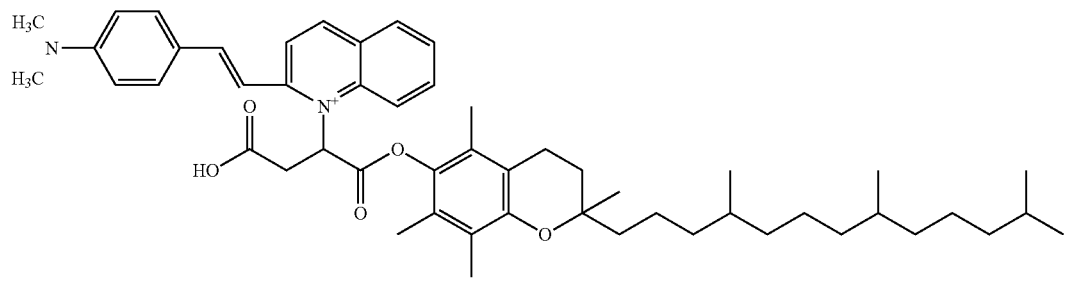

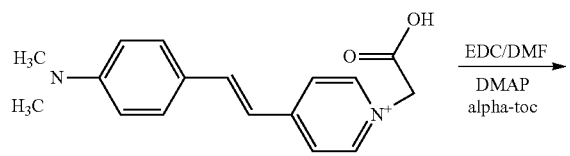

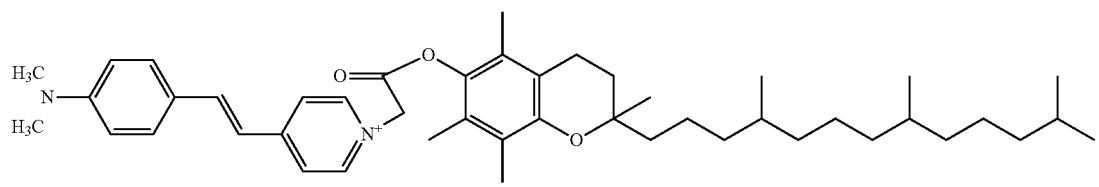

In the above figure, stereochemistry has been omitted for clarity. The theranostic systems of dicarboxylic fluorescent esters of NatP, demonstrate tunable fluorescence, thus excitation and emission spectra of the esters differ significantly from those of the free fluorophore. For example, the excitation/emission of the free fluorophore of the dicarboxylic styryl compound containing the quinoline ring is 485/615 nm. The excitation/emission of the subsequent tocotrienol and farnesol esters is 390/460 nm. The induction of tunable fluorescence with enzymatically cleavable chemical bonds yields different optical signal with enzymatic hydrolysis. Thus these optically active therapeutic agents enable direct detection, sensing and therapy. Furthermore, the complexes of the natural product and the beacon of this aspect of Embodiment 4 have shown enhanced proapoptotic properties in cancer cells compared to the "free" natural product. Without wishing to be bound by theory, it is believed this is due to structural modifications within the signal modulating aromatic ring and induction of complementary proapoptotic pathways by the hydrolysis products.

Aspect D of Embodiment 4

Another aspect of Embodiment 4 can be represented by the formula $[NatP]_3Ln^{3+} \cdot 2H_2O$, wherein the natural product and $Ln^{3+}$ are as defined herein. An example of this aspect is depicted below.

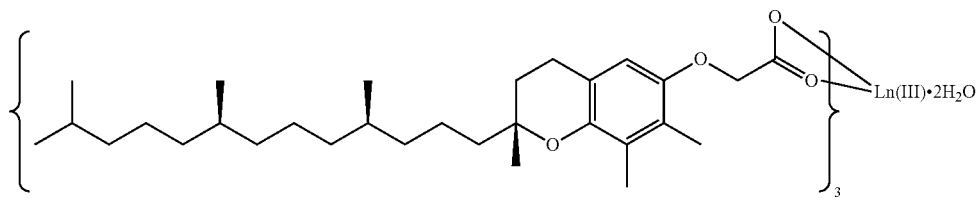

According to another aspect of the present invention, there is provided a method for treating and/or diagnosing cancer using the theranostic systems of the present invention.

In an embodiment, the theranostic systems of the present invention can be used in methods of treating and/or diagnosing multiple multifunctional malignancies such as colorectal cancer, lung cancer, head & neck cancer, breast cancer, prostate cancer, gastrointestinal cancer, brain tumors and melanoma.

The theranostic systems of the present invention solve the problems associated with early cancer detection. The theranostic systems may be administered by injection of the novel theranostic agents intravenously. Alternatively, they may be applied locally to the area of interest or sprayed. In embodiments where the beacon has fluorescent properties, the theranostic systems may be detected with a fluorescence endoscope or a fluorescence attachment to a standard endoscope or a fluorescent endoscopy capsule.

The applications of the invention described herein includes, but is not limited to: (i) minimization/elimination of target biopsies and frequency of surveillance; (ii) detection and localization of high-grade dysplasias in predisposing conditions (e.g. inflammations, familial cancers etc.); (iii) identification of neoplasia beneath the mucosa (e.g. familial stomach cancer); (iv) assessment of depth of tumor invasion for possible mucosal resection; (v) preoperative identification of tumor margins and image-guided surgery (vi) evaluation of effectiveness of pharmacological therapy; (vii) distinguishing adenomatous from hyperplastic polyps; (viii) avoiding biopsy in patients with bleeding diatheses; (ix) surveillance of polypectomy and mucosal resection site; (x) differentiation of malignant and benign ulcers and strictures; (xi) concurrent detection of micrometastasis in proximal and distant sites through MRI functionalities.

For example, the theranostic systems may be used with a fluorescent whole body imaging system, such as Fluorescent Molecular Tomography (FMT) for early cancer detection and localization of micrometastasis. For example, the theranostic systems may be used with an external fluorescent probe for delineation of surgical margins. For example, the theranostic systems may be used with a suitable MRI coil for early cancer detection and assessment of micrometastasis. For example, the theranostic systems may be used with a suitable RF antenna for early cancer detection and assessment of micrometastasis.

Key applications of the theranostic systems of the present invention, with all related advantages, could include (i) any endoscopy accessible malignancy (e.g. lung, stomach, endometrial, cervical cancer etc.) (ii) laparoscopically accessible lesions (e.g. ovarian cancer), (iii) directly visible lesions such as skin melanomas, oral cancer etc. The theranostic systems of the present invention are advantageous in that they could be used to detect cancer at the very early stages of carcinogenesis, before any suspicious visible lesions arise. In addition, they could replace the use of conventional endoscopic technology with molecular optical endoscopy and thus advance diagnosis beyond the state-of-the-art.

The theranostic systems of the present invention are also advantageous in that they will increase the efficacy, sensitivity, and predictive diagnostic value of cancer diagnosis. In turn, this will lead to a reduction in the ambiguity of diagnosis and allow definitive diagnosis and treatment on the same visit. The technology also has the potential to be extended to the diagnosis of many types of cancer and chronic inflammatory disorders.

Concomitantly, theranostic systems with magnetic or RF or nuclear functionalities will enable the detection of early micrometastasis through appropriate MRI imaging modalities and treatment monitoring with MRI, RF or PET applications. Additionally, MRI, RF and PET attributes will enable the direct assessment of brain malignancies as well as their localization and dissemination at the very early cellular level. Further, the kinase inhibitory properties will ensure early inactivation of cancer stimulating signals generated and transduced through the kinase receptors.

In another aspect of the present invention, there is provided a kit including a container having the theranostic system according to the present invention, as herein described. The kit may include more than one container. For example, the kit may include a first container containing a complex or combination of the quinazoline based tyrosine kinase inhibitor and the beacon and a second container containing the natural product. In another embodiment, the kit may include a first container containing a complex or combination of the natural product and the beacon and a second container containing the quinazoline based tyrosine kinase inhibitor. The kits according to the present invention may further include written instructions as to the use of the components in the treatment and diagnosis of cancer. For instance, when the kit includes a first container containing a complex or combination of the quinazoline based tyrosine kinase inhibitor and the beacon and a second container containing the natural product, the instructions may provide directions for mixing the contents of the first and second containers prior to application or for the sequential application of the contents of the first and second containers. Methods of application may also be described.

EXAMPLES

The invention will now be further described and illustrated by means of the following examples, it being understood that these are intended to explain the invention, and in no way to limit its scope.

Example A

Synthesis of an Anilinoquinazoline Based Tyrosine Kinase Inhibitor that May be Included in the Theranostic Systems of the Present Invention The first step in the synthesis of the anilinoquinazolines involves the cyclization of commercially available 2-amino-4-nitrobenzoic acid to 7-nitroquinazolin-4(3H)-one.

Synthesis of 7-nitroquinazolin-4(3H)-one

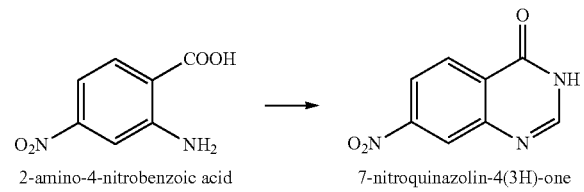 [SMILES: Nc1cc([N+](=O)[O-])ccc1C(=O)O ; O=c1[nH]cnc2cc([N+](=O)[O-])ccc12]

2-amino-4-nitrobenzoic acid → 7-nitroquinazolin-4(3H)-one

A mixture of 2-amino-4-nitrobenzoic acid (10.0 g, 54.93 mmol) was refluxed at 130° C. for 18 h in methoxyethanol (50 mL) and formamidine acetate (11.43 g, 109.81 mmol). The clear reaction mixture was cooled to room-temperature to form a yellowish precipitant. The solvent was removed under vacuum, and the precipitant was washed several times with aqueous ammonia (0.01 M). The solid was dried in vacuo to yield 8.9 g (84%) of a light yellow powder. $^1$H NMR Data: dmso-$d_6$-ppm ($\delta$); 12.68 (1H), 8.37 (d, 1H), 8.33 (d, 1H), 8.26 (1H) and 8.23 (dd, 1H).

The introduction of the aniline moiety of the anilinoquinazolines at the C4 position can be achieved by a two-step process of (a) chlorination and (b) nucleophilic aromatic substitution by different anilines.

Synthesis of 4-chloro-7-nitroquinazoline

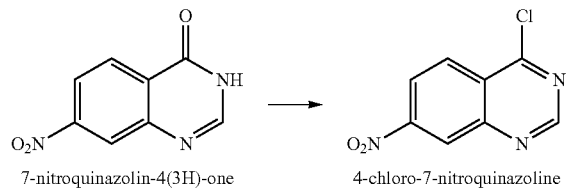 [SMILES: O=c1[nH]cnc2cc([N+](=O)[O-])ccc12 ; O=[N+]([O-])c1ccc2c(Cl)ncnc2c1]

7-nitroquinazolin-4(3H)-one → 4-chloro-7-nitroquinazoline 7-nitroquinazolin-4(3H)-one (20.93 mmol) was suspended in 35 mL of thionyl chloride with a catalytic amount of DMF (3 drops). The mixture was refluxed at 110° C. for approximately 3 hrs until the solution turned clear. The SOCl$_2$ was removed under reduced pressure and then dry benzene was added. The mixture was again reduced under pressure to remove all traces of SOCl$_2$. The crude solid was dissolved in dichloromethane (CH$_2$Cl$_2$). The solution was treated by Na$_2$CO$_3$ carefully until the solution reached pH 7-8. The solution was extracted with dichloromethane (CH$_2$Cl$_2$) and dried over Na$_2$SO$_4$. The solvent was removed under reduced pressure to give the 4-chloro-7-nitroquinazoline (3.5 gram; 16.74 mmol).

Typical Procedure of the Synthesis of Anilinoquinazolines from 4-Chloro-7-Nitroquinazoline 4-chloro-7-nitroquinazoline (4.77 mmol) was dissolved in 50 mL of dichloromethane (CH$_2$Cl$_2$) and added to a stirred solution of different anilines in i-PrOH (30 mL). The reaction mixture was stirred for 3 hrs, after which time the desired compounds began to precipitate. This was an indication that the nucleophilic aromatic substitution reaction was happening. The yellow solids were filtered, washed with isopropanol (2×50 mL), and, after vacuum drying, the desired compounds were obtained. The compounds were confirmed by their $^1$H NMR spectra and ESI-MS.

Synthesis of N-(4-bromophenyl)-7-nitroquinazolin-4-amine

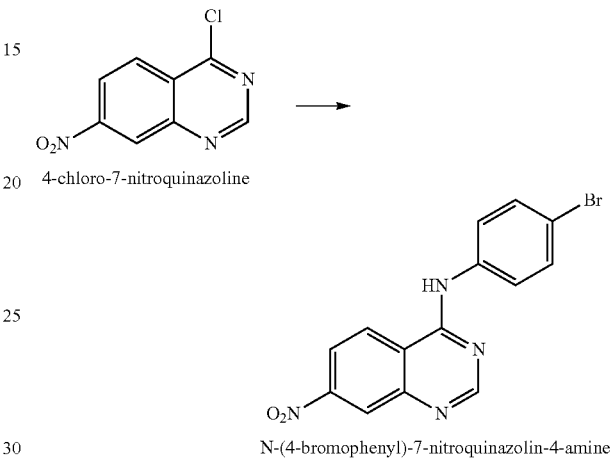

N-(4-bromophenyl)-7-nitroquinazolin-4-amine

4-Bromoaniline (1.0 g, 5.0 mmol) was dissolved in 25 mL isopropanol and rapidly added to a room temperature solution of 4-chloro-7-nitroquinazoline (1.2 g) in 10 mL CH$_2$Cl$_2$ at room-temperature. After 40 min, precipitation of the desired compound was observed. The reaction was stirred for another 60 min. The yellow solids were filtered, washed with isopropanol (2×50 mL), and after vacuum drying, the desired compound was obtained. $^1$H NMR Data: dmso-$d_6$-ppm ($\delta$); 11.51 (1H), 9.08 (d, 1H), 8.96 (1H), 8.66 (d, 1H), 8.50 (dd, 1H), 7.80 (d, 2H) and 7.68 (d, 2H).

Synthesis of N-(4-isopropylphenyl)-7-nitroquinazolin-4-amine

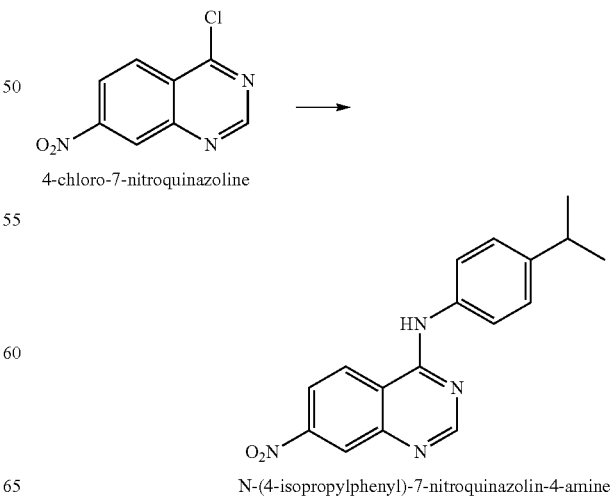

N-(4-isopropylphenyl)-7-nitroquinazolin-4-amine 4-isopropylaniline (5.0 mmol) was dissolved in 25 mL isopropanol and rapidly added to a room temperature solution of 4-chloro-7-nitroquinazoline (1.2 g) in 10 mL CH$_2$Cl$_2$ at room-temperature. After 3 hrs. precipitation of the desired compound was observed. The reaction was stirred for another 60 min. The yellow solids were filtered, washed with isopropanol (2×50 mL), and after vacuum drying, the desired compound was obtained. $^1$H NMR Data: dmso-d$_6$-ppm (δ); 11.51 (1H), 9.08 (d, 1H), 8.96 (1H), 8.66 (d, 1H), 8.50 (dd, 1H), 7.66 (d, 2H), 7.36 (d, 2H), 2.94 (m, 1H) and 1.23 (d, 6H).

Synthesis of N-(4-(tert-butyl)phenyl)-7-nitroquinazolin-4-amine

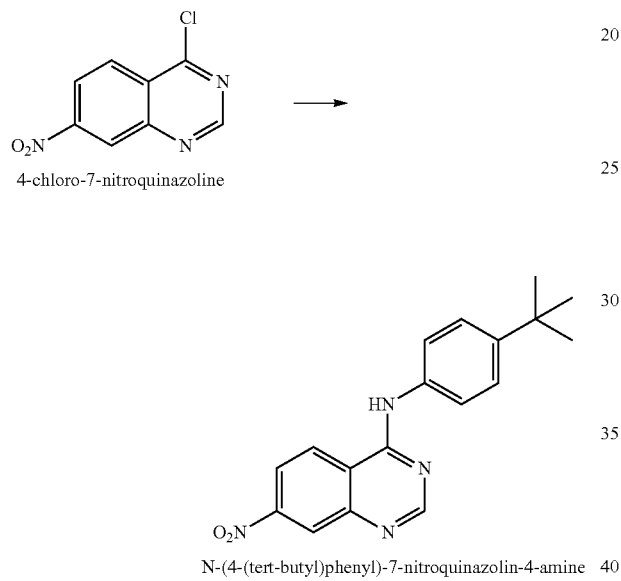

N-(4-(tert-butyl)phenyl)-7-nitroquinazolin-4-amine 4-(tert-butyl)aniline (5.0 mmol) was dissolved in 25 mL isopropanol and rapidly added to a room temperature solution of 4-chloro-7-nitroquinazoline (1.2 g) in 10 mL CH$_2$Cl$_2$ at room-temperature. After 4 hrs. precipitation of the desired compound was observed. The reaction was stirred for another 60 min. The yellow solids were filtered, washed with isopropanol (2×50 mL), and after vacuum drying, the desired compound was obtained. $^1$H NMR Data: dmso-d$_6$-ppm (δ); 11.56 (1H), 9.07 (d, 1H), 8.93 (1H), 8.65 (d, 1H), 8.51 (dd, 1H), 7.67 (d, 2H), 7.51 (d, 2H) and 1.32 (9H).

Synthesis of N-(naphthalen-1-ylmethyl)-7-nitroquinazolin-4-amine

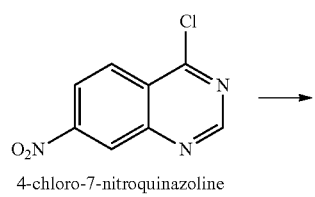

4-chloro-7-nitroquinazoline

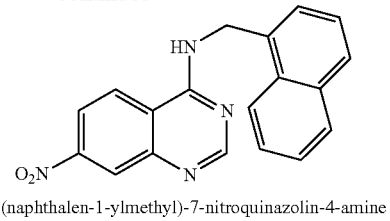

N-(naphthalen-1-ylmethyl)-7-nitroquinazolin-4-amine (1-naphthylmethyl)amine (5.0 mmol) was dissolved in 25 mL isopropanol and rapidly added to a room temperature solution of 4-chloro-7-nitroquinazoline (1.2 g) in 10 mL CH$_2$Cl$_2$ at room-temperature. After 30 mins, precipitation of the desired compound was observed. The reaction was stirred for another 60 min. The yellow solids were filtered, washed with isopropanol (2×50 mL), and after vacuum drying, the desired compound was obtained. $^1$H NMR Data: dmso-d$_6$-ppm (δ); 9.27, 8.64-8.28 (4H), 8.26-7.52 (m, 7H) and 5.28 (d, 2H).

The next step in the synthesis of the anilinoquinazolines was the reduction of the nitro group at the C7 position. The reduction of the different anilinoquinazolines was performed by an iron (Fe) catalyst in the presence of a solvent (ethanol: acetic acid:water (2:2:1)). A representative method to obtain the N$^4$-(4-bromophenyl)quinazoline-4,7-diamine from N-(4-bromophenyl)-7-nitroquinazolin-4-amine is described below.

Synthesis of N$^4$-(4-bromophenyl)quinazoline-4,7-diamine

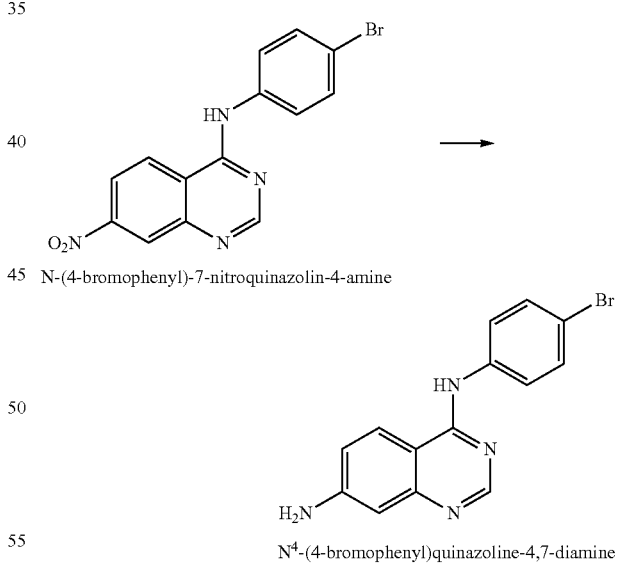

N-(4-bromophenyl)-7-nitroquinazolin-4-amine

N$^4$-(4-bromophenyl)quinazoline-4,7-diamine

To a suspension of N-(4-bromophenyl)-7-nitroquinazolin-4-amine (0.3 g, 0.86 mmol) in a mixture of glacial acetic acid (4 mL), ethanol (4 mL) and water (2 mL) was added reduced iron powder (0.24 g, 4.29 mmol). The resulting suspension was refluxed at 85° C. with TLC analysis monitoring for the completion of the reaction. After completion the reaction mixture was filtered to remove the iron residue which was washed with ethyl acetate (30 mL). The filtrate was partitioned with 2M KOH and the basic layer was further extracted with ethyl acetate (3×25 mL). The combined organic extracts were washed with brine (2×25 mL) and water (3×50 mL), dried (MgSO$_4$) and concentrated under reduced pressure. The crude residue was then subjected to flash silica gel column chromatography (20% ethyl acetate in hexanes) yielding N$^4$-(4-bromophenyl)quinazoline-4,7-diamine (70%). The compound was confirmed by $^1$H NMR spectra. $^1$H NMR Data: dmso-d$_6$-ppm (δ); 9.39 (1H), 8.35 (1H), 8.17 (d, 1H), 7.84 (d, 2H), 7.51 (d, 2H), 6.90 (dd, 1H) 6.71 (d, 1H) and 6.05 (2H).

The $^1$H NMR peaks for N$^4$-(4-isopropylphenyl)quinazoline-4,7-diamine, N$^4$-(4-(tert-butyl) phenyl)quinazoline-4,7-diamine and N$^4$-(naphthalen-1-ylmethyl)quinazoline-4,7-diamine are as follows:

N$^4$-(4-isopropylphenyl)quinazoline-4,7-diamine: dmso-d$_6$-ppm (δ); 9.25 (1H), 8.28 (1H), 8.15 (d, 1H), 7.68 (d, 2H), 7.20 (d, 2H), 6.87 (dd, 1H) 6.69 (d, 1H), 5.98 (2H), 2.86 (m, 1H), 1.21 (d, 2H).

N$^4$-(4-(tert-butyl) phenyl)quinazoline-4,7-diamine: dmso-d$_6$-ppm (δ); 9.25 (1H), 8.29 (1H), 8.15 (d, 1H), 7.68 (d, 2H), 7.35 (d, 2H), 6.89 (dd, 1H) 6.69 (d, 1H), 5.98 (2H) and 1.18 (9H).

N$^4$-(naphthalen-1-ylmethyl)quinazoline-4,7-diamine: dmso-d$_6$-ppm (δ); 8.48 (1H), 8.50-6.60 (11H), 5.90 (2H) and 5.23 (2H).

In embodiments of the present invention in which the anilinoquinazolines are conjugated to the functionalized cyclen, the anilinoquinazolines are further modified at their C7 position by chloroacetylchloride. In a general method, five equivalents of triethylamine was added to a solution of the anilinoquinazoline in DMF under argon atmosphere at room temperature. The solution was stirred for 30 mins. The temperature of the solution was brought to 0° C. and 1.7 equivalents of chloroacetylchloride was added dropwise for 30 mins. The required compound precipitated out and was filtered.

A representative method to obtain the N-(4-((4-bromophenyl)amino)quinazolin-7-yl)-2-chloroacetamide from N$^4$-(4-bromophenyl)quinazoline-4,7-diamine is described below.

Synthesis of N-(4-((4-bromophenyl)amino)quinazolin-7-yl)-2-chloroacetamide

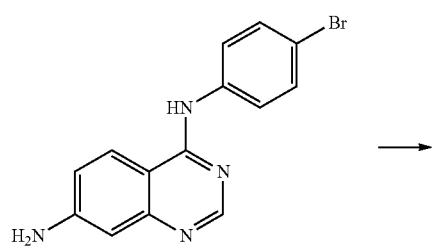

N$^4$-(4-bromophenyl)quinazoline-4,7-diamine

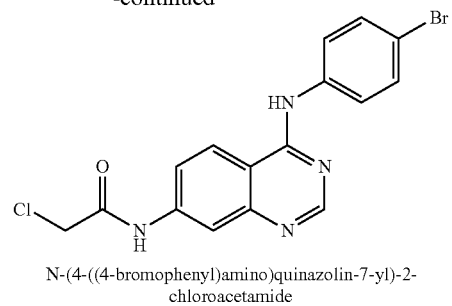

N-(4-((4-bromophenyl)amino)quinazolin-7-yl)-2-chloroacetamide

N$^4$-(4-bromophenyl)quinazoline-4,7-diamine (0.2696 mmol) was dissolved in 10 mL tetrahydrofuran and 11 mL dimethylformamide. After, triethylamine (41 μL, 0.3126 mmol) was added to the solution and the solution was stirred for 30 mins. at room-temperature. The temperature of the solution was brought to 0° C. and chloroacetyl chloride (25 μL (0.3126 mmol) was added dropwise into the solution. The precipitate was collected and dried under vacuum. The product was confirmed by $^1$H NMR spectra. $^1$H NMR Data: dmso-d$_6$-ppm (δ), 10.74 (1H), 9.80 (1H), 8.57 (1H), 8.50 (d, 1H), 8.14 (d, 1H), 7.88 (d, 2H), 7.75 (dd, 1H), 7.57 (d, 2H) and 4.05 (2H).

The $^1$H NMR peaks for 2-chloro-N-(4-((isopropylphenyl)amino)quinazolin-7-yl)acetamide, N-(4-((4-(tert-butyl)phenyl)amino)quinazolin-7-yl)-2-chloroacetamide and 2-chloro-N-(4-((naphthalen-1-ylmethyl)amino)quinazolin-7-yl)acetamide are as follows:

2-chloro-N-(4-((isopropylphenyl)amino)quinazolin-7-yl)acetamide: dmso-d$_6$-ppm (δ) 11.48 (1H), 8.85-8.70 (m, 2H), 8.42 (1H), 7.87 (d, 1H), 7.59 (d, 2H), 7.35 (d, 2H), 5.75 (1H), 4.45 (2H), 2.98-2.90 (m, 1H) and 1.24 (d, 6H).

N-(4-((4-(tert-butyl)phenyl)amino)quinazolin-7-yl)-2-chloroacetamide: dmso-d$_6$-ppm (δ), 10.90 (1H), 10.01 (1H), 8.55 (d, 2H), 8.17 (1H), 7.75 (d, 1H), 7.70 (d, 2H), 7.41 (d, 2H), 4.38 (2H) and 1.30 (9H).

2-chloro-N-(4-((naphthalen-1-ylmethyl)amino)quinazolin-7-yl)acetamide: dmso-d$_6$-ppm (δ); 11.40 (1H), 10.67 (1H), 8.90-7.64 (11H), 5.40 (2H) and 4.40 (2H).

Example B

Synthesis of Theranostic Systems Comprising a Heterometallic Multimodal Beacon and an Anilinoquinazoline The general synthetic scheme to the functionalisation of the cyclen is depicted below.

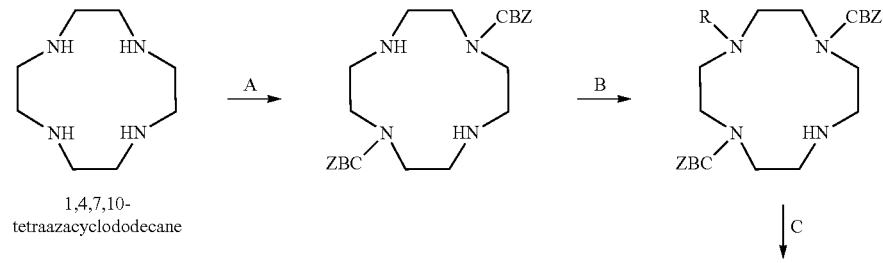

1,4,7,10-tetraazacyclododecane

-continued

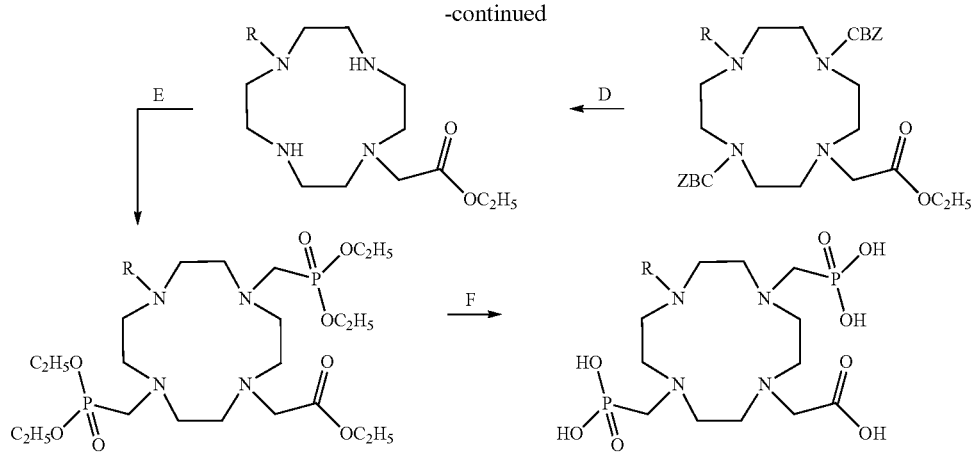

A) Benzoyl chloroformate, Chloroform, overnight stirring, RT; B) Anilinoquinazolines, Cs2Co3, KI, ethanol, reflux, 48 h; C) Ethyl-bromoacetate, Cs2Co3, Ethanol reflux 24 h; D) Pd/C, Cyclohexene, Ethanl, reflux 18 h; E) triethlphosphite, Dry, paraformaldehyde; F) 20% HCl, room-temperature 12 h and then refluxed for 36 h.

Synthesis of dibenzyl 1,4,7,10-tetraazacyclododecane-1,7-dicarboxylate

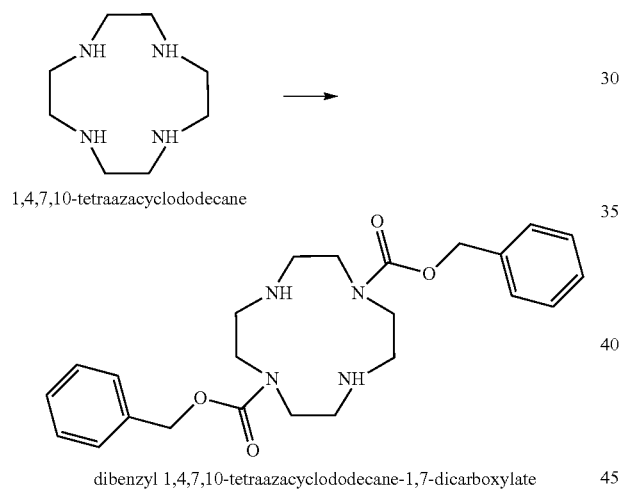

1,4,7,10-tetraazacyclododecane dibenzyl 1,4,7,10-tetraazacyclododecane-1,7-dicarboxylate To a solution of 1,4,7,10 tetraazacyclododecane free base (671 mg, 3.39 mmol) in chloroform (35 mL) in an ice bath was added benzyl chloroformate (2 equiv) dropwise. The reaction mixture was stirred overnight giving abundant solid formation. Solvent was removed by rotary evaporation and ether (30 mL) was added. The solid was filtered, washed with ether and dried yielding 1.735 g (100%) of the dihydrochloride salt as a white solid. The free base was obtained by adding NaOH (30 mL, 3M) to the solid. Aqueous phase was extracted with chloroform (3×30 mL). The extracts were combined and dried ($K_2CO_3$). The solvent was removed by rotary evaporation and the residue was dried under vacuum for several hours giving 1.449 g (100%) of transparent oil.

Synthesis of dibenzyl 4-(2-((4-((4-bromophenyl)amino)quinazolin-7-yl)amino)-2-oxoethyl)-1,4,7,10-tetraazacyclododecane-1,7-dicarboxylate

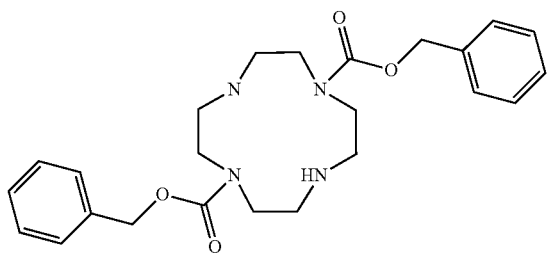

dibenzyl 1,4,7,10-tetraazacyclododecane-1,7-dicarboxylate

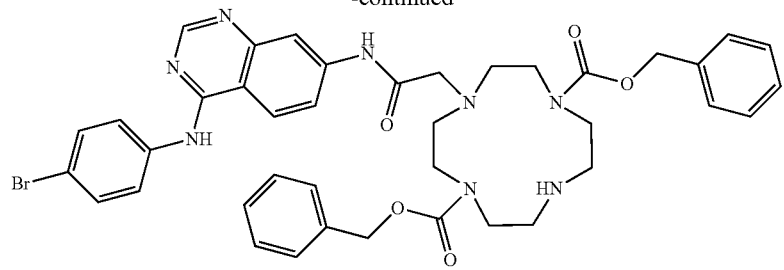

dibenzyl 4-(2-((4-((4-bromophenyl)amino)quinazolin-7-yl)amino)-2-oxoethyl)-1,4,7,10-tetraazacyclododecane-1,7-dicarboxylate A suspension of N-(4-((4-bromophenyl)amino)quinazolin-7-yl)-2-chloroacetamide, (0.130 mmol), dibenzyl 1,4,7,10-tetraazacyclododecane-1,7-dicarboxylate (0.130 mmol), caesium carbonate (0.130 mmol) and potassium iodide (0.130 mmol) in dry ethanol (5 mL) was heated at reflux for 72 h. Removal of solvent under reduced pressure yielded a residue which was suspended in dichloromethane (20 mL) and filtered; the filter cake was washed well with dichloromethane (3×20 mL).

Synthesis of dibenzyl 4-(2-((4-((4-bromophenyl)amino)quinazolin-7-yl)amino)-2-oxoethyl)-10-(2-ethoxy-2-oxoethyl)-1,4,7,10-tetraazacyclododecane-1,7-dicarboxylate

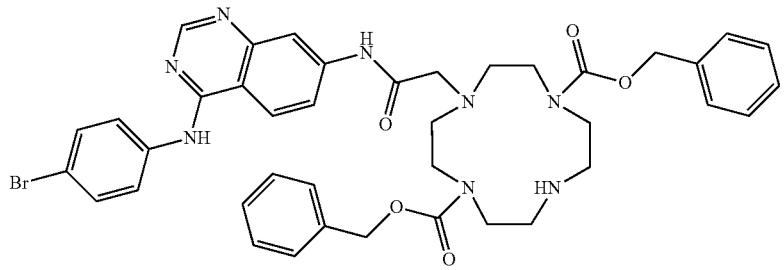

dibenzyl 4-(2-((4-((4-bromophenyl)amino)quinazolin-7-yl)amino)-2-oxoethyl)-1,4,7,10-tetraazacyclododecane-1,7-dicarboxylate

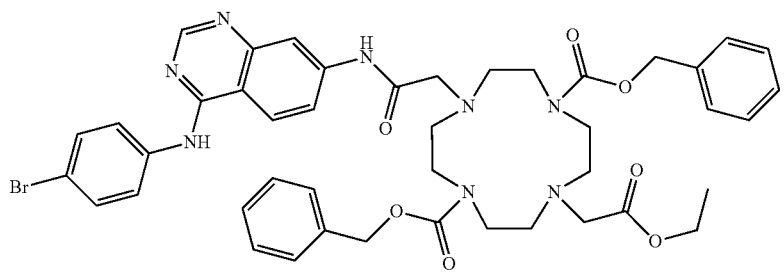

dibenzyl 4-(2-((4-((4-bromophenyl)amino)quinazolin-7-yl)amino)-2-oxoethyl)-10-(2-ethoxy-2-oxoethyl)-1,4,7,10-tetraazacyclododecane-1,7-dicarboxylate The functionalisation of the cyclen was performed by heating ethyl chloroacetate with the starting cyclen in dry ethanol in the presence of caesium carbonate.

Synthesis of ethyl 2-(7-(2-((4-((4-bromophenyl)amino)quinazolin-7-yl)amino)-2-oxoethyl)-1,4,7,10-tetraazacyclododecan-1-yl)acetate

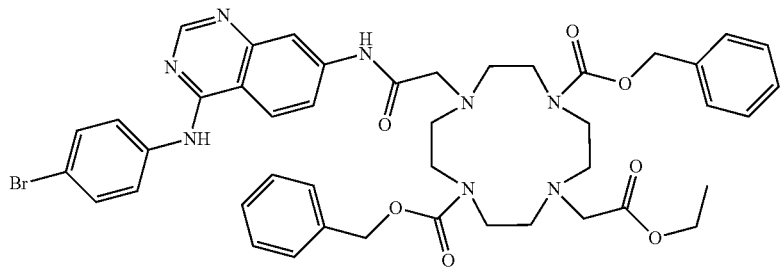

dibenzyl 4-(2-((4-((4-bromophenyl)amino)quinazolin-7-yl)amino)-2-oxoethyl)-10-(2-ethoxy-2-oxoethyl)-1,4,7,10-tetraazacyclododecane-1,7-dicarboxylate

↓

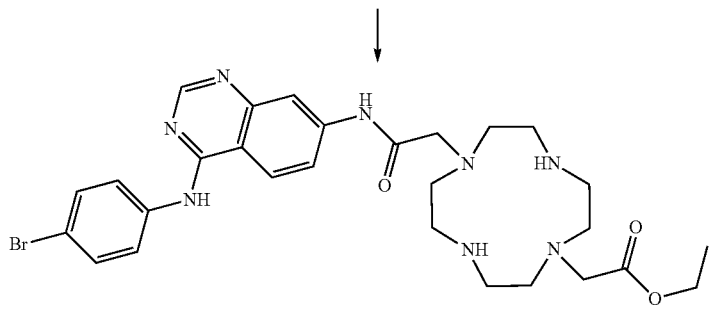

ethyl 2-(7-(2-((4-((4-bromophenyl)amino)quinazolin-7-yl)amino)-2-oxoethyl)-1,4,7,10-tetraazacyclododecan-1-yl)acetate Cyclohexene (1.91 g, 23.3 mmol) was added to a stirred solution of dibenzyl 4-(2-((4-((4-bromophenyl)amino)quinazolin-7-yl)amino)-2-oxoethyl)-10-(2-ethoxy-2-oxoethyl)-1,4,7,10-tetraazacyclododecane-1,7-dicarboxylate dissolved in absolute ethanol. 10% Palladium on carbon catalyst was then added. The reaction mixture was refluxed at 80° C. for 5 h, and filtered through Celite. The filtrate was concentrated in vacuo to give the free base.

Synthesis of ethyl 2-(7-(2-((4-((4-bromophenyl)amino)quinazolin-7-yl)amino)-2-oxoethyl)-4,10-bis((diethoxyphosphoryl)methyl)-1,4,7,10-tetraazacyclododecan-1-yl)acetate

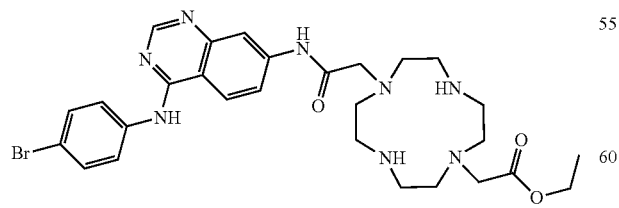

↓

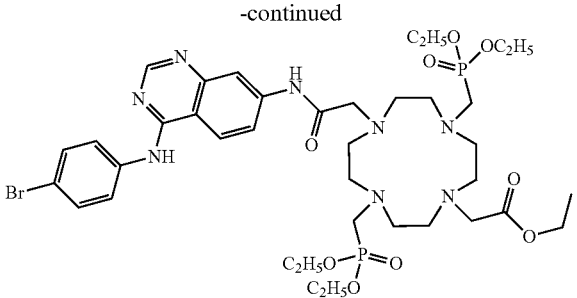

ethyl 2-(7-(2-((4-((4-bromophenyl)amino)quinazolin-7-yl)amino)-2-oxoethyl)-4,10-bis(diethoxyphosphoryl)methyl)-1,4,7,10-tetraazacyclododecan-1-yl)acetate Compound was dissolved in triethyl phosphite (2.58 mL, 14.8 mmol). Paraformaldehyde was then added in small portions over 1 h. The solution was finally stirred at room temp. for an additional 4 d. The volatiles were evaporated and the residue was co-evaporated with toluene and dried under vacuum for several hours to yield a clear oil (3.34 g).

Synthesis of 2-(7-(2-((4-((4-bromophenyl)amino)
quinazolin-7-yl)amino)-2-oxoethyl)-4,10-bis
(phosphonomethyl)-1,4,7,10-tetraazacyclododecan-
1-yl)acetic acid

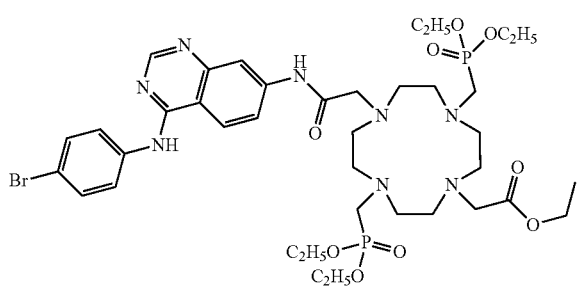

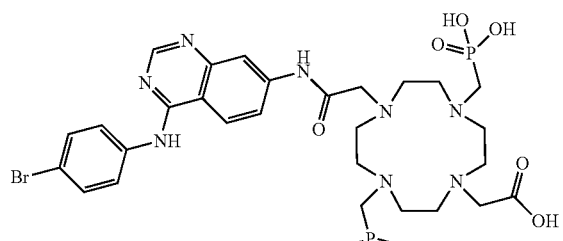

2-(7-(2-((4-((4-bromophenyl)amino)quinazolin-7-yl)amino)-2-oxoethyl)-
4,10-bis(phosphonomethyl)-1,4,7,10-tetraazacyclododecan-1-yl)acetic acid The compound was stirred at room temperature for 12 h in the presence of a 20% aqueous solution of HCl and then refluxed for 36 h.

Synthesis of 2-(7-(2-((4-((4-bromophenyl)amino)
quinazolin-7-yl)amino)-2-oxoethyl)-4,10-bis
(phosphonomethyl)-1,4,7,10-tetraazacyclododecan-
1-yl)acetic acid, gadolinium(III) salt

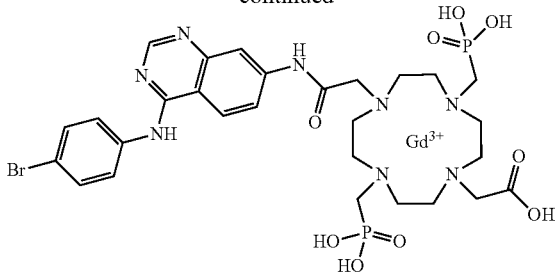

A solution starting compound in methanol was heated under reflux in the presence of $GdCl_3 \cdot 6H_2O$ for 24 hours. The solvent was removed under reduced pressure and the crude product was recrystallised by slow diffusion of diethyl ether into an ethanolic solution of the complex at room temperature to afford the product.

Synthesis of the Ruthenium Complex

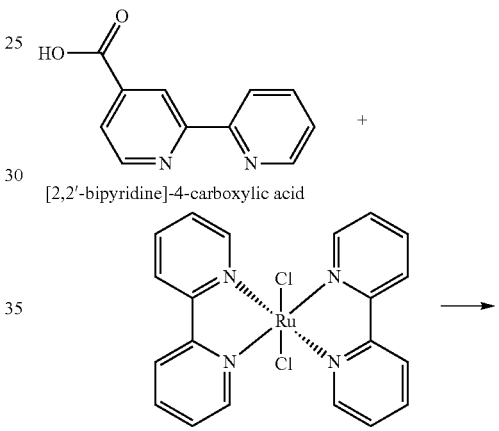

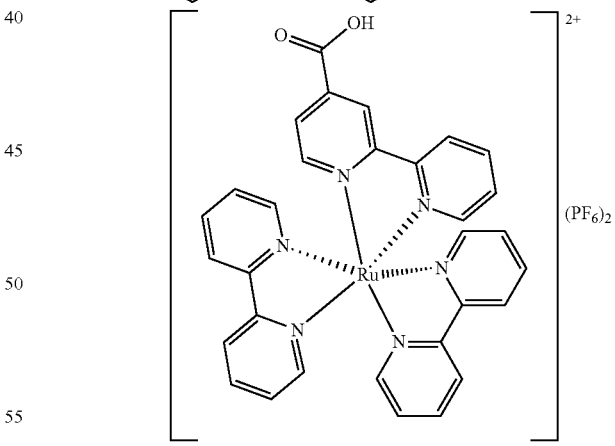

To a solution of 32 mL of methanol and 8 mL of a saturated aqueous solution of $NaHCO_3$, 0.165 g (0.82 mmol) of 2,2'-bipyridine-4-carboxylic acid is added and heated to 50° C. until the solution is clear. Then 0.4 g (0.82 mmol) of cis-dichlorobis(2,2'-bipyridine)ruthenium(II) (Ru(bipy)$_2$ Cl$_2$.2H$_2$O) are added and the mixture is refluxed for 24 h. After cooling in an ice bath for 1 h conc. H$_2$SO$_4$ is added dropwise to adjust the solution to pH 3. The formed precipitate was filtered washed with MeOH, the filtrate was treated with 5 g NaPF$_6$ in 25 ml H$_2$O, then cooled in an ice bath, and the precipitate was collected by filtration.

Synthesis of the Anilinoquinazoline-Heterometallic Beacon Complex

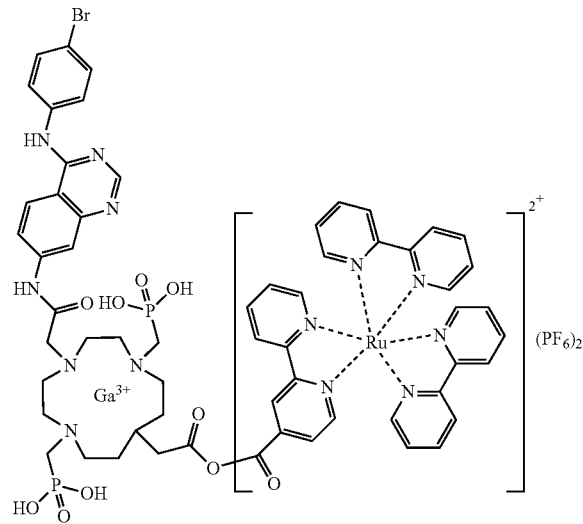

2-(7-(2-((4-((4-bromophenyl)amino)quinazolin-7-yl)amino)-2-oxoethyl)-4,10-bis(phosphonomethyl)-1,4,7,10-tetraazacyclododecan-1-yl)acetic acid, gadolinium(III) salt was dissolved in ethanol and the pH adjusted to pH 8 by the addition of $NaHCO_3$. A solution of the Ruthenium complex in acetonitrile was added and the reaction mixture was heated at 50° C. for 17 hours to afford the final anilinoquinazoline-heterometallic beacon complex.

Example C

The following example concerns the embodiments of the present invention in which the theranostic system comprises an anilinoquinazoline tyrosine-kinase inhibitor in combination or complexed to a multimodal heterometallic compound comprising a functionalised macrocyclic lanthanide complex and a poly-pyridyl near infra-red emitter transition metal complex.

In order to determine the optical properties and safety profile of the poly-pyridyl near infra-red emitter transition metal complex, the following ruthenium complex was tested.

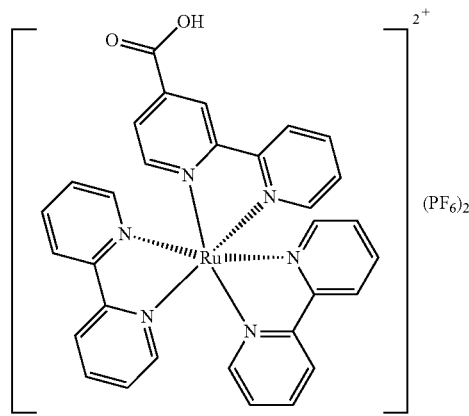

First, the ruthenium complex was subjected to spectrophotometric analysis. The excitation/emission spectra confirmed that ruthenium retained its fluorescence properties and signal strength throughout the complexation process. The excitation/emission maximum was determined to be at 470/639 nm (data not shown).

It was also determined that the ruthenium complex demonstrates favorable imaging and intracellular distribution properties. Following 24 h incubation with green fluorescent protein(GFP)/luciferase (Luc) fluorescently transfected colon cancer (SW480, SW460) and malignant glioma (U87) cells, confocal and standard upright fluorescence microscopy revealed bright red fluorescent "dots" in the cytoplasm, mostly prominent in the perinuclear area (see FIG. 1). The formation of "dots" rather than diffuse cytoplasmic distribution is highly suggestive of sub-cellular organelle uptake, making these compounds suitable for more specific targeting. Without wishing to be bound by theory, it is postulated that these compounds have a predilection to negatively charged organelles (e.g. mitochondria) due to their cationic charge.

Figure 2:
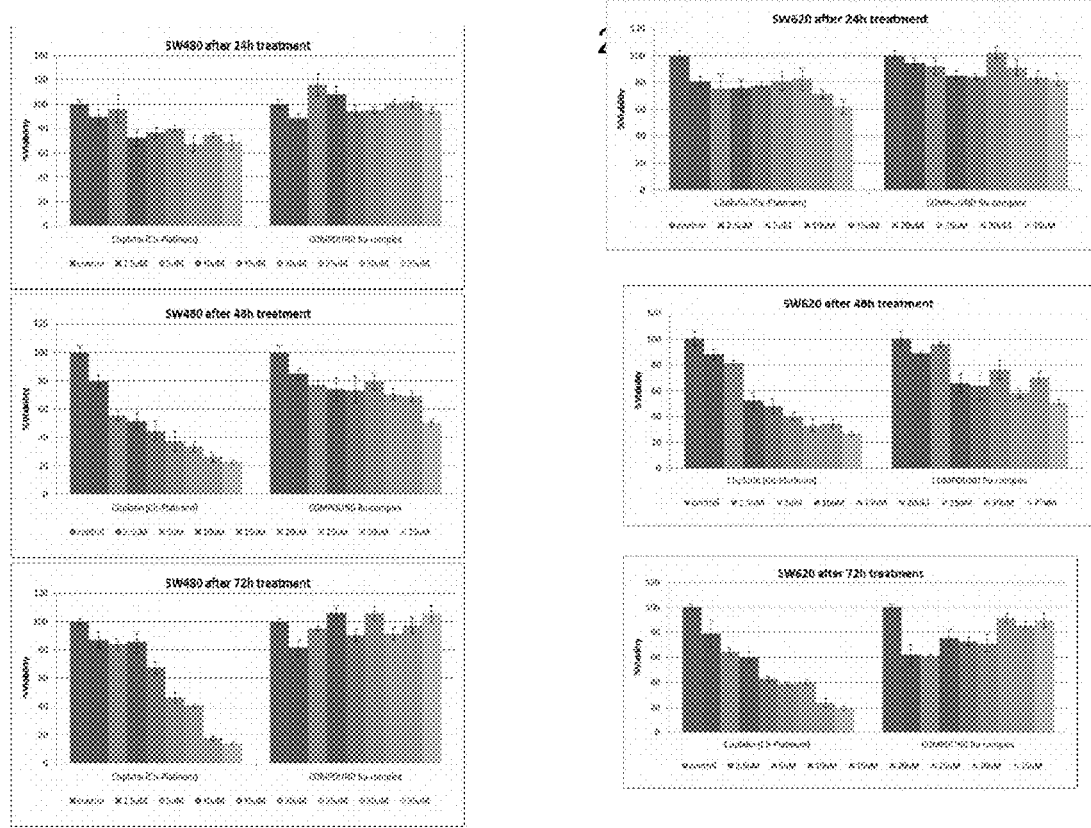
FIG. 2 shows the effect on the viability of colon cancer cells with differential expression of EGFR (SW480, EGFR+ve, SW620, EGFR-ve) of a ruthenium complex in comparison with cis-platinum.

The anti-proliferative efficacy of the ruthenium complex was also examined to rule out non-specific cell killing effect (i.e. non-specific cytotoxicity). The efficacy was assessed against a widely applied metal-based chemotherapeutic, cis-platinum, in colon cancer cells with differential expression of EGFR (SW480, EGFR+ve, SW620, EGFR-ve) in a colorimetric cell viability assay. The results of this experiment are shown in FIG. 2.

No statistically significant antiproliferative effect was observed in EGFR+ve cells (SW480) when compared to cis-platinum. A moderate effect on EGFR-ve cells (SW620) at very high and clinically irrelevant concentrations is attributed to the significantly higher cell sub-population with self-renewal potential. Toxicological assessment with a clonogenicity assay confirmed favourable safety and compatibility for long-term applications in living systems. Therefore, these experiments have shown that the ruthenium complex is suitable for applications and complexation in a tyrosine-kinase specific anti-cancer theranostic system.

The antiproliferative effect of the following compounds A1F, B1F, C1F and D1F were tested on colon cancer cells (SW480).

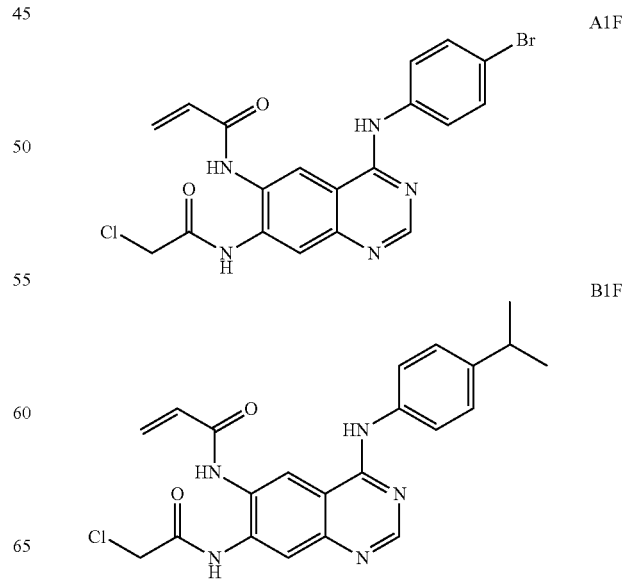

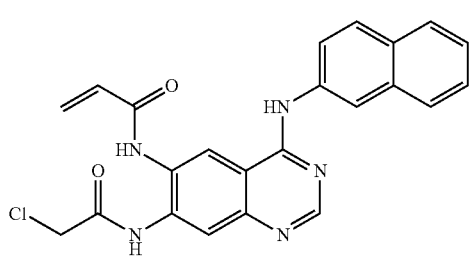

C1F

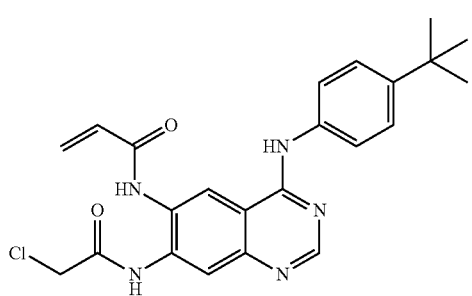

D1F

Figure 3:
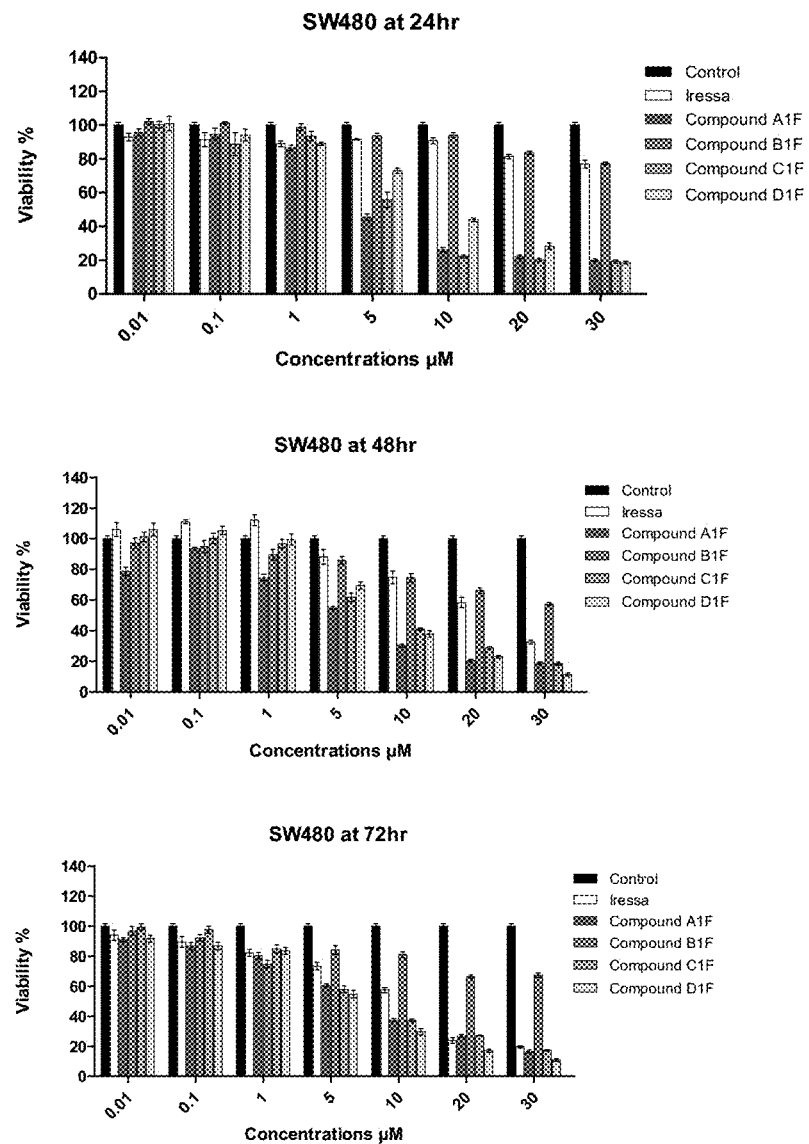
FIG. 3 shows the effect of compounds A1F, B1F, C1F and D1F on the viability of SW480 cells.

The results in FIG. 3 show that compounds A1F, B1F, C1F and D1F all reduce the viability of the cells with respect to the control (no drug). After 24 hours, compounds A1F, C1F and D1F reduced cell viability to 20% with respect to the control (c.f. 80% for gefitinib w.r.t the control).

Example D

An experiment was performed to determine the antiproliferative efficacy of a conjugate of an anilinoquinazoline with an organic fluorophore as the beacon. This aim of this experiment was to see if conjugating the anilinoquinazoline to a beacon would have a positive or negative effect on the binding and inhibiting properties of the anilinoquinazoline. In this example, the organic fluorophore was a cyanine dye. The structure of the conjugate is depicted below:

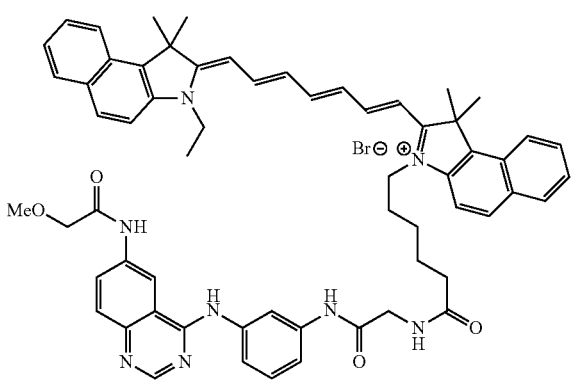 [SMILES: CCN1\C(=C/C=C/C=C/C=C/C2=[N+](CCCCCC(=O)NCC(=O)Nc3cccc(Nc4ncnc5ccc(NC(=O)COC)cc45)c3)c3ccc4ccccc4c3C2(C)C)C(C)(C)c2c1ccc1ccccc21 ; [Br-]]

In order to assure the efficacy of the free anilinoquinazoline molecule in EGFR+ve cells, an ApoPercentage cell-based assay was performed prior to final conjugation with the cyanine. It was determined that the anilinoquinazoline induced programmed cell-death, i.e. specific anti-cancer effect rather than non-specific toxicity (results not shown).

The antiproliferative efficacy of the conjugate was assessed against a commercially available tyrosine kinase inhibitor (gefitinib), a free anilinoquinazoline, and a free cyanine dye (indocyanine green (ICG)) in an MTT colorimetric assay.

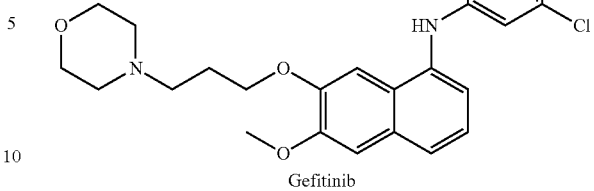

Gefitinib

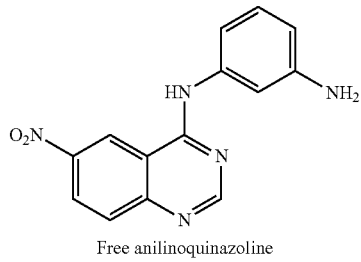

Free anilinoquinazoline

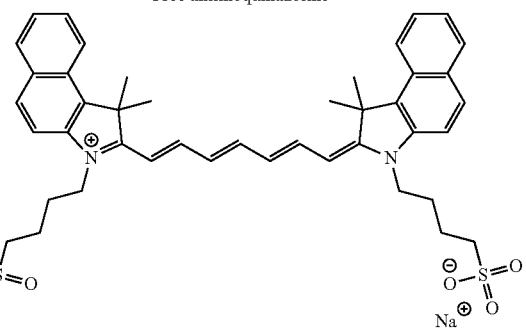

Cyanine (ICG)

Figure 4:
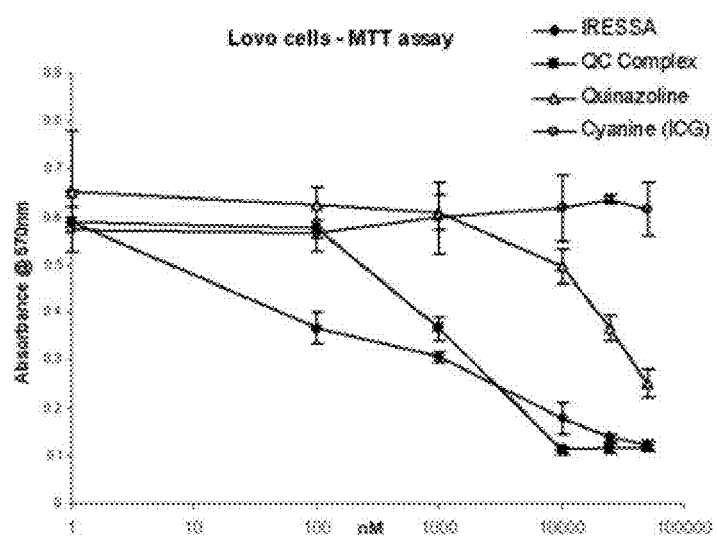
FIG. 4 shows the cytotoxicity of a theranostic system according to the present invention on LoVo cells.

The results of the experiment are shown in FIG. 4 and indicate that the theranostic system has a significantly higher antiproliferative efficacy than free anilinoquinazoline. As expected, the free cyanine dye did not exhibit any antiproliferative effects.

Example E

The present invention relates to the efficacy of theranostic complexes/systems to modulate the interaction between the targeted marker (i.e. TKR) and proteins downstream the pathway and effectively transduce the anti-cancer signals. It has been possible to assess the inter-molecular interactions in Bioluminescence/Fluorescence Resonance Energy Transfer (BRET/FRET) assays. The Innovative Medicines Initiative (IMI, www.imi.europa.eu), which represents the European Technology Platform for novel drug development, has adopted a comprehensive roadmap spanning from Discovery Research through Pharmacovigilance and Phase IV clinical trials. In order to be able to provide a well-characterized prototype and enable its development it is essential to complete major activities entailing "Predictive Pharmacology" and implement advanced Molecular Imaging techniques towards this objective.

"Predictive Pharmacology" involves the identification and validation in the in vitro stage, of surrogate end markers of response to the new therapeutic approach. These markers include proteins interacting with the target molecule (e.g. EGFR) and affect the final outcome of the targeted therapy.

BRET (Bioluminescence Resonance Transfer Energy) is a cutting edge Optical Molecular Imaging technology at the cell culture level and comprises an essential part of modern approaches towards innovative medicines development (Milligan G., *Eur. J. Pharm. Sci.*, 2004 March; 21(4):397-405).

The interaction between the theranostic systems of the present invention with TKRs and effects on the expression, distribution and activity of intracellular targets downstream of EGFR within critical signaling pathways has been evaluated in living cells and in real time with Bioluminescence Resonance Transfer Energy (BRET) assays.

Cell lines were transfected with plasmids expressing proteins emitting at a particular wavelength (biosensors), which is modulated due to the transfer of energy between neighbouring molecules due to resonance. This technology offers a valuable tool in the molecular pharmacology of drug/target and protein-protein interactions, as it can (i) delineate the signaling pathways that are modulated and (ii) identify the intracellular proteins that are chemically associated with the target as a consequence of its (de)activation (response biomarkers).

These assays were used to underscore the specific effect of compounds by measuring the spatial and temporal changes in protein complexes in response to drugs that act over particular pathways. First, different protein—protein interaction pairs were chosen as "sentinels" of the EGFR-signalling pathway and were fused to fluorescent protein fragments. The strategy is based in the principle that drugs having an effect on another protein complex could also affect the downstream labelled complex due to a cascade effect.

Cell lines not expressing the receptors of interest were transfected with plasmids encoding proteins that emit at a given, well defined wavelength due to transfer of energy between two neighbouring molecules (biosensors) due to resonance. The co-transfection involved subcloned plasmids of (a) the receptor/target on a luciferase vector (energy donor) and (b) one of the major proteins of the EGFR signalling cascade modulated by the activation of the target/receptor (e.g. Grb2, p85, pLCγ1, STAT5A, KRas, Raf, Caveolin-1, KSR1 etc) in a pGFP2 vector (energy acceptor). Plasmids useful for this invention were designed and constructed by a commercial provider. They include EGFR-luciferase, GFP2/Grb2, GFP2/KRas, GFP2/Raf, GFP2/Caveolin-1, GFP2/KSR1. Additional constructs also include GFP2/PLCγ1, STAT5A/GFP2 etc.

Colon cell lines negative for EGFR expression were co-transfected with DNA EGFR/luciferase (energy donor) and 40-fold higher dose of DNA plasmid encoding one of GFP2/Grb2, GFP2/KRas, GFP2/Caveolin-1, GFP2/KSR1, STAT5A/GFP2 etc. (energy acceptor), according to the signalling pathway of interest. The 1:40 ratio was established based on previous saturation experiments and has been documented as the optimal in order to assure the best possible augmentation of the optical signal due to resonance transfer energy elicited by the bound compound. Following the transfection the cells were transferred to a solution of glucose and pyruvate in PBS and were grown under FBS starving conditions. Subsequently the clones were incubated with serial concentrations of the compounds with the best EGFR-inhibiting properties.

Interestingly, in the case of the present invention we have a situation where the drug within the theranostic system binding onto the receptor of interest and generating the molecular signal is itself fluorescent. In this case, the drug serves as the "energy acceptor" itself.

Examples were performed for EGFR-Grb2 and caveolin-caveolin interactions. These are membrane proteins related to lipid rafts and play a critical role in EGFR translocation to the mitochondria and the nucleus. Theranostic systems comprising a cyanine dye and a quinazoline showed significant BRET signal-modulating efficacies for interactions in the EGFR cluster (data not shown).

Example F

The intracellular distribution and "pharmacokinetics" of the fluorescent theranostic systems of the natural products described herein denotes their value as (i) probes for the functional analysis of natural chromanols and (ii) potential markers for the detection of mitochondrial targets, such as the translocated phosphoEGFR for cancer prevention and therapy.

In intracellular trafficking experiments, it was determined that enzymatic hydrolysis modifies the optical fluorescent signal. Parallel incubation with a mitochondrial stain confirms the organelle-specific binding of the fluorescent ester. Intracellular hydrolysis of esterified chromanols yields an amplified pro-apoptotic signal in cancer cells. Charged, ester-hydrolysis products serve as active "mitocans" (i.e. cancer therapies targeting the mitochondrial) mediating intrinsic apoptotic pathways and modulating mitochondrial proteins. Phosphorylated EGFR translocated to mitochondria is thus a strong candidate target for mitocans.

A study of the in vivo biodistribution of a dicarboxylic ester of γ-Tocotrienol (DCE-γT) (enabled by customized histopathologic processing and quantitative fluorescence imaging) was performed. The study disclosed liver uptake as a function of time defining fluorescent chromanol esters as valued molecular probes. The structure of the dicarboxylic ester of γ-Tocotrienol (DCE-γT) is as follows:

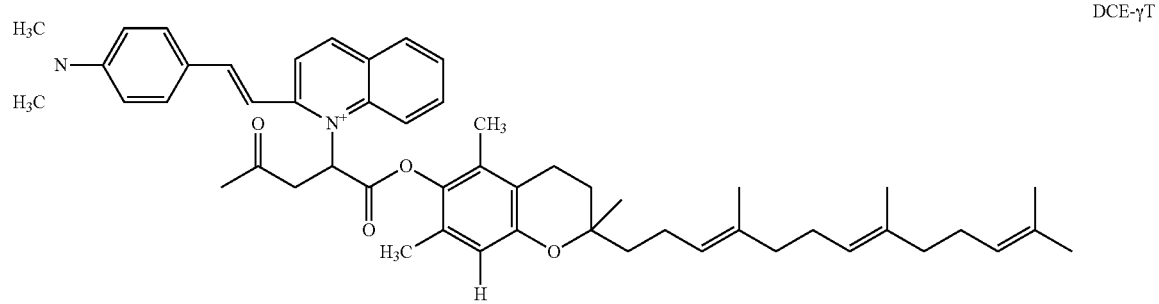

DCE-γT

Fluorescent signals of the DCE-γT and its free fluorescent metabolite, corresponding to the fluorescent ligand, peaked at 30 min and 3 hrs respectively, which was in agreement with in vitro findings. Colon uptake as a function of time confirms the mitochondrial predilection of the esterified chromanols and claims a new generation of optically active mitocans. Further, it was determined that the DCE-γT is uptaken by mouse brain parenchyma cells, and is thus able to pass the blood brain barrier, with more prominent sub-cellular organelle (mitochondria) uptake in the grey matter (data not shown).

Figure 5:
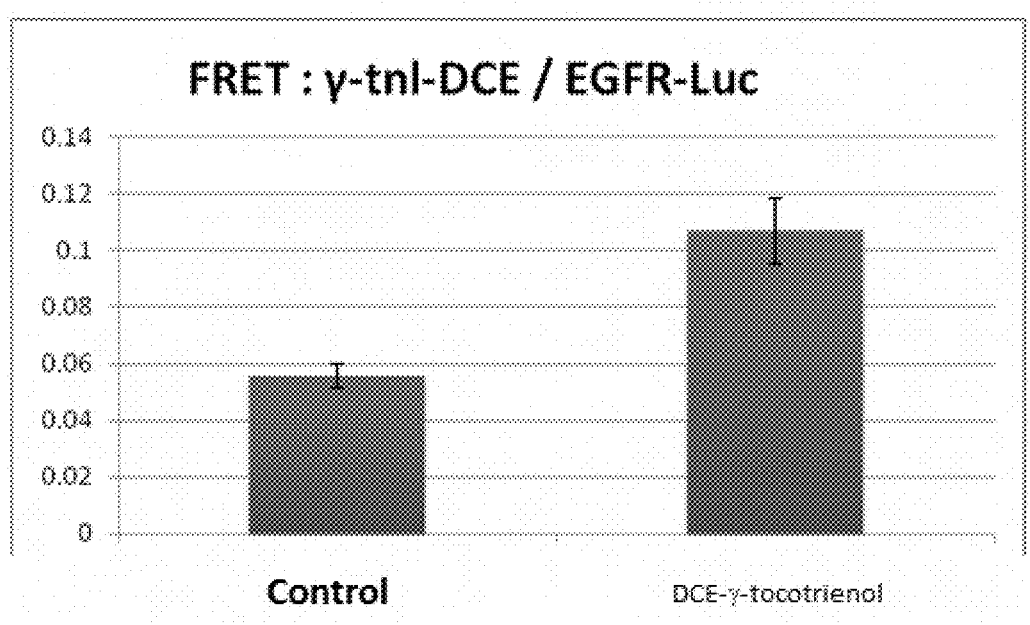
FIG. 5 shows the results of the FRET experiment of Example F.

The fluorescent esters of the natural products disclosed herein can also be used as molecular probes for deciphering the interaction between the natural product and potential biomarkers in cancer cells. EGFR negative colon cancer cells were transiently transfected with a rationally designed EGFR-Luc plasmid and incubated with the DCE-γ-Tocotrienol ester. Bioluminescence of the Luciferase (donor) was assessed against the fluorescence signal of either the DCE-γ-Tocotrienol ester or the hydrolysis product (acceptor). An amplified FRET signal was detected strongly suggesting that the EGFR membrane tyrosine kinase receptor is a potential target for DCE-γ-Tocotrienol (FIG. 5). DCE-γ-Tocotrienol also had an effect on the EGFR axis. However, BRET signals of the interaction between EGFR-Luc and Grb2-GFP demonstrated that neither the ester nor the hydrolysis products elicit any unwanted activation within the EGFR axis.

Example G

The following experiment was performed to uncover new biomarkers of therapeutic response to the anticancer efficacy of the natural product based theranostic systems of the present invention. Label-free temporal and quantitative pharmacoproteomics assessing the protein modulation of DCE-γ-Tocotrienol on colon cancer lymph node metastatic cells, disclosed statistically significant modulation of key proteins across major epigenetics and self-renewal pathways (data not shown).

In this experiment, SW620 cells were seeded in T75 flasks in DMEM, 10% FBS and 1% Penicillin/Streptomycin (all from Gibco). The cells were allowed to attach overnight. The following day the medium was removed and fresh medium containing 0.04 mM of either γT (γ-tocotrienol) or DCE-γT (diluted in absolute ethanol; final concentration of ethanol in the medium was 0.1% v/v). For control untreated cells, equal amount of fresh medium (containing ethanol at 0.1% v/v final concentration) was added.

SW620 cells were harvested after 24, 36 and 48 hrs of incubation with γT or DCE-γT. Briefly, the medium was removed and the cells were rinsed three times with PBS (without Ca, Mg) (Gibco). Fresh PBS was added and the cells were scraped off the flasks and collected in tubes. Collected cells were centrifuged at 1000 rpm (165 g) for 3 min and the supernatant was removed. The cell pellet was re-suspended in PBS and the centrifugation step was repeated. The supernatant was removed and the cells in minimal residual PBS were snap-freezed in liquid nitrogen. Once frozen the cells were stored in −80° C. until the proteomics analysis.

In terms of data analysis, a threshold of relative protein abundance equal or greater than 1.5-fold increase or decrease was set. Proteins with relative abundance equal or greater than 1.5-fold increase (Log(e) ratio≥0.4) or 1.5-fold decrease (Log(e) ratio≤−0.4) compared to control were considered up-regulated or down-regulated respectively. For the functional annotation and classification of up-regulated/down-regulated proteins the Panther Protein Classification System (http://www.pantherdb.org) and the UniProt database (http://www.uniprot.org) were used.

The proteomic analysis of SW620 cells identified 771, 598 and 516 proteins expressed at 24, 36 and 48 hrs of exposure to γT or DCE-γT. Both, γT and DCE-γT are able to evoke an equal or greater that 1.5-fold increase in the expression of a variety of proteins participating in multiple cellular functions.

DCE-γT elicited the expression of 37, 30 and 29 proteins at 24, 36 and 48 hrs respectively. As detailed below, these proteins include mostly histone modification and chromatin remodelling factors; regulators of transcription and translation; modulators of cell cycle and apoptosis; hnRNPs; protein modification factors; components of the vesicular transportation and exocytosis system; and, intracellular signal transducers. Specifically, the proteins elicited by DCE-γ-Tocotrienol were:

histone modification/chromatin remodeling proteins: acidic leucine-rich nuclear phosphoprotein 32 family member B; transcriptional adapter 2-alpha; small nuclear ribonucleoprotein-associated proteins B and B'; core histone macro-H2A.2; transformation/transcription domain-associated protein; lysine-specific histone demethylase 1A; large proline-rich protein BAG6;

transcription regulation proteins: protein lin-52 homolog; UPF0568 protein C14orf166; transcription elongation factor A protein 1;

RNA modification proteins: probable ATP-dependent RNA helicase DDX6; small nuclear ribonucleoprotein-associated protein N; small nuclear ribonucleoprotein-associated proteins B and B'; heterogeneous nuclear ribonucleoprotein L (hnRNP L); beta-catenin-like protein;

DNA replication and repair/cell cycle and apoptosis: pachytene checkpoint protein 2 homolog; single-stranded DNA-binding protein, mitochondrial; DNA replication licensing factor MCM2; annexin A11; protein kinase C epsilon type; acidic leucine-rich nuclear phosphoprotein 32 family member B; chloride intracellular channel protein 1; protein RCC2; omega-amidase NIT2; E3 ubiquitin-protein ligase ZFP91; beta-catenin-like protein 1; large proline-rich protein BAG6;

protein modification/folding proteins: protein phosphatase methylesterase 1; SUMO-activating enzyme subunit 1; T-complex protein 1 subunit alpha; dolichyl-diphosphooligosaccharide-protein glycosyltransferase 48 kDa subunit; dolichyl-diphosphooligosaccharide-protein glycosyltransferase subunit STT3A; and cellular signalling proteins: protein S100-A6; protein tweety homolog 3; serine/threonine-protein kinase LMTK2; ras-related protein Rab-7a; ras-related protein Ral-A; very-long-chain (3R)-3-hydroxyacyl-CoA dehydratase 3.

γT and DCE-γT were also found to induce an epigenetic imprint in SW620 cells. In particular, the expression of proteins involved in epigenetic events and transcriptional regulation was either explicitly elicited or up-regulated in γT and DCE-γT treated cells as opposed to control untreated cells. As detailed below, the epigenetic imprint consists of DNA, RNA and protein methyl-transferases, demethylases, components of HAT and HDAC complexes; histone variants associated with either transcriptionally active chromatin or heterochromatin; DNA and RNA helicases that influence the transcriptional and translational potential; components of the transcription machinery including transcription factors, transcription regulators, co-activators and co-repressors; snRNPs and hnRNPs involved in RNA splicing, RNA processing and histone ≥3'-end processing. γT increased the level of certain snRNP components by ≥3-fold, of RNA helicases by 1.9-fold and of transcription regulators/cofactors by 2-fold, whilst, DCE-γT increased histone H3 forms by 1.8-fold or greater. Notably, γT and DCE-γT increased histone H2A.Z by 24-fold and 23-fold respectively.

Further to the up-regulated or elicited proteins, the γT and DCE-γT dependent epigenetic imprint of SW620 cells also includes down-regulated proteins. γT down-regulated primarily regulators of transcription, snRNPs, hnRNPs and histone H2 and H3 types. In particular, the protein level decreased at least 2-fold for hnRNPs, 1.8-fold for snRNPs, 1.8-fold for histone H2B types and at least 3.7-fold for H3 types. Similarly, DCE-γT decreased certain snRNP components by 2-fold, DNA repair factors by 2-fold, and histone H3 types by at least 6-fold. In summary, proteins modulated by DCE-γ-Tocotrienol were:

Chromatin organization proteins:
  Upregulated: Histone H2B type 1-A; Histone H2A.Z
  Upregulated and subsequently downregulated: Histone H3.1; Histone H3.1t; Histone H3.2; Histone H3.3C; Histone H3.3
  Downregulated: Histone H2A.V; Heterogeneous nuclear ribonucleoprotein C-like 1 (hnRNP CL1)
Histone modification/Chromatin remodeling proteins:
  Upregulated: Ubiquitin carboxyl-terminal hydrolase 7; Cell cycle and apoptosis regulator protein 2
  Upregulated and subsequently downregulated: RuvB-like 2
  Downregulated: Small nuclear ribonucleoprotein E; Small nuclear ribonucleoprotein Sm D3; Small nuclear ribonucleoprotein-associated proteins B and B'
Transcription regulation proteins:
  Upregulated: Cell cycle and apoptosis regulator protein 2
  Upregulated and subsequently downregulated: RuvB-like 2; Ubiquitin carboxyl-terminal hydrolase 7
  Downregulated: X-ray repair cross-complementing protein 5 (XRCC5); Regulation of nuclear pre-mRNA domain-containing protein 1B; Catenin beta-1; Xaa-Pro dipeptidase; Catenin beta-1;
RNA modification proteins:
  Upregulated: Small nuclear ribonucleoprotein Sm D1; Polyadenylate-binding protein 1
  Upregulated and subsequently downregulated:
  Downregulated: Probable ATP-dependent RNA helicase DDX46; Heterogeneous nuclear ribonucleoproteins C1/C2 (hnRNP C1/C2); Small nuclear ribonucleoprotein Sm D3; Small nuclear ribonucleoprotein E (snRNP E); Small nuclear ribonucleoprotein-associated protein N; Nucleolar protein 58; 116 kDa U5 small nuclear ribonucleoprotein component; Small nuclear ribonucleoprotein-associated proteins B and B'; Far upstream element-binding protein 2
DNA replication and repair/Cell cycle and apoptosis proteins:
  Upregulated: Cell cycle and apoptosis regulator protein 2; X-ray repair cross-complementing protein 5 (XRCC5); Glutamate-rich WD repeat-containing protein 1
  Upregulated and subsequently downregulated: RuvB-like 2; UV excision repair protein RAD23 homolog B;
  Downregulated: DNA topoisomerase 2-beta DNA replication licensing factor MCM7; Proliferating cell nuclear antigen PCNA; Regulation of nuclear pre-mRNA domain-containing protein 1B; Apoptosis inhibitor 5
Cellular signaling proteins:
  Uregulated: N/A
  Upregulated and subsequently downregulated: N/A
  Downregulated: Very-long-chain (3R)-3-hydroxyacyl-[acyl-carrier protein] dehydratase 3; Ras-related protein Rab-3A; Ras-related protein Rab-3B; Ras-related protein Rab-3C; Ras-related protein Rab-3D; Ras-related protein Rab-4A; Ras-related protein Rab-43; Polyubiquitin-B.

The invention claimed is:
1. A theranostic system comprising a beacon in combination with or covalently linked to at least one compound selected from the group consisting of:
  a quinazoline-based tyrosine kinase inhibitor and
  a natural product;
  wherein the beacon is a heterometallic compound having a structure as defined by Formula A

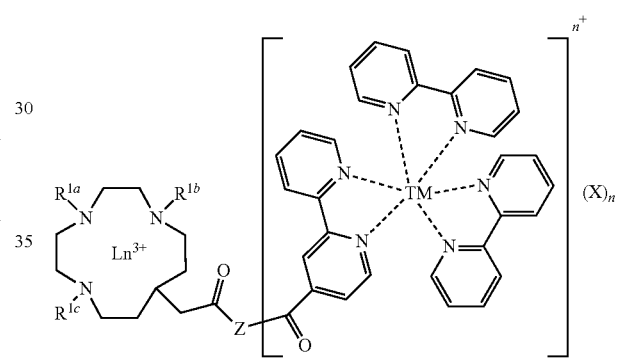

Formula A wherein $R^{1a}$, $R^{1b}$ and $R^{1c}$ each independently represent a hydrogen atom or an optionally substituted alkyl or acyl group; $Ln^{3+}$ is a trivalent lanthanide metal; TM is a transition metal capable of near infrared emission;
X is a negatively charged counterion;
Z is represented by O, NH, S, a poly(ethylene glycol) linker, a $C_1$-$C_{20}$ aliphatic chain or a conjugate of a poly(ethylene glycol) linker with a $C_1$-$C_{20}$ aliphatic chain, wherein the poly(ethylene glycol) linker and the $C_1$-$C_{20}$ aliphatic chain are conjugated via a peptidic or esteric bond; and
n is 2;
wherein the quinazoline-based tyrosine kinase inhibitor has a structure as defined by Formula I:

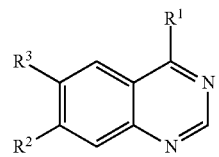

Formula I wherein $R^1$ represents a hydrogen atom, a halogen atom, $N_3$, CN, $NO_2$, $OR^a$, $N(R^a)(R^b)$, $SR^a$ or an optionally substituted alkyl, alkenyl, alkynyl, acyl, cycloalkyl, cycloalkenyl, aryl, aralkyl, heterocyclyl or heterocyclylalkyl group;

$R^2$ represents a hydrogen atom, a halogen atom, $OR^a$, $SR^a$, $N(R^a)(R^b)$, or an optionally substituted alkyl, alkenyl, alkynyl, acyl, cycloalkyl, cycloalkenyl, aryl, aralkyl, heterocyclyl or heterocyclyl alkyl group; and $R^3$ represents a hydrogen atom, a halogen atom, $N_3$, CN, $NO_2$, $OR^a$, $SR^a$ or $N(R^a)(R^b)$, or an optionally substituted alkyl, alkenyl, alkynyl, acyl, cycloalkyl, cycloalkenyl, aryl, aralkyl, heterocyclyl or heterocyclylalkyl group;

wherein $R^a$ and $R^b$ each independently represent a hydrogen atom or an optionally substituted alkyl, alkenyl, alkynyl, acyl, cycloalkyl, cycloalkenyl, aryl, aralkyl, heterocyclyl or heterocyclylalkyl group;

and wherein the natural product is a chromanol of the vitamin E superfamily, selected from α-, β-, γ-, and δ-tocopherols, α-, (β-, γ-, and δ-tocotrienols, and monocarboxylic esters of dicarboxylic acids thereof.

2. A theranostic system according to claim 1, wherein the quinazoline-based tyrosine kinase inhibitor is an anilinoquinazoline-based tyrosine kinase inhibitor having the structure defined by Formula II

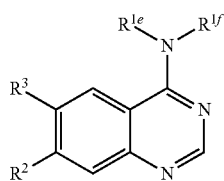

Formula II wherein each $R^{1e}$ and $R^{1f}$ independently represent a hydrogen atom or an optionally substituted alkyl, alkenyl, alkynyl, acyl, cycloalkyl, cycloalkenyl, aryl, aralkyl, heterocyclyl or heterocyclyl alkyl group;

$R^2$ represents a hydrogen atom, a halogen atom, $OR^a$, $SR^a$, $N(R^a)(R^b)$, or an optionally substituted alkyl, alkenyl, alkynyl, acyl, cycloalkyl, cycloalkenyl, aryl, aralkyl, heterocyclyl or heterocyclylalkyl group; and $R^3$ represents a hydrogen atom, a halogen atom, $N_3$, CN, $NO_2$, $OR^a$ or $N(R^a)(R^b)$, or an optionally substituted alkyl, alkenyl, alkynyl, acyl, cycloalkyl, cycloalkenyl, aryl, aralkyl, heterocyclyl or heterocyclyl alkyl group;

wherein $R^a$ and $R^b$ each independently represent a hydrogen atom or an optionally substituted alkyl, alkenyl, alkynyl, acyl, cycloalkyl, cycloalkenyl, aryl, aralkyl, heterocyclyl or heterocyclylalkyl group.

3. A theranostic system according to claim 2, wherein $R^{1e}$ represents a hydrogen atom and $R^{1f}$ represents an optionally substituted aryl, aralkyl, heterocyclyl or heterocyclylalkyl group.

4. A theranostic system according to claim 2 wherein $R^{1f}$ represents

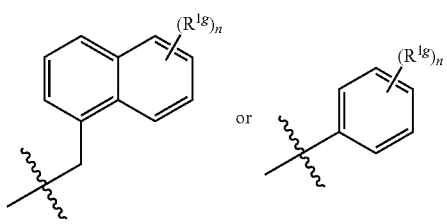

wherein n is 0 to 4, and each $R^{1g}$ independently represents a hydrogen atom, a halogen, $NO_2$, CN, $N_3$, or an optionally substituted alkyl, alkenyl, alkynyl, alkoxy, acyl, cycloalkyl, cycloalkenyl, aryl, aralkyl, heterocyclyl or heterocyclylalkyl group.

5. A theranostic system according to claim 2 wherein $R^{1f}$ represents a 2-methoxyphenyl, 2-bromophenyl, 2-fluorophenyl, 2-chlorophenyl, 3-methoxyphenyl, 3-bromophenyl, 3-fluorophenyl, 3-chlorophenyl, 3,5,difluorophenyl, 3,5,dichlorophenyl, 3,5,dibromophenyl, 3-(trifluoromethyl)phenyl, 4-chloro-3-(trifluoromethyl)phenyl, 3-chloro-4-fluorophenyl, 4-fluoro-3-(trifluoromethyl)phenyl, 4-fluorophenyl, 4-methoxyphenyl, 4-bromophenyl, 4-chlorophenyl, 4-isopropylphenyl, 3-bromo-5-(trifluoromethyl)phenyl, bis(trifluoromethyl)phenyl, 4-(tert-butyl)phenyl or 1-napthylmethyl moiety.

6. A theranostic system according to claim 1, wherein $R^2$ represents a hydrogen atom, a halogen atom $OR^c$, $N(R^c)(R^d)$, $SR^c$ or an optionally substituted alkyl group; wherein Rc and Rd each independently represent a hydrogen atom or an optionally substituted alkyl or acyl group.

7. A theranostic system according to claim 1, wherein $R^3$ represents a hydrogen atom, a halogen atom $OR^g$, $N(R^g)(R^h)$, $SR^g$ or an optionally substituted alkyl, alkenyl or alkynyl group; wherein $R^g$ and $R^h$ each independently represent a hydrogen atom or an optionally substituted alkyl, acyl, alkenyl or alkynyl group.

8. A theranostic system according to claim 1, wherein the system comprises a complex of Formula B

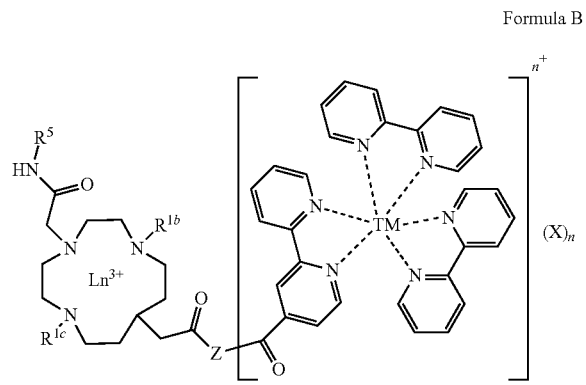

Formula B wherein:

$R^{1a}$, $R^{1b}$ and $R^{1c}$ each independently represent a hydrogen atom or an optionally substituted alkyl or acyl group;

$Ln^{3+}$ is a trivalent lanthanide metal;

TM is a transition metal capable of near infrared emission;

X is a negatively charged counterion;

Z is represented by O, NH, S, a poly(ethylene glycol) linker, a $C_1$-$C_{20}$ aliphatic chain or a conjugate of a poly(ethylene glycol) linker with a $C_1$-$C_{20}$ aliphatic chain, wherein the poly(ethylene glycol) linker and the $C_1$-$C_{20}$ aliphatic chain are conjugated via a peptidic or esteric bond;

n is 2; and $R^5$ is represented by the structure

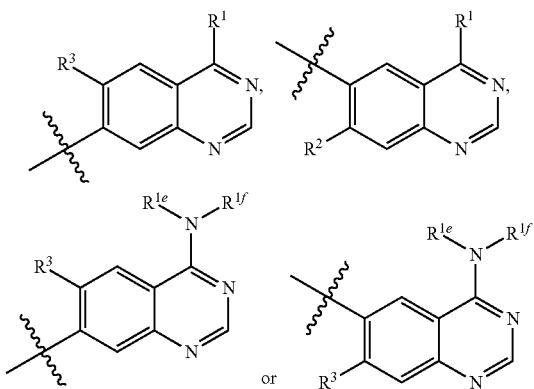

wherein $R^1$ represents a hydrogen atom, a halogen atom, $N_3$, CN, $NO_2$, $OR^a$, $N(R^a)(R^b)$, $SR^a$ or an optionally substituted alkyl, alkenyl, alkynyl, acyl, cycloalkyl, cycloalkenyl, aryl, aralkyl, heterocyclyl or heterocyclylalkyl group, $R^{1e}$ and $R^{1f}$ independently represent a hydrogen atom or an optionally substituted alkyl, alkenyl, alkynyl, acyl, cycloalkyl, cycloalkenyl, aryl, aralkyl, heterocyclyl or heterocyclylalkyl group, $R^2$ represents a hydrogen atom, a halogen atom, $OR^a$, $SR^a$, $N(R^a)(R^b)$, or an optionally substituted alkyl, alkenyl, alkynyl, acyl, cycloalkyl, cycloalkenyl, aryl, aralkyl, heterocyclyl or heterocyclylalkyl group, and $R^3$ represents a hydrogen atom, a halogen atom, $N_3$, CN, $NO_2$, $OR^a$, $SR^a$ or $N(R^a)(R^b)$, or an optionally substituted alkyl, alkenyl, alkynyl, acyl, cycloalkyl, cycloalkenyl, aryl, aralkyl, heterocyclyl or heterocyclylalkyl group, wherein $R^a$ and $R^b$ each independently represent a hydrogen atom or an optionally substituted alkyl, alkenyl, alkynyl, acyl, cycloalkyl, cycloalkenyl, aryl, aralkyl, heterocyclyl or heterocyclyl alkyl group.

9. A theranostic system according to claim 1, wherein the system comprises a complex of Formula III or Formula IV

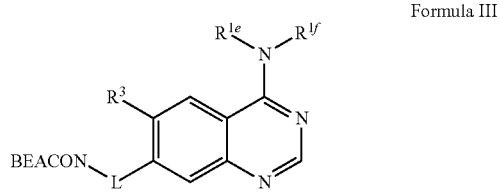

wherein each $R^{1e}$ and $R^{1f}$ independently represent a hydrogen atom or an optionally substituted alkyl, alkenyl, alkynyl, acyl, cycloalkyl, cycloalkenyl, aryl, aralkyl, heterocyclyl or heterocyclylalkyl group;

$R^2$ represents a hydrogen atom, a halogen atom, $OR^a$, $SR^a$, $N(R^a)(R^b)$, or an optionally substituted alkyl, alkenyl, alkynyl, acyl, cycloalkyl, cycloalkenyl, aryl, aralkyl, heterocyclyl or heterocyclylalkyl group; and $R^3$ represents a hydrogen atom, a halogen atom, $N_3$, CN, $NO_2$, $OR^a$ or $N(R^a)(R^b)$, or an optionally substituted alkyl, alkenyl, alkynyl, acyl, cycloalkyl, cycloalkenyl, aryl, aralkyl, heterocyclyl or heterocyclylalkyl group;

wherein $R^a$ and $R^b$ each independently represent a hydrogen atom or an optionally substituted alkyl, alkenyl, alkynyl, acyl, cycloalkyl, cycloalkenyl, aryl, aralkyl, heterocyclyl or heterocyclylalkyl group;

and L is a linker selected from the group consisting of (i) a poly(ethylene glycol) linker, (ii) a $C_1$-$C_{20}$ aliphatic chain; and (iii) a conjugate of a poly(ethylene glycol) linker with a $C_1$-$C_{20}$ aliphatic chain, wherein the poly(ethylene glycol) linker and the $C_1$-$C_{20}$ aliphatic chain are conjugated via a peptidic or esteric bond.

10. A theranostic system according to claim 2, wherein $R^2$ represents a hydrogen atom, a halogen atom, $OR^c$, $N(R^c)(R^d)$, $SR^c$ or an optionally substituted alkyl group; wherein $R^c$ and $R^d$ each independently represent a hydrogen atom or an optionally substituted alkyl or acyl group.

11. A theranostic system according to claim 2, wherein $R^3$ represents a hydrogen atom, a halogen atom $OR^g$, $N(R^g)(R^h)$, $SR^g$ or an optionally substituted alkyl, alkenyl or alkynyl group; wherein $R^g$ and $R^h$ each independently represent a hydrogen atom or an optionally substituted alkyl, acyl, alkenyl or alkynyl group.

12. A theranostic system according to claim 1, comprising said beacon in combination with or complexed to said quinazoline-based tyrosine kinase inhibitor.

13. A theranostic system according to claim 1, comprising said beacon in combination with or complexed to said natural product.

14. A theranostic system according to claim 1, comprising said beacon in combination with or complexed to said quinazoline-based tyrosine kinase inhibitor and further comprising said natural product.

15. A theranostic system according to claim 1, wherein $R^2$ is selected from the group consisting of —NHC(=O)CH$_2$Cl, —SC(=O)CH$_2$Cl, —OC(=O)CH$_2$Cl, —NHC(=O)CH$_2$Br, —SC(=O)CH$_2$Br, —OC(=O)CH$_2$Br, —NHC(=O)CH$_2$F, —SC(=O)CH$_2$F, and —OC(=O)CH$_2$F.

16. A theranostic system according to claim 1, wherein $R^3$ is selected from the group consisting of a hydrogen atom or $OR^m$ or $NH(R^m)$, wherein $R^m$ is an acroyl, crotonoyl, pentenoyl or pentadienoyl group, or wherein $R^m$ is selected from the group consisting of:

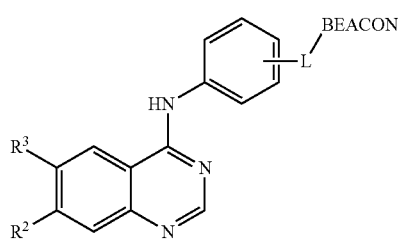
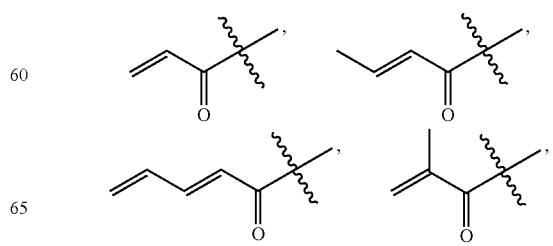

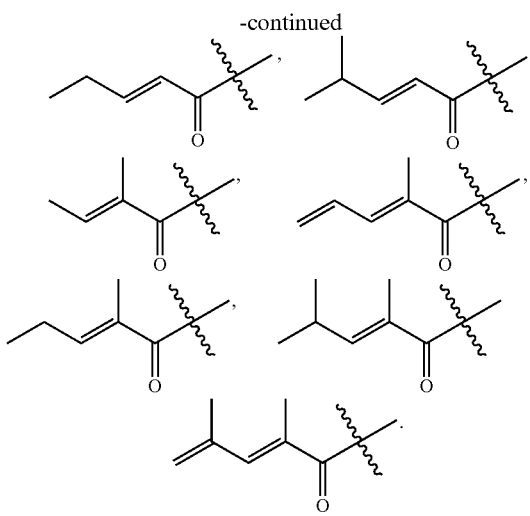

UNITED STATES PATENT AND TRADEMARK OFFICE
CERTIFICATE OF CORRECTION

PATENT NO. : 9,890,187 B2
APPLICATION NO. : 14/751795
DATED : February 13, 2018
INVENTOR(S) : Andreani Odysseos et al.

Page 1 of 1

It is certified that error appears in the above-identified patent and that said Letters Patent is hereby corrected as shown below:

In the Claims

Column 81, Line 37 reads "heterocyclyl alky" should read --heterocyclyalky--

Column 81, Line 45 reads "heterocyclyl alky" should read --heterocyclyalky--

Column 83, Line 44 reads "heterocyclyl alky" should read --heterocyclyalky--

Signed and Sealed this
Third Day of July, 2018

Andrei Iancu
*Director of the United States Patent and Trademark Office*